(12) United States Patent
Chen et al.

(10) Patent No.: US 7,368,126 B2
(45) Date of Patent: *May 6, 2008

(54) CONTROLLED RELEASE DEPOT FORMULATIONS

(76) Inventors: Guohua Chen, 399 Sunset Ave., Sunnyvale, CA (US) 94086; Paul Houston, 3889 Blackstone Ct., Hayward, CA (US) 94542; Roy Bannister, 2090 Nora Dr., Hollister, CA (US) 95023; Teresa Kameda, 1067 Lois Ave., Sunnyvale, CA (US) 94087; David Priebe, 125 NE. 63rd St., Seattle, WA (US) 98115; Lothar Kleiner, 295 Los Altos Ct., Los Altos, CA (US) 94022

( * ) Notice: Subject to any disclaimer, the term of this patent is extended or adjusted under 35 U.S.C. 154(b) by 593 days.

This patent is subject to a terminal disclaimer.

(21) Appl. No.: 10/701,939

(22) Filed: Nov. 4, 2003

(65) Prior Publication Data

US 2004/0151753 A1 Aug. 5, 2004

Related U.S. Application Data

(60) Provisional application No. 60/424,428, filed on Nov. 6, 2002.

(51) Int. Cl.
*A61F 2/00* (2006.01)

(52) U.S. Cl. .................................. 424/426
(58) Field of Classification Search ............... 424/426
See application file for complete search history.

(56) References Cited

U.S. PATENT DOCUMENTS

| | | |
|---|---|---|
| 3,797,492 A | 3/1974 | Place |
| 3,987,790 A | 10/1976 | Eckenhoff et al. |
| 4,008,719 A | 2/1977 | Theeuwes et al. |
| 4,443,340 A | 4/1984 | May et al. |
| 4,853,218 A | 8/1989 | Yim et al. |
| 4,865,845 A | 9/1989 | Eckenhoff et al. |
| 4,938,763 A | 7/1990 | Dunn et al. |
| 4,985,404 A | 1/1991 | Mitchell |
| 5,057,318 A | 10/1991 | Magruder et al. |
| 5,059,423 A | 10/1991 | Magruder et al. |
| 5,085,866 A | 2/1992 | Cowsar et al. |
| 5,112,614 A | 5/1992 | Magruder et al. |
| 5,137,727 A | 8/1992 | Eckenhoff |
| 5,151,093 A | 9/1992 | Theeuwes et al. |
| 5,209,746 A | 5/1993 | Balaban et al. |
| 5,234,692 A | 8/1993 | Magruder et al. |
| 5,234,693 A | 8/1993 | Magruder et al. |
| 5,242,910 A | 9/1993 | Damanj |
| 5,278,201 A | 1/1994 | Dunn et al. |
| 5,279,608 A | 1/1994 | Cherif Cheikh |
| 5,308,348 A | 5/1994 | Balaban et al. |
| 5,310,865 A | 5/1994 | Enomoto et al. |
| 5,336,057 A | 8/1994 | Fukuda et al. |
| 5,456,679 A | 10/1995 | Balaban et al. |
| 5,468,253 A | 11/1995 | Bezwada et al. |
| 5,556,905 A | 9/1996 | Frappier et al. |
| 5,599,552 A | 2/1997 | Dunn et al. |
| 5,620,700 A | 4/1997 | Berggren et al. |
| 5,639,851 A | 6/1997 | Bezwada et al. |
| 5,651,986 A | 7/1997 | Brem et al. |
| 5,654,010 A | 8/1997 | Johnson et al. |
| 5,656,297 A | 8/1997 | Bernstein et al. |
| 5,713,920 A | 2/1998 | Bezwada et al. |
| 5,714,551 A | 2/1998 | Bezwada et al. |
| 5,733,950 A | 3/1998 | Dunn et al. |
| 5,780,044 A | 7/1998 | Yewey et al. |
| 5,868,788 A | 2/1999 | Bezwada et al. |
| 5,990,194 A | 11/1999 | Dunn et al. |
| 6,113,624 A | 9/2000 | Bezwada et al. |
| 6,130,200 A | 10/2000 | Brodbeck et al. |
| 6,331,311 B1 | 12/2001 | Brodbeck et al. |
| 6,432,438 B1 | 8/2002 | Shukla |
| 2003/0170289 A1 | 9/2003 | Chen et al. |
| 2003/0180364 A1 | 9/2003 | Chen et al. |
| 2004/0001889 A1 | 1/2004 | Chen et al. |
| 2004/0022859 A1 | 2/2004 | Chen et al. |
| 2004/0024069 A1 | 2/2004 | Chen et al. |
| 2005/0106214 A1 | 5/2005 | Chen |
| 2005/0281879 A1 | 12/2005 | Chen et al. |

FOREIGN PATENT DOCUMENTS

WO    WO 93/24150 A    12/1993

(Continued)

OTHER PUBLICATIONS

Eliaz, et al., "Characterization of a polymeric PLGA-injectable implant deliver system for the controlled release of proteins," J. Biomed. Materials Res., 50(3):388-396, 2000.

Jain, et al., "Controlled drug delivery by biodegradable poly(ester) devices: different preparative approaches," Drug. Dev. Ind. Pharm., 24(8):703-727.

Jain, R.A., "The manufacturing techniques of various drug loaded biodegradable poly(lactide-co-glycolide) (PLGA) devices," Biomaterials, 21(23): 2475-90, 2000.

Lambert, et al., "Development of an in situ forming biodegradable poly-lactide-co-glycolide system for controlled release of proteins," Journal of Controlled Release, 33(1995) 189-195.

(Continued)

*Primary Examiner*—Sharon E. Kennedy
(74) *Attorney, Agent, or Firm*—TraskBritt

(57) ABSTRACT

Methods and compositions for systemically or locally administering a beneficialagent to a subject are described, and include, for example, depot gel compositions that can be injected into a desired location and which can provide controlled release of a beneficial agent over a prolonged duration of time. The compositions include a biocompatible polymer, a biocompatible solvent having low water miscibility that forms a viscous gel with the polymer and limits water uptake by the implant, and a beneficial agent.

89 Claims, 24 Drawing Sheets

FOREIGN PATENT DOCUMENTS

| | | | |
|---|---|---|---|
| WO | WO 95/13799 A | | 5/1995 |
| WO | WO 98/27962 | | 7/1998 |
| WO | WO 98/27963 | | 7/1998 |
| WO | WO 00/74650 A | | 12/2000 |
| WO | WO 02/00137 A1 | | 1/2002 |
| WO | WO 02/38185 | * | 5/2002 |
| WO | WO 02/38185 A | | 5/2002 |
| WO | WO 02/058670 A1 | | 8/2002 |
| WO | WO 02/067991 A | | 9/2002 |
| WO | WO 03/041684 A | | 5/2003 |
| WO | WO 03/041685 A | | 5/2003 |
| WO | WO 03/041757 A | | 5/2003 |
| WO | WO 04/000269 A | | 12/2003 |
| WO | WO 2004/011054 A | | 2/2004 |

OTHER PUBLICATIONS

Ravivarapu, et al., "Polymer and microsphere blending to alter the release of a peptide from PLGA microspheres," Eurpoean Journal of Pharmaceutics and Biopharmaceutics, Elsevier Science Publishers B.V., Amsterdam, NL, vol. 50, No. 2, Sep. 2000.

International Search Report dated May 18, 2004 (9 pages).

* cited by examiner

CONTROLLED RELEASE DEPOT FORMULATIONS

This application claims the benefit of U.S. Provisional Application No. 60/424,428 filed Nov. 6, 2002, which is incorporated herein by reference.

BACKGROUND OF THE INVENTION

1. Field of the Invention

The present invention relates to a depot gel composition that can be injected into a desired location and which can provide controlled release of a beneficial agent over a specified/desired duration of time. The present invention also relates to a method of preparing and administering the composition.

2. Description of the Related Art

Biodegradable polymers have been used for many years in medical applications. Illustrative devices composed of the biodegradable polymers include sutures, surgical clips, staples, implants, and drug delivery systems. The majority of these biodegradable polymers have been based upon glycolide, lactide, caprolactone, and copolymers thereof.

The biodegradable polymers can be thermoplastic materials, meaning that they can be heated and formed into various shapes such as fibers, clips, staples, pins, films, etc. Alternatively, they can be thermosetting materials formed by crosslinking reactions, which lead to high molecular weight materials that do not melt or form flowable liquids at high temperatures. Although thermoplastic and thermosetting biodegradable polymers have many useful biomedical applications, there are several important limitations to their use in the bodies of various animals including humans, animals, birds, fish, and reptiles.

Solid implant drug delivery systems containing a drug incorporated in thermoplastic or thermosetting biodegradable polymers have been widely used successfully. Such implants have to be inserted into the body through an incision which is sometimes larger than desired by the medical profession and occasionally lead to a reluctance of the patients to accept such an implant or drug delivery system. The following U.S. Pat. Nos. 5,456,679; 5,336,057; 5,308,348; 5,279,608; 5,234,693; 5,234,692; 5,209,746; 5,151,093; 5,137,727; 5,112,614; 5,085,866; 5,059,423; 5,057,318; 4,865,845; 4,008,719; 3,987,790 and 3,797,492 are believed to be representative of such drug delivery systems and are incorporated herein by reference. These patents disclose reservoir devices, osmotic delivery devices and pulsatile delivery devices for delivering beneficial agents.

Injecting drug delivery systems as small particles, microspheres, or microcapsules avoids the incision needed to implant drug delivery systems. However, these materials do not always satisfy the demand for a biodegradable implant. These materials are particulate in nature, do not form a continuous film or solid implant with the structural integrity needed for certain prostheses, the particles tend to aggregate and thus their behavior is hard to predict. When inserted into certain body cavities, such as a mouth, a periodontal pocket, the eye, or the vagina, where there is considerable fluid flow, these small particles, microspheres, or microcapsules are poorly retained because of their small size and discontinuous nature. Further, if there are complications, removal of microcapsule or small-particle systems from the body without extensive surgical intervention is considerably more difficult than with solid implants. Additionally, manufacture, storage and injectability of microspheres or microcapsules prepared from these polymers and containing drugs for release into the body present problems.

The art has developed various drug delivery systems in response to the aforementioned challenges. The following U.S. Pat. Nos. 6,432,438; 5,990,194; 5,780,044; 5,733,950; 5,620,700; 5,599,552; 5,556,905; 5,278,201; 5,242,910 and 4,938,763; and PCT publications WO 98/27962; WO 02/00137 and WO 02/058670 are believed to be representative and are incorporated herein by reference. See also Jain, R. et al., "Controlled drug delivery by biodegradable poly(ester) devices: different preparative approaches", *Drug Dev. Ind. Pharm.*, 24(8): 703-727, 1998; Eliaz, R. E. and Kost, J., "Characterization of a polymeric PLGA-injectable implant delivery system for the controlled release of proteins", *J. Biomed. Master Res.*, 50(3): 388-396, 2000; and Jain, R. A., "The manufacturing techniques of various drug loaded biodegradable poly(lactide-co-glycolide) (PLGA) devices", *Biomaterials*, 21(23): 2475-90, 2000. These patents and publications disclose polymer compositions for injectable implants using solvents and/or plasticizers.

Previously described polymer compositions for injectable implants have used solvent/plasticizers that are very or relatively soluble in aqueous body fluids to promote rapid solidification of the polymer at the implant site and promote diffusion of drug from the implant. Rapid migration of water into such polymeric implants utilizing water soluble polymer solvents when the implants are placed in the body and exposed to aqueous body fluids presents a serious problem. The rapid water uptake often results in implants having pore structures that are nonhomogeneous in size and shape. Typically, the surface pores take on a finger-like pore structure extending for as much as one-third of a millimeter or more from the implant surface into the implant, and such finger-like pores are open at the surface of the implant to the environment of use. The internal pores tend to be smaller and less accessible to the fluids present in the environment of use. The rapid water uptake characteristic often results in uncontrolled release of beneficial agent that is manifested by an initial, rapid release of beneficial agent from the polymer composition, corresponding to a "burst" of beneficial agent being released from the implant. The burst often results in a substantial portion of the beneficial agent, if not all, being released in a very short time, e.g., hours or 1-2 days. Such an effect can be unacceptable, particularly in those circumstances where a controlled delivery is desired, i.e., delivery of beneficial agent in a controlled manner over a period of greater than or equal to a month or up to one year, or where there is a narrow therapeutic window and release of excess beneficial agent can result in adverse consequences to the subject being treated, or where it is necessary to mimic the naturally occurring daily profile of beneficial agents, such as hormones and the like, in the body of the subject being treated.

Accordingly, when such devices are implanted, the finger-like pores allow very rapid uptake of aqueous body fluids into the interior of the implant with consequent immediate and rapid dissolution of significant quantities of beneficial agent and unimpeded diffusion of beneficial agent into the environment of use, producing the burst effect discussed above.

Furthermore, rapid water uptake can result in premature polymer precipitation such that a hardened implant or one with a hardened skin is produced. The inner pores and much of the interior of the polymer containing beneficial agent are shut off from contact with the body fluids and a significant reduction in the release of beneficial agent can result over a not insignificant period of time ("lag time"). That lag time is undesirable from the standpoint of presenting a controlled, sustained release of beneficial agent to the subject being treated. What one observes, then, is a burst of beneficial agent being released in a short time period immediately after implantation, a lag time in which no or very little beneficial agent is being released, and subsequently continued delivery of beneficial agent (assuming beneficial agent remains after the burst) until the supply of beneficial agent is exhausted.

Various approaches to control burst and modulate and stabilize the delivery of the beneficial agent have been described. The following U.S. Pat. Nos. 6,130,200; 5,990,194; 5,780,044; 5,733,950; 5,656,297; 5,654,010; 4,985,404 and 4,853,218 and PCT publication WO 98/27962 are believed to be representative and are incorporated herein by reference. Notwithstanding some success, those methods have not been entirely satisfactory for the large number of beneficial agents that would be effectively delivered by an implant.

SUMMARY OF THE INVENTION

The present invention provides a method and an injectable depot gel composition for systemic and local delivery of a beneficial agent to a subject over a prolonged duration of time. In particular, the invention provides controlled release of the beneficial agent to the subject being treated, the release being controlled over a period from about, equal to or greater than two weeks or up to one year after administration, i.e., from about two weeks to about twelve months after administration, preferably over a period equal to or greater than one month after administration or preferably over a period from about one month to about twelve months after administration; more preferably over a period equal to or greater than 2 months after administration, preferably over a period equal to or greater than 3 months after administration, preferably over a period of about 3 months to about 9 months after administration, preferably over a period of about 3 months to about 6 months after administration, even more preferably over a period of up to about 3 months, up to about 4 months, up to about 5 months and up to about 6 months after administration. A single administration of the injectable depot gel composition provides longer sustained release of active agents over a prolonged duration of time, thus reducing the frequency of administration and improving patient compliance. Additionally, the invention provides a method of preparing the injectable depot gel composition.

In one aspect, the invention pertains to an injectable depot composition for sustained delivery of a beneficial agent to a subject in a controlled manner over a predetermined duration of time after administration comprising:
(a) a viscous gel formulation comprising:
  (1) a bioerodible, biocompatible polymer, wherein the polymer is a lactic acid-based polymer; and
  (2) a solvent having a miscibility in water of less than or equal to 7 wt. % at 25° C., in an amount effective to plasticize the polymer and form a gel therewith; and
(b) a beneficial agent dissolved or dispersed in the gel;

wherein the beneficial agent is delivered over a duration equal to or greater than one month.

Preferably, the polymer is a copolymer of lactic acid and glycolic acid, having a comonomer ratio (an L/G ratio) of about 50:50 to about 100:0; and a molecular weight ranging from about 3,000 to about 120,000.

In another aspect, the invention pertains to an injectable depot composition for sustained delivery of a beneficial agent to a subject in a controlled manner over a predetermined duration of time after administration comprising:
(a) a viscous gel formulation comprising:
  (1) a bioerodible, biocompatible polymer, wherein the polymer is a lactic acid-based polymer; and
  (2) a solvent having a miscibility in water of less than or equal to 7 wt. % at 25° C., in an amount effective to plasticize the polymer and form a gel therewith; and
(b) a beneficial agent dissolved or dispersed in the gel;

wherein the beneficial agent is delivered over a duration equal to or greater than one month.

Preferably, the polymer is a copolymer of lactic acid and a caprolactone-based polymer including caprolactone (CL), having a comonomer ratio (an L/CL ratio) of about 25:75 to about 75:25; and a molecular weight ranging from about 3,000 to about 120,000.

In another aspect, the invention pertains to an injectable depot composition for sustained systemic delivery of a beneficial agent to a subject in a controlled manner over a duration equal to or greater than one month after administration comprising: (a) a viscous gel formulation comprising: (1) a bioerodible, biocompatible polymer, wherein the polymer is a lactic acid-based polymer; and (2) a solvent having a miscibility in water of less than or equal to 7 wt. % at 25° C., in an amount effective to plasticize the polymer and form a gel therewith; and (b) a beneficial agent dissolved or dispersed in the gel.

In an additional aspect, the invention pertains to an injectable depot composition for sustained delivery of a beneficial agent to a subject in a controlled manner over a predetermined duration of time after administration comprising: (a) a viscous gel formulation comprising: (1) a bioerodible, biocompatible polymer, wherein the polymer is a lactic acid-based polymer; and (2) a solvent having a miscibility in water of less than or equal to 7 wt. % at 25° C., in an amount effective to plasticize the polymer and form a gel therewith; and (b) a beneficial agent dissolved or dispersed in the gel; wherein the beneficial agent is delivered systemically in a controlled manner over a duration equal to or greater than one month after administration.

In another aspect, the invention pertains to an injectable depot composition sustained local delivery of a beneficial agent to a subject in a controlled manner over a duration equal to or greater than one month after administration comprising: (a) a viscous gel formulation comprising: (1) a bioerodible, biocompatible polymer, wherein the polymer is a lactic acid-based polymer; and (2) a solvent having a miscibility in water of less than or equal to 7 wt. % at 25° C., in an amount effective to plasticize the polymer and form a gel therewith; and (b) a beneficial agent dissolved or dispersed in the gel.

In an additional aspect, the invention pertains to an injectable depot composition for sustained delivery of a beneficial agent to a subject in a controlled manner over a predetermined duration of time after administration comprising: (a) a viscous gel formulation comprising: (1) a bioerodible, biocompatible polymer, wherein the polymer is a lactic acid-based polymer; and (2) a solvent having a miscibility in water of less than or equal to 7 wt. % at 25° C., in an amount effective to plasticize the polymer and form a gel therewith; and (b) a beneficial agent dissolved or dispersed in the gel; wherein the beneficial agent is delivered locally in a controlled manner over a duration equal to or greater than one month after administration.

In another aspect, the invention pertains to an injectable depot composition as described above, further including at least one of the following: a pore former; a solubility modulator for the beneficial agent; and an osmotic agent.

In another aspect, the invention pertains to an injectable depot composition as described above, wherein the viscous gel further comprises a polymer, such as a biodegradable polymer, selected from the group consisting of polylactides, polyglycolides, caprolactone-based polymers, poly(caprolactone), polyanhydrides, polyamines, polyesteramides, polyorthoesters, polydioxanones, polyacetals, polyketals, polycarbonates, polyphosphoesters, polyesters, polybutylene terephthalate, polyorthocarbonates, polyphosphazenes, succinates, poly(malic acid), poly(amino acids), polyvinylpyrrolidone, polyethylene glycol, polyhydroxycellulose, polysaccharides, chitin, chitosan, hyaluronic acid, and copolymers, terpolymers and mixtures thereof.

In another aspect, the invention pertains to an injectable depot composition as described above, wherein the solvent is selected from an aromatic alcohol having the structural formula (I)

Ar—(L)n-OH (I)

in which Ar is a substituted or unsubstituted aryl or heteroaryl group, n is zero or 1, and L is a linking moiety; and a solvent selected from the group consisting of esters of aromatic acids, aromatic ketones, and mixtures thereof.

In preferred embodiments, the solvent is selected from the aromatic alcohol, lower alkyl and aralkyl esters of aryl acids; aryl, aralkyl and lower alkyl ketones; and lower alkyl esters of citric acid. Preferably, the solvent is selected from benzyl alcohol, benzyl benzoate and ethyl benzoate. In preferred embodiments, the composition is free of solvents having a miscibility in water that is greater than 7 wt. % at 25° C. Preferably the solvent has a miscibility in water of less than 7 wt. %, more preferably less than 5 wt. %, and even more preferably less than 3 wt. %.

In additional aspects, the invention pertains to methods of administering a beneficial agent to a subject in a controlled manner over a duration equal to or greater than one month after administration, comprising administering an injectable depot composition as described above. In certain embodiments, the beneficial agent is delivered systemically in a controlled manner over a duration equal to or greater than one month after administration. In additional embodiments, the beneficial agent is delivered locally in a controlled manner over a duration equal to or greater than one month after administration.

In additional aspects, the invention pertains to a kit for sustained delivery administration of a beneficial agent to a subject in a controlled manner over a predetermined duration of time after administration comprising:

(a) a bioerodible, biocompatible polymer, wherein the polymer is a lactic acid-based polymer;
(b) a solvent having a miscibility in water of less than or equal to 7 wt. % at 25° C., in an amount effective to plasticize the polymer and form a gel therewith;
(c) a beneficial agent dissolved or dispersed in the gel; and optionally, one or more of the following:
(d) an emulsifying agent;
(e) a pore former;
(f) a solubility modulator for the beneficial agent, optionally associated with the beneficial agent; and
(g) an osmotic agent;

wherein at least the beneficial agent, optionally associated with the solubility modulator, is maintained separated from the solvent until the time of administration of the beneficial agent to a subject. In additional embodiments, the kit comprises a metering device, such as syringe, catheter, pump, syringe pump, autoinjector and the like.

These and other embodiments of the present invention will readily occur to those of ordinary skill in the art in view of the disclosure herein.

BRIEF DESCRIPTION OF THE DRAWINGS

The foregoing and other objects, features and advantages of the present invention will be more readily understood upon reading the following detailed description in conjunction with the drawings as described hereinafter.

DETAILED DESCRIPTION OF THE INVENTION

Figure 1:
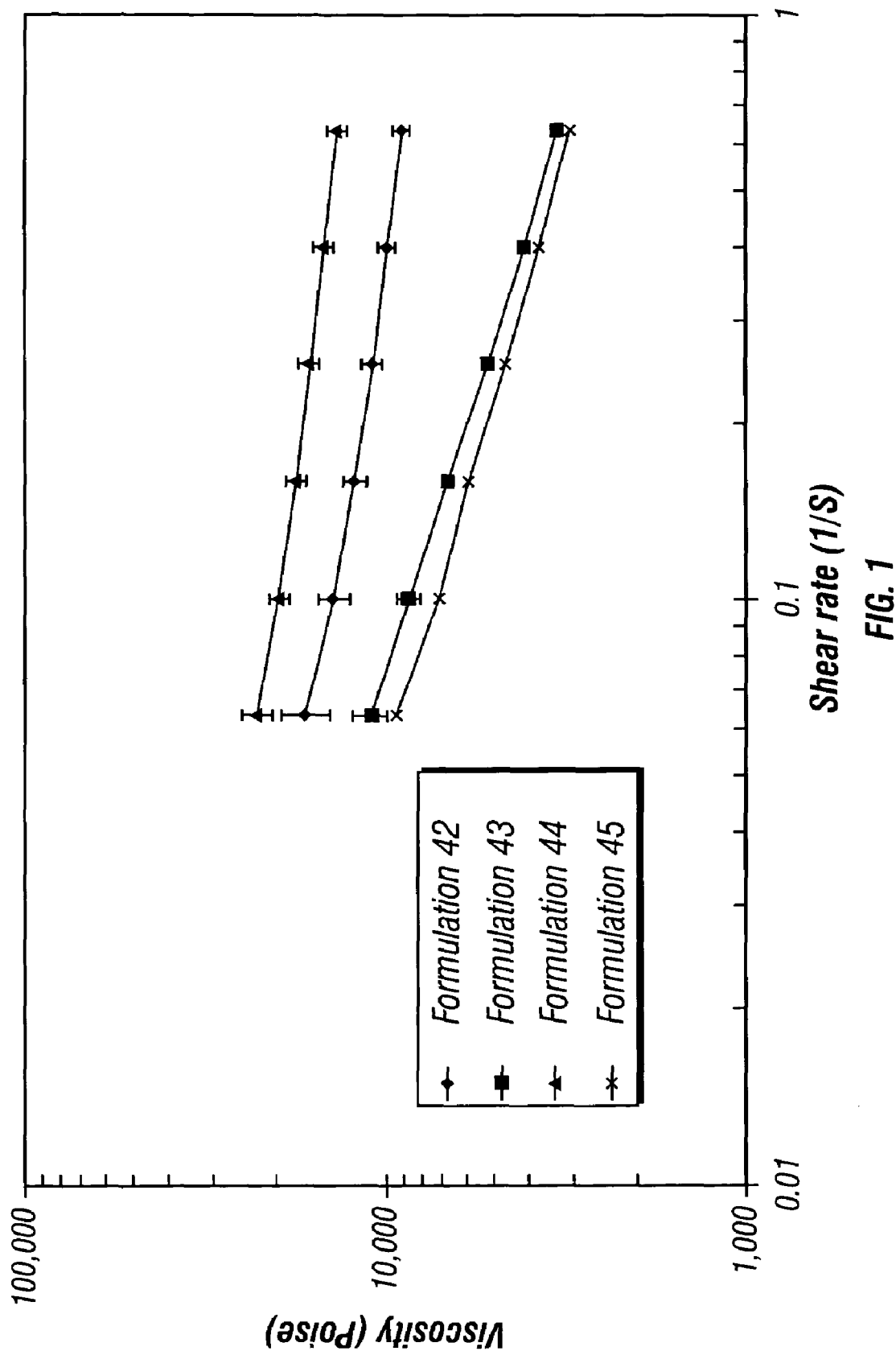
FIG. 1 is a graph illustrating the rheological properties of the depot formulations of the present invention (formulations 42-45).

Overview and Definitions:

The present invention is directed to an injectable depot composition for delivery of a beneficial agent to a subject over a prolonged duration of time, at multiple sites if required, and for multiple or repeated injections, i.e., for instances where the therapeutic effect of the beneficial agent has subsided or period of time for the beneficial agent to have a therapeutic effect has lapsed or for instances where the subject requires further administration of the beneficial agent for any reason, wherein the injectable depot composition serves as an implanted sustained release beneficial agent delivery system after injection into a patient's body. In particular, the invention provides controlled release of the beneficial agent to the subject being treated, the release being controlled over a period about, equal to or greater than two weeks and up to one year after administration, i.e., a period of about two weeks to about twelve months after administration, preferably over a period equal to or greater than one month after administration; more preferably over a period equal to or greater than 2 months after administration, preferably over a period equal to or greater than 3 months after administration, preferably over a period of about 3 months to about 9 months after administration, preferably over a period of about 3 months to about 6 months after administration, even more preferably over a period of up to about 3 months, up to about 4 months, up to about 5 months, and up to about 6 months after administration. The present invention also relates to a method of using the injectable depot composition to administer a beneficial agent to a patient.

The injectable depot composition is a gel formed from a polymer matrix comprising a bioerodible, biocompatible polymer; a solvent having a miscibility in water of less than or equal to 7 wt. % at 25° C., in an amount effective to plasticize the polymer and form a gel therewith; and a beneficial agent dissolved or dispersed in the gel. The present invention is also directed to a method of systemically or locally administering and delivering a beneficial agent to a subject by implanting in the subject an injectable depot composition as described above. The method of systemic or local delivery of the present invention is at multiple sites, if required, and is also directed toward multiple or repeated injections, i.e., for instances where the therapeutic effect of the beneficial agent has subsided or period of time for the beneficial agent to have a therapeutic effect has lapsed or for instances where the subject requires further administration of the beneficial agent for any reason.

By appropriate choice of solvent, water migration from the aqueous environment surrounding the implant system is restricted, and beneficial agent is released to the subject over a period of time, thus providing for delivery of the beneficial agent with a controlled burst of beneficial agent and sustained release thereafter.

Surprisingly, it has been found that the release rate of the beneficial agent from the injectable depot gel formulations of the invention can be varied by varying the polymer properties, such as the type of polymer, the molecular weight of the polymer (including the modal distribution of the polymer), and the comonomer ratio of the monomers forming the polymer, the end group of the polymers; the type of solvent; and by varying the polymer/solvent ratios to provide a controlled, sustained release of a beneficial agent over a prolonged duration of time equal to or greater than two weeks and up to one year after administration, i.e., from about two weeks to about twelve months after administration, or preferably over a period from about one month to about twelve months after administration, preferably over a period equal to or greater than one month after administration, more preferably over a period equal to or greater than 2 months after administration, preferably over a period equal to or greater than 3 months after administration, preferably over a period of about 3 months to about 9 months after administration, preferably over a period of about 3 months to about 6 months after administration, even more preferably over a period of up to about 3 months, up to about 4 months, up to about 5 months, and up to about 6 months after administration. The release rate profile and duration can be controlled by the appropriate choice of a polymer (including the ratio of the monomers, e.g., L/G, CL/L ratios), the molecular weight of the polymer (LMW, MMW, HMW), the end group of the polymer (acid, ester); a water immiscible solvent, the polymer/solvent ratio, emulsifying agent, pore former, solubility modifier for the beneficial agent, an osmotic agent, and the like.

Additionally, the present invention provides a method of regulating the release of a beneficial agent from an injectable depot composition. The duration and the rate of release of the beneficial agent are controlled by the appropriate choice of the biodegradable polymer, the molecular weight of the polymer, the comonomer ratio of the various monomers forming the polymer (e.g., the L/G or CL/L ratio for a given polymer), the polymer/solvent ratios, and combinations of these factors, as described in greater detail below (see also Tables A, B, C and D below).

In some embodiments, pore formers and solubility modulators of the beneficial agent may be added to the implant systems to provide desired release profiles from the implant systems, along with typical pharmaceutical excipients and other additives that do not change the beneficial aspects of the present invention.

The composition provides controlled sustained release of the beneficial agent by restricting water migration from the aqueous environment surrounding the implant system, thus delivering the beneficial agent over a prolonged duration as described earlier. A single administration of the injectable depot gel composition provides longer sustained release of active agents over a prolonged duration of time, thus reducing the frequency of administration and improving patient compliance. Because the polymer of the composition is bioerodible, the implant system does not have to be surgically removed after beneficial agent is depleted from the implant. Moreover, the polymer of the composition in accordance with the present invention is bioerodible, it can be administered both systemically or locally, to include delivery at multiple sites, if required, and is also usable for multiple or repeated administrations, such as repeated injections, particularly for instances where the therapeutic effect of the beneficial agent has subsided or the period of time for the beneficial agent to have a therapeutic effect has lapsed or for instances where the subject requires further administration of the beneficial agent for any reason.

Generally, the compositions of the invention are gel-like and form with a substantially homogeneous nonporous structure throughout the implant upon implantation and during drug delivery, even as it hardens. Furthermore, while the polymer gel implant will slowly harden when subjected to an aqueous environment, the hardened implant may maintain a rubbery (nonrigid) composition with the glass transition temperature $T_g$ being below 37° C.

The preferred compositions herein allow beneficial agent to be loaded into the interior of the polymer at levels that are above that required to saturate the beneficial agent in water, thereby facilitating zero order release of beneficial agent. Additionally, the preferred compositions may provide viscous gels that have a glass transition temperature that is less than 37° C., such that the gel remains nonrigid for a period of time after implantation of 24 hours or more.

It has been discovered that when a solvent having a solubility in water of less than 7% by weight in water is present in the system, suitable burst control and sustained delivery of beneficial agent is achieved, whether or not a solubility modulator of the beneficial agent is present in the system. Typically, the implant systems useful in this invention will release, in the first 2 days after implantation, 60% or less of the total amount of beneficial agent to be delivered to the subject from the implant system, preferably 50% or less, more preferably 40% or less and even more preferably 30% or less.

When the composition is intended for implantation by injection, the viscosity optionally may be modified by addition of emulsifiers or thixotropic agents to obtain a gel composition having a viscosity low enough to permit passage of the gel composition through a needle. Also, pore formers and solubility modulators of the beneficial agent may be added to the implant systems to provide desired release profiles from the implant systems, along with typical pharmaceutical excipients and other additives that do not change the beneficial aspects of the present invention. The addition of a solubility modulator to the implant system may enable the use of a solvent having a solubility of 7% or greater by weight in the implant system with minimal burst and sustained delivery under particular circumstances. However, it is presently preferred that the implant system utilize at least one solvent having a solubility in water of less than 7% by weight, whether the solvent is present alone or as part of a solvent mixture. It has also been discovered that when mixtures of solvents which include a solvent having 7% or less by weight solubility in water and one or more miscible solvents, optionally having greater solubility, are used, implant systems exhibiting limited water uptake and minimal burst and sustained delivery characteristics are obtained.

Definitions

In describing and claiming the present invention, the following terminology will be used in accordance with the definitions set out below:

The singular forms "a," "an" and "the" include plural referents unless the context clearly dictates otherwise. Thus, for example, reference to "a solvent" includes a single solvent as well as a mixture of two or more different solvents, reference to "a beneficial agent" includes a single beneficial agent as well as two or more different beneficial agents in combination, and the like.

The term "beneficial agent" means an agent that affects a desired beneficial, often pharmacological, effect upon-administration to a human or an animal, whether alone or in combination with other pharmaceutical excipients or inert ingredients.

The term "AUC" means the area under the curve obtained from an in vivo assay in a subject by plotting blood plasma concentration of the beneficial agent in the subject against time, as measured from the time of implantation of the composition, to a time "t" after implantation. The time t will correspond to the delivery period of beneficial agent to a subject.

The term "burst index" means, with respect to a particular composition intended for systemic delivery of a beneficial agent, the quotient formed by dividing (i) the AUC calculated for the first time period after implantation of the composition into a subject divided by the number of hours in the first time period (t1), by (ii) the AUC calculated for the time period of delivery of beneficial agent, divided by the number of hours in the total duration of the delivery period (t2). For example, the burst index at 24 hours is the quotient formed by dividing (i) the AUC calculated for the first twenty-four hours after implantation of the composition into a subject divided by the number 24, by (ii) the AUC calculated for the time period of delivery of beneficial agent, divided by the number of hours in the total duration of the delivery period.

The phrase "dissolved or dispersed" is intended to encompass all means of establishing a presence of beneficial agent in the gel composition and includes dissolution, dispersion, suspension and the like.

The term "systemic" means, with respect to delivery or administration of a beneficial agent to a subject, that the beneficial agent is detectable at a biologically significant level in the blood plasma of the subject.

The term "local" means, with respect to delivery or administration of a beneficial agent to a subject, that the beneficial agent is delivered to a localized site in the subject but is not detectable at a biologically significant level in the blood plasma of the subject.

The terms "prolonged period" or "prolonged duration" are used interchangeably and refer to a period of time over which release of a beneficial agent from the depot gel composition of the invention occurs, which will generally be over a period equal to or greater than two weeks or up to one year after administration, preferably over a period equal to or greater than one month after administration, more preferably over a period equal to or greater than 2 months after administration, preferably over a period equal to or greater than 3 months after administration, preferably over a period of up to about 3 months to about 9 months after administration; preferably over a period of up to about 3 months to about 6 months after administration, and even more preferably over a period of up to about 3 months, up to about 4 months, up to about 5 months; and up to about 6 months after administration.

The term "gel vehicle" means the composition formed by mixture of the polymer and solvent in the absence of the beneficial agent.

The term "initial burst" means, with respect to a particular composition of this invention, the quotient obtained by dividing (i) the amount by weight of beneficial agent released from the composition in a predetermined initial period of time after implantation, by (ii) the total amount of beneficial agent that is to be delivered from an implanted composition. It is understood that the initial burst may vary depending on the shape and surface area of the implant. Accordingly, the percentages and burst indices associated with initial burst described herein are intended to apply to compositions tested in a form resulting from dispensing of the composition from a standard syringe.

The term "solubility modulator" means, with respect to the beneficial agent, an agent that will alter the solubility of the beneficial agent, with reference to polymer solvent or water, from the solubility of beneficial agent in the absence of the modulator. The modulator may enhance or retard the solubility of the beneficial agent in the solvent or water. However, in the case of beneficial agents that are highly water soluble, the solubility modulator will generally be an agent that will retard the solubility of the beneficial agent in water. The effects of solubility modulators of the beneficial agent may result from interaction of the solubility modulator with the solvent, or with the beneficial agent itself, such as by the formation of complexes, or with both. For the purposes hereof, when the solubility modulator is "associated" with the beneficial agent, all such interactions or formations as may occur are intended. Solubility modulators may be mixed with the beneficial agent prior to its combination with the viscous gel or may be added to the viscous gel prior to the addition of the beneficial agent, as appropriate.

The terms "subject" and "patient" mean, with respect to the administration of a composition of the invention, an animal or a human being.

The term "thixotropic" is used in its conventional sense to refer to a gel composition that can liquefy or at least exhibit a decrease in apparent viscosity upon application of mechanical force such as shear force. The extent of the reduction is in part a function of the shear rate of the gel when subjected to the shearing force. When the shearing force is removed, the viscosity of the thixotropic gel returns to a viscosity at or near that which it displayed prior to being subjected to the shearing force. Accordingly, a thixotropic gel may be subjected to a shearing force when injected from a syringe which temporarily reduces its viscosity during the injection process. When the injection process is completed, the shearing force is removed and the gel returns very near to its previous state.

"A thixotropic agent" as used herein is one that increases the thixotropy of the composition in which it is contained, promoting shear thinning and enabling use of reduced injection force.

The term "bioerodible" refers to a material that gradually decomposes, dissolves, hydrolyzes and/or erodes in situ. Generally, the "bioerodible" polymers herein are polymers that are hydrolyzable, and bioerode in situ primarily through hydrolysis.

The term "low molecular weight (LMW) polymer" refers to bioerodible polymers having an average molecular weight ranging from about 3,000 to about 10,000; preferably from about 3,000 to about 9,000; more preferably from about 4,000 to about 8,000; and more preferably the low molecular weight polymer has a molecular weight of about 7,000, about 6,000, about 5,000, about 4,000 and about 3,000 as determined by gel permeation chromatography (GPC).

The term "medium molecular weight (MMW) polymer" refers to biocompatible, bioerodible polymers having an average molecular weight ranging from between about 10,000 to about 30,000; preferably from about 12,000 to about 20,000; more preferably from about 14,000 to about 18,000; and more preferably the medium molecular weight polymer has a molecular weight of about 14,000, about 15,000, about 16,000, about 17,000 and about 18,000 as determined by gel permeation chromatography (GPC). In preferred embodiments, a MMW polymer is selected from PLGA RG502, PLGA RG752, and PLA R202.

The term "high molecular weight (HMW) polymer" refers to biocompatible, bioerodible polymers having an average molecular weight of greater than 30,000; preferably from about 30,000 to about 250,000; more preferably from about 30,000 to about 120,000 as determined by gel permeation chromatography (GPC). In preferred embodiments, a HMW polymer is selected from RG503, PLGA RG 755, PLA R206, PCL/PLA 75:25 and PCL/PLA 25:75.

Since all solvents, at least on a molecular level, will be soluble in water (i.e., miscible with water) to some very limited extent, the term "immiscible" as used herein means that 7% or less by weight, preferably 5% or less, of the solvent is soluble in or miscible with water. For the purposes of this disclosure, solubility values of solvent in water are considered to be determined at 25° C. Since it is generally recognized that solubility values as reported may not always be conducted at the same conditions, solubility limits recited herein as percent by weight miscible or soluble with water as part of a range or upper limit may not be absolute. For example, if the upper limit on solvent solubility in water is recited herein as "7% by weight," and no further limitations on the solvent are provided, the solvent "triacetin," which has a reported solubility in water of 7.17 grams in 100 ml of water, is considered to be included within the limit of 7%. A solubility limit in water of less than 7% by weight as used herein does not include the solvent triacetin or solvents having solubilities in water equal to or greater than triacetin.

The following definitions apply to the molecular structures described herein: As used herein, the phrase "having the formula" or "having the structure" is not intended to be limiting and is used in the same way that the term "comprising" is commonly used.

The term "alkyl" as used herein refers to a saturated hydrocarbon group typically, although not necessarily, containing 1 to about 30 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, preferably 1 to 4 carbon atoms. "Substituted alkyl" refers to an alkyl substituted with one or more substituent groups, and the terms "heteroatom-containing alkyl" and "heteroalkyl" refer to an alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl or lower alkyl.

The term "aryl" as used herein, and unless otherwise specified, refers to an aromatic substituent containing a single aromatic ring or multiple aromatic rings that are fused together, linked covalently, or linked to a common group such as a methylene or ethylene moiety. Preferred aryl groups contain one aromatic ring or two fused or linked aromatic rings, e.g., phenyl, naphthyl, biphenyl, diphenylether, diphenylamine, benzophenone, and the like, and most preferred aryl groups are monocyclic. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the term "aryl" includes heteroaryl, substituted aryl, and substituted heteroaryl groups.

The term "aralkyl" refers to an alkyl group substituted with an aryl group, wherein alkyl and aryl are as defined above. The term "heteroaralkyl" refers to an alkyl group substituted with a heteroaryl group. Unless otherwise indicated, the term "aralkyl" includes heteroaralkyl and substituted aralkyl groups as well as unsubstituted aralkyl groups. Generally, the term "aralkyl" herein refers to an aryl-substituted lower alkyl group, preferably a phenyl substituted lower alkyl group such as benzyl, phenethyl, 1-phenylpropyl, 2-phenylpropyl, and the like.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heterocyclic" refers to a cyclic substituent that is heteroatom-containing, the term "heteroaryl" refers to an aryl substituent that is heteroatom-containing, and the like.

By "substituted" as in "substituted alkyl," "substituted aryl" and the like, as alluded to in some of the aforementioned definitions, is meant that in the alkyl or aryl moiety, respectively, at least one hydrogen atom bound to a carbon atom is replaced with one or more noninterfering substituents such as hydroxyl, alkoxy, thio, amino, halo, and the like.

I. Injectable Depot Compositions:

As described previously, injectable depot compositions for delivery of beneficial agents over a prolonged period of time may be formed as viscous gels prior to injection of the depot into a subject. The viscous gel supports dispersed beneficial agent to provide appropriate delivery profiles, which include those having low initial burst, of the beneficial agent as the beneficial agent is released from the depot over time.

The polymer, solvent and other agents of the invention must be biocompatible, that is, they must not cause irritation or necrosis in the environment of use. The environment of use is a fluid environment and may comprise a subcutaneous, intramuscular, intravascular (high/low flow), intramyocardial, adventitial, intratumoral, or intracerebral portion, wound sites, tight joint spaces or body cavity of a human or animal. In certain embodiments, the beneficial agent may be administered locally to avoid or minimize systemic side effects. Gels of the present invention containing a beneficial agent may be injected/implanted directly into or applied as a coating to the desired location, e.g., subcutaneous, intramuscular, intravascular, intramyocardial, adventitial, intratumoral, or intracerebral portion, wound sites, tight joint spaces or body cavity of a human or animal.

Typically, the viscous gel will be injected from a standard hypodermic syringe through a needle, a catheter, or a trocar, that has been prefilled with the beneficial agent-viscous gel composition to form the depot. It is often preferred that injections take place using the smallest size needle (i.e., smallest diameter) to reduce discomfort to the subject when the injection is in a subcutaneous, intramuscular, intravascular (high/low flow), intramyocardial, adventitial, intratumoral, or intracerebral portion, wound site, tight joint space or body cavity of a human or animal. It is desirable to be able to inject gels through a needle or a catheter ranging from 16 gauge and higher, preferably 20 gauge and higher, more preferably 22 gauge and higher, and even more preferably 24 gauge and higher. With highly viscous gels, i.e., gels having a viscosity of about 200 poise or greater, injection forces to dispense the gel from a syringe having a needle in the 20-30 gauge range may be so high as to make the injection difficult or reasonably impossible when done manually. At the same time, the high viscosity of the gel is desirable to maintain the integrity of the depot after injection and during the dispensing period and also to facilitate desired suspension characteristics of the beneficial agent in the gel.

A. The Bioerodible, Biocompatible Polymer:

Polymers that are useful in conjunction with the methods and compositions of the invention are bioerodible, i.e., they gradually degrade, e.g., enzymatically or hydrolyze, dissolve, physically erode, or otherwise disintegrate within the aqueous fluids of a patient's body. Generally, the polymers bioerode as a result of hydrolysis or physical erosion, although the primary bioerosion process is typically hydrolysis or enzymatic degradation.

Such polymers include, but are not limited to polylactides, polyglycolides, caprolactone-based polymers, polycaprolactones, polyanhydrides, polyamines, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, hydroxymethylcellulose polyphosphoesters, polyesters, polybutylene terephthalate, polysaccharides, chitin, chitosan, hyaluronic acid and copolymers, terpolymers and mixtures thereof.

Surprisingly, it has been found that the release rate of the beneficial agent from the injectable depot gel formulations of the invention can be varied by varying the polymer properties, such as the type of polymer, the molecular weight of the polymer (including the modal distribution of the polymer), and the comonomer ratio of the monomers forming the polymer; the end group of the polymers; the type of solvent; and by varying the polymer/solvent ratios to provide a controlled, sustained release of a beneficial agent over a prolonged duration of time equal to or greater than two weeks and up to one year after administration, preferably over a period equal to or greater than one month after administration; preferably over a period equal to or greater than 2 months after administration, preferably over a period equal to or greater than 3 months after administration, preferably over a period of about 3 months to about 9 months after administration, more preferably over a period of about 3 months to about 6 months after administration, preferably over a period of up to about 3 months, up to about 4 months, up to about 5 months; and up to about 6 months after administration. The release rate profile and duration can be controlled by the appropriate choice of a polymer (including the ratio of the monomers, e.g., L/G, CL/L ratios), the molecular weight of the polymer (LMW, MMW, HMW), the end group of the polymer (acid, ester); a water immiscible solvent, the polymer/solvent ratio, emulsifying agent, pore former, solubility modifier for the beneficial agent, an osmotic agent, and the like.

In another aspect, the present invention provides a method of regulating the release of a beneficial agent from an injectable depot composition. The duration and the rate of release of the beneficial agent (e.g., burst index and release rate profile) are controlled by the appropriate choice of the biodegradable polymer, the molecular weight of the polymer, the comonomer ratio of the various monomers forming the polymer (e.g., the L/G or CL/L ratio for a lactic acid-based polymer), and the polymer/solvent ratios as tabulated in Tables A, B, C and D below. Previously described injectable depot formulations having polylactic acid (i.e., a L/G ratio of 100:0) exhibit a release profile of the beneficial agent over a duration of about 3 months (which is shorter than the comparable depot composition of the instant invention, see e.g., Examples 20 and 21, and FIGS. 13, 16 and 17 as described in greater detail hereinafter). As illustrated in the Examples below, it has been discovered that PLGA depot gel compositions of the invention having a L/G ratio of about 75:25 release the beneficial agent in a sustained manner over a period of approximately 3-4 months. In additional embodiments, PLGA depot gel compositions of the invention having a L/G ratio of about 100:0 (i.e., polylactic acid (PLA)) and a P/S ratio of about 55:45 to about 65:35, release the beneficial agent in a sustained manner over a period of approximately 6-8 months. In additional embodiments, PLGA depot gel compositions of the invention having a molecular weight of about 14,000 to about 22,000; a L/G ratio of about 75:25 to about 100:0 and a P/S ratio of about 50:50 to about 65:35, release the beneficial agent in a sustained manner over a period of approximately 3-8 months.

In one aspect, duration and the rate of release (e.g., release rate profile and burst index) of the beneficial agent are controlled by the appropriate choice of the biodegradable polymer.

(A) Molecular weight of the polymer: The molecular weight of the polymer can be varied to regulate the release rate profile and/or delivery duration of the beneficial agent. In general, as the molecular weight of the polymer increases, one or more of the following occurs: the burst index is lower, release rate profile is flatter and/or duration of delivery is longer.

(B) Polymers with different end groups: Depot gel compositions having a blend of polymers with different end groups would result in a depot formulation having a lower burst index than those polymers that are not blended and a regulated duration of delivery. For example, blending PLGA RG502H (acid end group) with PLGA RG502 (ester end group) lowers the burst index for a depot gel composition having a one month duration of delivery; blending PLGA RG752H with PLGA RG752 lowers the burst index for a depot gel composition having a duration of delivery of about 3 months to about 4 months; blending PLA R202H with PLA R202 lowers the burst index for a depot gel composition having a duration of delivery greater than or equal to 6 months; blending PLGA RG502H and PLGA RG752 with PLA R202 lowers the burst index for a depot gel composition having a duration of delivery greater than or equal to 6 months. In accordance with the invention, the depot gel compositions comprise a blend of polymers, i.e., a blend of polymer components, and preferably, the blend of polymers includes at least one lactic acid-based polymer as one of the polymer components of the depot gel composition.

(C) Comonomer Ratio of the Polymer:

Varying the comonomer ratio of the various monomers forming the polymer (e.g., the L/G or CL/L ratio for a given polymer), would result in depot gel compositions having a lower burst index and a regulated duration of delivery. For example, a depot gel composition having a polymer with a L/G ratio of 50:50 has a short duration of delivery ranging from 2 days to about one month; a depot gel composition having a polymer with a L/G ratio of 65:35 has a duration of delivery of about 2 months; a depot gel composition having a polymer with a L/G ratio of 75:25 or L/CL ratio of 75:25 has a duration of delivery of about 3 months to about 4 months; a depot gel composition having a polymer with a L/G ratio of 85:15 has a duration of delivery of about 5 months; and a depot gel composition having a polymer with a PLA or L/CL ratio of 25:75 has a duration of delivery greater than or equal to 6 months.

(D) Polymers with different degradation characteristics: Depot gel compositions having a blend of a faster degrading polymer with a slower degrading polymer would result in a depot formulation having a lower burst index and a longer duration of delivery. For example, blending PLGA RG 502 with PLGA RG752 would yield a depot gel composition having a lower burst index (as compared to a gel composition having PLGA RG752 alone) and a duration of delivery of about 3 months to about 4 months after administration. Blending PLGA RG502 and PLGA RG752 with PLA R202 would yield a depot gel composition having a lower burst index (as compared to a gel composition having PLA 202 alone) and a duration of delivery greater than or equal to 6 months after administration.

(E) Polymers with Different Molecular Weight, End Group and Comonomer Ratios: Depot gel compositions having a blend of polymers having different molecular weight, end group and comonomer ratios result in a depot formulation having a lower burst index and a regulated duration of delivery. For example, blending LMW PLGA (L/G: 50/50) and PLGA RG502H (acid end group) with PLGA RG502 (ester end group) would yield a depot gel composition having a lower burst index (as compared to a gel composition having PLGA RG502 alone) and a duration of delivery of about one month. Blending LMW PLGA (L/G: 50/50) and PLGA RG503H (acid end group) with PLGA RG752 (ester end group) would yield a depot gel composition having a lower burst index (as compared to a gel composition having PLGA RG752 alone) and a duration of delivery of about 3 months to about 4 months after administration. Blending LMW PLGA (L/G: 50/50) and PLGA RG755H (acid end group) with PLA R202 (ester end group) would yield a depot gel composition having a lower burst index (as compared to a gel composition having PLA 202 alone) and a duration of delivery greater than or equal to 6 months after administration. Blending PLGA RG502H (acid end group) and PLGA RG752 (ester end group) with PLA R206 (ester end group) would yield a depot gel composition having a lower burst index (as compared to a gel composition having PLA 202 alone) and a duration of delivery greater than or equal to 6 months after administration.

In another aspect, duration and the rate of release of the beneficial agent are controlled by varying the polymer/solvent (P/S) ratio. The polymer/solvent ratio of the depot gel composition can be varied to regulate the release rate profile and/or delivery duration of the beneficial agent. In general, the higher the P/S ratio, the lower the burst index or flatter release rate profile.

TABLE A

| # | Polymer | L/G Ratio | MW | End group | Delivery Duration |
|---|---------|-----------|-----|-----------|-------------------|
| A1 | LMW PLGA | 50/50 | <10,000 | Alkyl ester | 2-14 days |
| A2 | LMW PLGA-H | 50/50 | <10,000 | —COOH | 2-14 days |
| A3 | PLGA RG502 | 50/50 | 16,000 | Alkyl ester | 2-6 weeks |
| A4 | PLGA RG502H | 50/50 | 15,000 | —COOH | 2-4 weeks |
| A5 | PLGA RG503 | 50/50 | 38,000 | Alkyl ester | 4-8 weeks |
| A6 | PLGA RG503H | 50/50 | 38,000 | —COOH | 4-6 weeks |
| A7 | PLGA RG752 | 75/25 | 18,000 | Alkyl ester | 3-4 months |
| A8 | PLGA RG752H | 75/25 | 18,000 | —COOH | 2-3 months |
| A9 | PLGA RG756 | 75/25 | 56,000 | Alkyl ester | 3-4 months |
| A10 | PLGA RG756H | 75/25 | 56,000 | —COOH | 2-4 months |
| A11 | PLA R202 | 100/0 | 15,000 | Alkyl ester | 4-9 months |
| A12 | PLA R202H | 100/0 | 15,000 | —COOH | 4-9 months |
| A13 | PLA R206 | 100/0 | 60,000 | Alkyl ester | 6-12 months |
| A14 | PLA R206H | 100/0 | 60,000 | —COOH | 6-12 months |

TABLE B

| Formulation | LMW PLGA (%) | PLGA RG502 (%) | PLGA RG503 (%) | PLGA RG752 (%) | PLGA RG756 (%) | PLA R202 (%) | PLA R206 (%) | Total Polymer (%) |
|---|---|---|---|---|---|---|---|---|
| B1 | 35 | 10 | 5 | — | — | — | — | 50 |
| B2 | 43 | 0 | 7 | — | — | — | — | 50 |
| B3 | 15 | 10 | — | 25 | — | — | — | 50 |
| B4 | 18 | 12 | — | 30 | — | — | — | 60 |
| B5 | 15 | — | — | 25 | — | 10 | — | 50 |
| B6 | 16.5 | — | — | 27.5 | — | 11 | 1 | 55 |
| B7 | — | 15 | — | 25 | — | 10 | — | 50 |
| B8 | — | 20 | — | 20 | — | 10 | — | 50 |
| B9 | — | 18 | — | 18 | — | 9 | — | 45 |
| B10 | — | 20 | — | 10 | 10 | 10 | — | 50 |
| B11 | — | 20 | — | 10 | — | 20 | — | 50 |
| B12 | — | 18 | — | 9 | — | 18 | — | 45 |
| B13 | — | 20 | — | 10 | — | 10 | 10 | 50 |
| B14 | — | 15 | — | 15 | — | 10 | 10 | 50 |
| B15 | — | 20 | — | 10 | — | — | 20 | 50 |

TABLE C

| Formulation | PLGA RG502 (%) | PLGA RG502H (%) | PLGA RG752 (%) | PLGA RG752H (%) | PLA R202 (%) | Total Polymer (%) |
|---|---|---|---|---|---|---|
| C1 | 25 | 25 | — | — | — | 50 |
| C2 | 25 | 15 | — | — | — | 40 |
| C3 | — | — | 25 | 25 | — | 50 |
| C4 | — | — | 30 | 25 | — | 55 |
| C5 | — | 15 | 20 | — | 20 | 55 |
| C6 | — | 15 | 20 | — | 25 | 60 |

TABLE D

| Formulation | LMW PLGA (%) | PLGA RG502H (%) | PLGA RG503H (%) | PLGA RG752 (%) | PLGA RG755H (%) | PLA R202 (%) | PLA R206 (%) | Total Polymer (%) |
|---|---|---|---|---|---|---|---|---|
| D1 | 15 | — | 10 | 25 | — | — | — | 50 |
| D2 | 15 | — | 10 | 20 | — | — | — | 45 |
| D3 | 10 | — | — | — | 15 | 25 | — | 50 |
| D4 | 10 | — | — | — | 20 | 25 | — | 55 |
| D5 | — | 15 | — | 15 | — | — | 20 | 50 |
| D6 | — | 15 | — | 20 | — | — | 20 | 55 |

The bioerodible polymers are selected from the group consisting of low molecular weight (LMW) polymers, medium molecular weight (MMW) polymers and high molecular weight (HMW) polymers. The low molecular weight (LMW) bioerodible polymers have an average molecular weight ranging from about 3,000 to about 10,000; preferably from about 3,000 to about 9,000; more preferably from about 4,000 to about 8,000; and more preferably the low molecular weight polymer has a molecular weight of about 7,000, about 6,000, about 5,000, about 4,000 and about 3,000 as determined by gel permeation chromatography (GPC).

The medium molecular weight (MMW) bioerodible polymers have an average molecular weight ranging from between about 10,000 to about 30,000; preferably from about 12,000 to about 20,000; more preferably from about 14,000 to about 18,000; and more preferably the medium molecular weight polymer has a molecular weight of about 14,000, about 15,000, about 16,000, about 17,000 and about 18,000 as determined by gel permeation chromatography (GPC). In preferred embodiments, an MMW polymer is selected from PLGA RG502, PLGA RG752, and PLA R202.

The high molecular weight (HMW) bioerodible polymers have an average molecular weight of greater than 30,000; preferably from about 30,000 to about 250,000; more preferably from about 30,000 to about 120,000 as determined by gel permeation chromatography (GPC). In preferred embodiments, an HMW polymer is selected from RG503, PLGA RG 755, PLA R206, PCL/PLA 75:25 and PCL/PLA 25:75.

Preferably, the polymer matrix comprises about 0 wt. % to about 95 wt. % of LMW polymer, preferably about 20 wt. % to about 90 wt. % of LMW polymer, more preferably about 30 wt. % to about 80 wt. % of LMW polymer, and more preferably about 40 wt. % to about 75 wt. % of LMW polymer; about 0 wt. % to about 50 wt. % of HMW polymer, preferably about 5 wt. % to about 40 wt. % of HMW polymer, more preferably about 10 wt. % to about 30 wt. % of HMW polymer, and more preferably about 15 wt. % to about 25 wt. % of HMW polymer; and about 0 wt. % to about 95 wt. % of MMW polymer, preferably about 20 wt. % to about 90 wt. % of MMW polymer, more preferably about 30 wt. % to about 80 wt. % of MMW polymer, and more preferably about 40 wt. % to about 65 wt. % of MMW polymer.

Presently preferred polymers are polylactides, that is, a lactic acid-based polymer that can be based solely on lactic acid or can be a copolymer based on lactic acid, glycolic acid and/or caprolactone-based polymers including caprolactone (CL), which may include small amounts of other comonomers that do not substantially affect the advantageous results, which can be achieved in accordance with the present invention. As used herein, the term "lactic acid" includes the isomers L-lactic acid, D-lactic acid, DL-lactic acid and lactide while the term "glycolic acid" includes glycolide. Most preferred are polymers selected from the group consisting of polylactide polymers, commonly referred to as PLA, poly(lactide-co-glycolide)copolymers, commonly referred to as PLGA, and poly(caprolactone-co-lactic acid) (PCL-co-LA). The polymer may have a monomer ratio of lactic acid/glycolic acid (LG) of from about 50:50 to about 100:0, preferably from about 60:40 to about 85:15, preferably from about 65:35 to about 75:25. In certain embodiments, when the desired duration of release of the beneficial agent is about one month, preferably the polymer has a L/G ratio of 50:50. In alternative embodiments, when the desired duration of release of the beneficial agent is about 2 months, preferably the polymer has an LG ratio of 65:35; when the desired duration of release of the beneficial agent is about 3 months, preferably the polymer has an L/G ratio of 75:25; and when the desired duration of release of the beneficial agent is about 6 months, preferably the polymer has an L/G ratio ranging from about 85:15 to about 100:0.

The poly(caprolactone-co-lactic acid) (PCL-co-LA) polymer has a comonomer ratio of caprolactone/lactic acid (CL/L) of from about 10:90 to about 90:10, from about 50:50; preferably from about 35:65 to about 65:35; and more preferably from about 25:75 to about 75:25. In certain embodiments, the lactic acid based polymer comprises a blend of about 0-90% caprolactone, about 0-100% lactic acid, and about 0-60% glycolic acid.

As indicated in aforementioned U.S. Pat. No. 5,242,910, the polymer can be prepared in accordance with the teachings of U.S. Pat. No. 4,443,340. Alternatively, the lactic acid-based polymer can be prepared directly from lactic acid or a mixture of lactic acid and glycolic acid (with or without a further comonomer) in accordance with the techniques set forth in U.S. Pat. No. 5,310,865. The contents of all of these patents are incorporated by reference. Suitable lactic acid-based polymers are available commercially. The lactic acid-based polymer may be a LMW polymer; a MMW polymer or a HMW polymer or a combination thereof.

Examples of polymers include, but are not limited to, Poly (D,L-lactide-co-glycolide) 50:50 RESOMER® RG502, Poly (D,L-lactide-co-glycolide) 50:50 RESOMER® RG502H, Poly D,L Lactide (RESOMER® R 202, RESOMER® R 203); Poly dioxanone (RESOMER® X 210) (Boehringer Ingelheim Chemicals, Inc., Petersburg, Va.). Additional examples include, but are not limited to, DL-lactide/glycolide 100:0 (MEDISORB® Polymer 100 DL High, MEDISORB® Polymer 100 DL Low); DL-lactide/glycolide 85/15 (MEDISORB® Polymer 8515 DL High, MEDISORB® Polymer 8515 DL Low); DL-lactide/glycolide 75/25 (MEDISORB® Polymer 7525 DL High, MEDISORB® Polymer 7525 DL Low); DL-lactide/glycolide 65/35 (MEDISORB® Polymer 6535 DL High, MEDISORB® Polymer 6535 DL Low); DL-lactide/glycolide 54/46 (MEDISORB® Polymer 5050 DL High, MEDISORB® Polymer 5050 DL Low); and DL-lactide/glycolide 54/46 (MEDISORB® Polymer 5050 DL 2A(3), MEDISORB® Polymer 5050 DL 3A(3), MEDISORB® Polymer 5050 DL 4A(3)) (Medisorb Technologies International L.P., Cincinnati, Ohio); and Poly D,L-lactide-co-glycolide 50:50; Poly D,L-lactide-co-glycolide 65:35; Poly D,L-lactide-co-glycolide 75:25; Poly D,L-lactide-co-glycolide 85:15; Poly DL-lactide; Poly L-lactide; Poly glycolide; Poly ε-caprolactone; Poly DL-lactide-co-caprolactone 25:75; and Poly DL-lactide-co-caprolactone 75:25 (Birmingham Polymers, Inc., Birmingham, Ala.).

The biocompatible polymer is present in the gel composition in an amount ranging from about 5 to about 90% by weight, preferably from about 20 to about 80% by weight, preferably from about 30 to about 75% by weight, often about 35 to about 70% by weight of the viscous gel, and about 40 to about 65% by weight of the viscous gel comprising the combined amounts of the biocompatible polymer and the solvent. The biodegradable, biocompatible lactic acid-based polymer is in an amount comprising about 5 wt. % to about 90 wt. %, and preferably from about 25 wt. % to about 80 wt. %, and more preferably from about 35 wt. % to about 75 wt. %. The solvent will be added to polymer in amounts described below, to provide injectable depot gel compositions.

B. Solvents:

The injectable depot composition of the invention contains a water-immiscible solvent in addition to the bioerodible polymer and the beneficial agent. In preferred embodiments, the compositions described herein are also free of solvents having a miscibility in water that is greater than 7 wt. % at 25° C.

The solvent must be biocompatible, should form a viscous gel with the polymer, and restrict water uptake into the implant. The solvent may be a single solvent or a mixture of solvents exhibiting the foregoing properties. The term "solvent," unless specifically indicated otherwise, means a single solvent or a mixture of solvents. Suitable solvents will substantially restrict the uptake of water by the implant and may be characterized as immiscible in water, i.e., having a solubility in water of less than 7% by weight. Preferably, the solvents are 5 wt. % or less soluble in water; more preferably 3 wt. % or less soluble in water; and even more preferably 1 wt. % or less soluble in water. Most preferably the solubility of the solvent in water is equal to or less than 0.5 wt. %.

Water miscibility may be determined experimentally as follows: Water (1-5 g) is placed in a tared clear container at a controlled temperature, about 20° C., and weighed, and a candidate solvent is added dropwise. The solution is swirled to observe phase separation. When the saturation point appears to be reached, as determined by observation of phase separation, the solution is allowed to stand overnight and is rechecked the following day. If the solution is still saturated, as determined by observation of phase separation, then the percent (w/w) of solvent added is determined. Otherwise more solvent is added and the process is repeated. Solubility or miscibility is determined by dividing the total weight of solvent added by the final weight of the solvent/water mixture. When solvent mixtures are used, for example, 20% triacetin and 80% benzyl benzoate, they are premixed prior to adding to the water.

Solvents useful in this invention are generally less than 7% water soluble by weight as described above. Solvents having the above solubility parameter may be selected from aromatic alcohols, the lower alkyl and aralkyl esters of aryl acids such as benzoic acid, the phthalic acids, salicylic acid, lower alkyl esters of citric acid, such as triethyl citrate and tributyl citrate and the like, and aryl, aralkyl and lower alkyl ketones. Among preferred solvents are those having solubilities within the foregoing range selected from compounds having the following structural formulas (I), (II) and (III).

The aromatic alcohol has the structural formula (I)

Ar—(L)n-OH    (I)

wherein Ar is a substituted or unsubstituted aryl or heteroaryl group, n is zero or 1, and L is a linking moiety. Preferably, Ar is a monocyclic aryl or heteroaryl group, optionally substituted with one or more noninterfering substituents such as hydroxyl, alkoxy, thio, amino, halo, and the like. More preferably, Ar is an unsubstituted 5- or 6-membered aryl or heteroaryl group such as phenyl, cyclopentadienyl, pyridinyl, pyrimadinyl, pyrazinyl, pyrrolyl, pyrazolyl, imidazolyl, furanyl, thiophenyl, thiazolyl, isothiazolyl, or the like. The subscript "n" is zero or 1, meaning that the linking moiety L may or may not be present. Preferably, n is 1 and L is generally a lower alkylene linkage such as methylene or ethylene, wherein the linkage may include heteroatoms such as O, N or S. Most preferably, Ar is phenyl, n is 1, and L is methylene, such that the aromatic alcohol is benzyl alcohol.

The aromatic acid ester or ketone may be selected from the lower alkyl and aralkyl esters of aromatic acids, and aryl and aralkyl ketones. Generally, although not necessarily, the aromatic acid esters and ketones will respectively have the structural formula (II) or (III)

In the ester of formula (II), R1 is substituted or unsubstituted aryl, aralkyl, heteroaryl or heteroaralkyl, preferably substituted or unsubstituted aryl or heteroaryl, more preferably monocyclic or bicyclic aryl or heteroaryl optionally substituted with one or more noninterfering substituents such as hydroxyl, carboxyl, alkoxy, thio, amino, halo, and the like, still more preferably 5- or 6-membered aryl or heteroaryl such as phenyl, cyclopentadienyl, pyridinyl, pyrimadinyl, pyrazinyl, pyrrolyl, pyrazolyl, imidazolyl, furanyl, thiophenyl, thiazolyl, or isothiazolyl, and most preferably 5- or 6-membered aryl. R2 is hydrocarbyl or heteroatom-substituted hydrocarbyl, typically lower alkyl or substituted or unsubstituted aryl, aralkyl, heteroaryl or heteroaralkyl, preferably lower alkyl or substituted or unsubstituted aralkyl or heteroaralkyl, more preferably lower alkyl or monocyclic or bicyclic aralkyl or heteroaralkyl optionally substituted with one or more noninterfering substituents such as hydroxyl, carboxyl, alkoxy, thio, amino, halo, and the like, still more preferably lower alkyl or 5- or 6-membered aralkyl or heteroaralkyl, and most preferably lower alkyl or 5- or 6-membered aryl optionally substituted with one or more additional ester groups having the structure -O-(CO)-R1. Most preferred esters are benzoic acid and phthalic acid derivatives.

In the ketone of formula (III) R3 and R4 may be selected from any of the R1 and R2 groups identified above.

Art recognized benzoic acid derivatives from which solvents having the requisite solubility may be selected include, without limitation: 1,4-cyclohexane dimethanol dibenzoate, diethylene glycol dibenzoate, dipropylene glycol dibenzoate, polypropylene glycol dibenzoate, propylene glycol dibenzoate, diethylene glycol benzoate and dipropylene glycol benzoate blend, polyethylene glycol (200) dibenzoate, isodecyl benzoate, neopentyl glycol dibenzoate, glyceryl tribenzoate, pentaerylthritol tetrabenzoate, cumylphenyl benzoate, trimethyl pentanediol dibenzoate.

Art recognized phthalic acid derivatives from which solvents having the requisite solubility may be selected include: Alkyl benzyl phthalate, bis-cumyl-phenyl isophthalate, dibutoxyethyl phthalate, dimethyl phthalate, diethyl phthalate, dibutyl phthalate, diisobutyl phthalate,butyl octyl phthalate, diisoheptyl phthalate, diisononyl phthalate, nonyl undecyl phthalate, dioctyl phthalate, di-isooctyl phthalate, dicapryl phthalate, mixed alcohol phthalate, di-(2-ethylhexyl) phthalate, linear heptyl nonyl phthalate, linear heptyl nonyl undecyl phthalate, linear nonyl phthalate, linear nonyl undecyl phthalate, linear dinonyl, didecyl phthalate (diisodecyl phthalate), diundecyl phthalate, ditridecyl plithalate, undecyldodecyl phthalate, decyltridecyl phthalate, blend (50/50) of dioctyl and didecyl phthalates, butyl benzyl phthalate, and dicyclohexyl phthalate.

Many of the solvents useful in the invention are available commercially (Aldrich Chemicals, Sigma Chemicals) or may be prepared by conventional esterification of the respective arylalkanoic acids using acid halides, and optionally esterification catalysts, such as described in U.S. Pat. No. 5,556,905, which is incorporated herein by reference, and in the case of ketones, oxidation of their respective secondary alcohol precursors.

Preferred solvents include aromatic alcohols, the lower alkyl and aralkyl esters of the aryl acids described above. Representative acids are benzoic acid and the phthalic acids, such as phthalic acid, isophthalic acid, and terephthalic acid. Most preferred solvents are benzyl alcohol and derivatives of benzoic acid and include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate and benzyl benzoate, with benzyl benzoate being most especially preferred.

The composition may also include, in addition to the water-immiscible solvent(s), one or more additional miscible solvents ("component solvents"), provided that any such additional solvent is other than a lower alkanol. Component solvents compatible and miscible with the primary solvent(s) may have a higher miscibility with water and the resulting mixtures may still exhibit significant restriction of water uptake into the implant. Such mixtures will be referred to as "component solvent mixtures." Useful component solvent mixtures may exhibit solubilities in water greater than the primary solvents themselves, typically between 0.1 wt. % and up to and including 50 wt. %, preferably up to and including 30 wt. %, and most preferably up to and including 10 wt. %, without detrimentally affecting the restriction of water uptake exhibited by the implants of the invention.

Component solvents useful in component solvent mixtures are those solvents that are miscible with the primary solvent or solvent mixture, and include, but are not limited, to triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, glycofurol, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacyclo-heptan-2-one, and mixtures thereof.

Preferred solvent mixtures are those in which benzyl benzoate is the primary solvent, and mixtures formed of benzyl benzoate and either triacetin, tributyl citrate, triethyl citrate or N-methyl-2-pyrrolidone, or glycofurol. Preferred mixtures are those in which benzyl benzoate is present by weight in an amount of 50% or more, more preferably 60% or more and most preferably 80% or more of the total amount of solvent present. Especially preferred mixtures are those of 80:20 mixtures by weight of benzyl benzoate/triacetin and benzyl benzoate/N-methyl-2-pyrrolidone. In additional embodiments, the preferred solvent is benzyl alcohol, and mixtures formed of benzyl alcohol and either benzyl benzoate or ethyl benzoate. Preferred mixtures of benzyl alcohol/benzyl benzoate and benzyl alcohol/ethyl benzoate are 1/99 mixtures by weight; 20/80 mixtures by weight; 30/70 mixtures by weight; 50/50 mixtures by weight; 70/30 mixtures by weight; 80/20 mixtures by weight; 99/1 mixtures by weight. Especially preferred mixtures of benzyl alcohol/benzyl benzoate and benzyl alcohol/ethyl benzoate are 25/75 mixtures by weight and 75/25 mixtures by weight.

The solvent or solvent mixture is typically present in an amount of from about 95 to about 10% by weight, preferably from about 80 to about 20% by weight, preferably from about 70-25% by weight, preferably about 65-30% by weight and often 60-40% by weight of the viscous gel, i.e., the combined amounts of the polymer and the solvent. The polymer to solvent ratio ranges from about 20:80 to about 90:10 by weight; preferably about 30:70 to about 80:20 by weight; preferably about 40:60 to about 75:25 by weight; and more preferably about 45:55 to about 65:35 by weight.

In an especially preferred embodiment, the primary solvent is selected from an aromatic alcohol and lower alkyl and aralkyl esters of benzoic acid and the polymer is a lactic-acid based polymer, most preferably selected from polylactide polymers (PLA), poly(lactide-co-glycolide) copolymers (PLGA), and poly(caprolactone-co-lactic acid) (PCL-co-LA) having a comonomer L/G ratio of about 50:50 to about 100:0 and an L/CL ratio of about 25:75 to about 75:25; and a polymer solvent ratio of about 40:60 to about 65:35. Preferably the polymer has an average molecular weight ranging from about 3,000 to about 120,000; preferably from about 7,000 to about 100,000; more preferably from about 10,000 to about 80,000; and more preferably the polymer has a molecular weight of about 14,000, about 16,000, about 20,000, about 30,000 and about 60,000. Presently, the most preferred solvents are benzyl alcohol, benzyl benzoate and the lower alkyl esters of benzoic acid, e.g., ethyl benzoate. The primary solvents, e.g., aromatic alcohol and benzoic acid esters, may be used alone or in a mixture with other miscible solvents, e.g., triacetin, or thixotropic agents, e.g., ethanol, as described herein.

The solvent or solvent mixture is capable of dissolving the polymer to form a viscous gel that can maintain particles of the beneficial agent dissolved or dispersed and isolated from the environment of use prior to release. The compositions of the present invention provide implants useful both for systemic and local administration of beneficial agent, the implants having a low burst index. Water uptake is controlled by the use of a solvent or component solvent mixture that solubilizes or plasticizes the polymer but substantially restricts uptake of water into implant. Additionally, the preferred compositions may provide viscous gels that have a glass transition temperature that is less than 37° C., such that the gel remains nonrigid for a period of time after implantation of 24 hours or more.

The importance of restriction of water uptake and the appropriate choice of a polymer and a water immiscible solvent for a controlled, sustained delivery over a short duration can be appreciated by reference to FIGS. 6-21 illustrating in vivo release rate profiles for various compositions as a function of time.

In addition to the control of water uptake and associated initial burst by choice of solvent, agents that modulate the water solubility of the beneficial agent can also be utilized in conjunction with the preferred solvents to control burst of beneficial agent from the implant. Burst indices and percent of beneficial agent released in the first twenty-four hours after implantation may be reduced by one-third to two-thirds or more by the use of solubility modulators associated with the beneficial agent. Such modulators are typically coatings, substances that form complexes or otherwise associate with or stabilize the beneficial agent such as metallic ions, other stabilizing agents, waxes, lipids, oils, nonpolar emulsions, and the like. Use of such solubility modulators may permit the use of more highly water soluble solvents or mixtures and achieve burst indices of 8 or less for systemic applications, or with respect to local applications. Typically, the implant systems useful in this invention will release, in the first 2 days after implantation, 60% or less of the total amount of beneficial agent to be delivered to the subject from the implant system, preferably 50% or less, more preferably 40% or less and even more preferably 30% or less.

Limited water uptake by the compositions of this invention can often provide the opportunity to prepare compositions without solubility modulators when in other compositions such modulators would be necessary.

In instances where the choice of solvent and polymer result in compositions severely restricting water uptake by themselves, it may be desirable to add osmotic agents or other agents and hydroattractants that facilitate water uptake to desired levels. Such agents may be, for example, sugars and the like, and are well known in the art.

Limited water uptake by the solvent-polymer compositions of the present invention results in the implant compositions being formed without the finger-like pores in the surface of implants formed using prior art processes. Typically, a composition of the present invention takes the form of a substantially homogeneous, sponge-like gel, with the pores in the interior of the implant being much the same as the pores on the surface of the implant. Compositions of the present invention retain their gel-like consistency and administer a beneficial agent in a controlled manner, at a sustained rate over a short duration of time than do prior art devices. This is possible with the appropriate choice of polymers and water immiscible solvents, and further since the injectable depot gel compositions of the present invention generally have a glass transition temperature, $T_g$, than the body temperature of the subject, e.g., 37° C. for humans. Because of the immiscibility of the solvents that are useful in this invention with water, water uptake by the implant is restricted and the pores that do form tend to resemble a closed cell structure without significant numbers of larger pores or pores extending from the surface into the interior of the implant being open at the surface of the implant. Furthermore, the surface pores offer only a limited opportunity for water from body fluids to enter the implant immediately after implantation, thus controlling the burst effect. Since the compositions often will be highly viscous prior to implantation, when the composition is intended for implantation by injection, the viscosity optionally may be modified by the use of viscosity-reducing, miscible solvents or by the use of emulsifiers, or by heating to obtain a gel composition having a viscosity or shear resistance low enough to permit passage of the gel composition through a needle.

The limit on the amount of beneficial agent released in the first 24 hours that is either desired or required will depend on circumstances such as the overall duration of the delivery period, the therapeutic window for the beneficial agent, potential adverse consequences due to overdosing, cost of beneficial agent, and the type of effect desired, e.g., systemic or local. Preferably, 60% or less of the beneficial agent will be released in the first 2 days after implantation, preferably 50% or less, more preferably 40% or less and even more preferably 30% or less, where the percentage is based on the total amount of beneficial agent to be delivered over the duration of the delivery period.

Depending on the particular solvent or solvent mixture selected, the polymer and beneficial agent and, optionally, solubility modulators of the beneficial agent, the compositions of the present invention intended for systemic delivery may provide a gel composition having a burst index of 8 or less, preferably 6 or less, more preferably 4 or less and most preferably 2 or less. Compositions of PLGA with an average molecular weight ranging from about 3,000 to about 120,000 are desired; preferably from about 7,000 to about 100,000; more preferably from about 10,000 to about 80,000; and more preferably the polymer has a molecular weight of about 14,000 to about 60,000, with solvents having a miscibility in water of less than 7% by weight, optionally combined with the other solvents, providing implants intended for systemic delivery of beneficial agent having a burst index of 10 or less, preferably 7 or less, more preferably 5 or less and most preferably 3 or less, are particularly advantageous. The use of solvent mixtures as discussed herein can be particularly advantageous as a means of providing sufficient plasticizing of the polymer to obtain viscous gel formation and at the same time meet the desired burst indices and percentage release objectives of the compositions of the invention.

Compositions intended for local delivery of beneficial agent are formed in the same manner as those intended for systemic use. However, because local delivery of beneficial agent to a subject will not result in detectable plasma levels of beneficial agent, such systems have to be characterized by percentage of beneficial agent released in a predetermined initial period, rather than a burst index as defined herein. Most typically, that period will be the first 24 hours after implantation and the percentage will be equal to the amount by weight of the beneficial agent released in the period (e.g., 24 hours) divided by the amount by weight of the beneficial agent intended to be delivered in the duration of the delivery period; multiplied by the number 100. Compositions of the present invention will have initial bursts of 40% or less, preferably 30% or less, most preferably 20% or less, for most applications.

In many instances, it may be desirable to reduce the initial burst of beneficial agent during local administration to prevent adverse effects. For example, implants of the invention containing chemotherapeutic agents are suitable for direct injection into tumors. However, many chemotherapeutic agents may exhibit toxic side effects when administered systemically. Consequently, local administration into the tumor may be the treatment method of choice. It is necessary, however, to avoid administration of a large burst of the chemotherapeutic agent if it is possible that such agent would enter the vascular or lymphatic systems where it may exhibit side affects. Accordingly, in such instances, the implantable systems of the present invention having limited burst as described herein are advantageous.

The gel formed by mixing the polymer and the solvent typically exhibits a viscosity of from about 100 to about 50,000 poise, preferably from about 500 to about 30,000 poise, more preferably from about 500 to about 10,000 poise measured at a $1.0 \sec^{-1}$ shear rate and 25° C. using a Haake Rheometer at about 1-2 days after mixing is completed. Mixing the polymer with the solvent can be achieved with conventional low shear equipment such as a Ross double planetary mixer for from about 10 minutes to about 1 hour, although shorter and longer periods may be chosen by one skilled in the art depending on the particular physical characteristics of the composition being prepared. Since the depot gel composition of the invention is administered as an injectable composition, a countervailing consideration when forming depot gel compositions that are viscous gels is that the polymer/solvent/beneficial agent composition have sufficiently low viscosity in order to permit it to be forced through a small diameter, e.g., 18- to 20-gauge needle. If necessary, adjustment of viscosity of the gel for injection can be accomplished with emulsifying agents as described herein. Yet, such compositions should have adequate dimensional stability so as to remain localized and be able to be removed if necessary. The particular gel or gel-like compositions of the present invention satisfy such requirements.

If the polymer composition is to be administered as an injectable gel, the level of polymer dissolution will need to be balanced with the resulting gel viscosity, to permit a reasonable force to dispense the viscous gel from a needle or a catheter, and the potential burst effect. Highly viscous gels enable the beneficial agent to be delivered without exhibiting a significant burst effect, but may make it difficult to dispense the gel through a needle or a catheter. In those instances, an emulsifying agent may optionally be added to the composition. Also, since the viscosity may generally be lowered as the temperature of the composition increases, it may be advantageous in certain applications to reduce the viscosity of the gel by heating to provide a more readily injectable composition. The shear thinning characteristics of the depot gel compositions of the present invention allow them to be readily injected into an animal, including humans, using standard gauge needles or catheters without requiring undue dispensing pressure.

When the emulsifying agent is mixed with the viscous gel formed from the polymer and the solvent using conventional static or mechanical mixing devices, such as an orifice mixer, the emulsifying agent forms a separate phase composed of dispersed droplets of microscopic size that typically have an average diameter of less than about 100 microns. The continuous phase is formed of the polymer and the solvent. The particles of the beneficial agent may be dissolved or dispersed in either the continuous phase or the droplet phase. In the resulting thixotropic composition, the droplets of emulsifying agent elongate in the direction of shear and substantially decrease the viscosity of the viscous gel formed from the polymer and the solvent. For instance, with a viscous gel having a viscosity of from about 5,000 to about 50,000 poise measured at $1.0 \sec^{-1}$ at 25° C., one can obtain a reduction in viscosity to less than 100 poise when emulsified with a 10% ethanol/water solution at 25° C. as determined by Haake Rheometer.

When used, the emulsifying agent typically is present in an amount ranging from about 5 to about 80%, preferably from about 20 to about 60% and often 30 to 50% by weight based on the amount of the injectable depot gel composition that is the combined amounts of polymer, solvent, emulsifying agent and beneficial agent. Emulsifying agents include, for example, solvents that are not fully miscible with the polymer solvent or solvent mixture. Illustrative emulsifying agents are water, alcohols, polyols, esters, carboxylic acids, ketones, aldehydes and mixtures thereof. Preferred emulsifying agents are alcohols, propylene glycol, ethylene glycol, glycerol, water, and solutions and mixtures thereof. Especially preferred are water, ethanol, and isopropyl alcohol and solutions and mixtures thereof. The type of emulsifying agent affects the size of the dispersed droplets. For instance, ethanol will provide droplets that have average diameters that can be on the order of ten times larger than the droplets obtained with an isotonic saline solution containing 0.9% by weight of sodium chloride at 21° C.

It is to be understood that the emulsifying agent does not constitute a mere diluent that reduces viscosity by simply decreasing the concentration of the components of the composition. The use of conventional diluents can reduce viscosity, but can also cause the burst effect mentioned previously when the diluted composition is injected. In contrast, the injectable depot composition of the present invention can be formulated to avoid the burst effect by selecting the appropriate polymer, the solvent and emulsifying agent so that once injected into place, the emulsifying agent has little impact on the release properties of the original system.

Although the injectable depot gel composition of the present invention preferably is formed as viscous gels, the means of administration of the implants is not limited to injection, although that mode of delivery may often be preferred. Where the injectable depot gel composition will be administered as a leave-behind product, it may be formed to fit into a body cavity existing after completion of surgery or it may be applied as a flowable gel by brushing or palleting the gel onto residual tissue or bone. Such applications may permit loading of beneficial agent in the gel above concentrations typically present with injectable compositions.

C. Beneficial Agents:

The beneficial agent can be any physiologically or pharmacologically active substance or substances optionally in combination with pharmaceutically acceptable carriers and additional ingredients such as antioxidants, stabilizing agents, permeation enhancers, etc., that do not substantially adversely affect the advantageous results that can be attained by the present invention. The beneficial agent may be any of the agents which are known to be delivered to the body of a human or an animal and that are preferentially soluble in water rather than in the polymer-dissolving solvent. These agents include drug agents, medicaments, vitamins, nutrients, or the like. Included among the types of agents which meet this description are lower molecular weight compounds, proteins, peptides, genetic material, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by the composition of the present invention include, but are not limited to bupivacaine, buprenorphine, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranifrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives, such as betamethasone, triamcinolone, methyltestosterone, testosterone, 17-S-estradiol, ethinyl estradiol, ethinyl estradiol 3-methyl ether, prednisolone, 17α-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinopril, enalapril, enalaprilat, captopril, ramipril, famotidine, nizatidine, sucralfate, etintidine, tetratolol, minoxidil, chlordiazepoxide, amitriptyline, paliperidone, resperidone, octreotide, alendronate, $\alpha$-4,$\beta^{-7}$ receptor antagonist leukocyte and infliximab (REMICADE® ). Further examples are proteins and peptides which include, but are not limited to, bone morphogenic proteins, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons such as interferon alpha-2a, interferon alpha-2b, and consensus interferon, interleukins, growth hormones such as human growth hormone and its derivatives such as methione-human growth hormone and des-phenylalanine human growth hormone, parathyroid hormone, bovine growth hormone and porcine growth hormone, fertility inhibitors such as the prostaglandins, fertility promoters, growth factors such as epidermal growth factors (EGF), platelet-derived growth factors (PDGF), fibro-blast growth factors (FGF), transforming growth factors-$\alpha$ (TGF-$\alpha$), transforming growth factors-$\beta$ (TGF-$\beta$), erythropoietin (EPO), insulin-like growth factor-I-(IGF-I), insulin-like growth factor-II (IGF-II), interleukin-1, interleukin-2, interleukin-6, interleukin-8, tumor necrosis factor-$\alpha$ (TNF-$\alpha$), tumor necrosis factor-$\beta$ (TNF$\beta$), Interferon-$\alpha$ (INF-$\alpha$), Interferon-$\beta$ (INF-$\beta$), Interferon-$\gamma$ (INF-$\gamma$), Interferon-$\omega$ (INF-$\omega$), colony stimulating factors (CSF), vascular cell growth factor (VEGF), thrombopoietin (TPO), stromal cell-derived factors (SDF), placenta growth factor (PIGF), hepatocyte growth factor (HGF), granulocyte macrophage colony stimulating factor (GM-CSF), glial-derived neurotropin factor (GDNF), granulocyte colony stimulating factor (G-CSF), ciliary neurotropic factor (CNTF), bone growth factor, transforming growth factor, bone morphogeneic proteins (BMP), coagulation factors, human pancreas hormone releasing factor, analogs and derivatives of these compounds, and pharmaceutically acceptable salts of these compounds, or their analogs or derivatives.

The present invention also finds application with chemotherapeutic agents for the local application of such agents to avoid or minimize systemic side effects. Gels of the present invention containing chemotherapeutic agents may be injected directly into the tumor tissue for sustained delivery of the chemotherapeutic agent over time. In some cases, particularly after resection of the tumor, the gel may be implanted directly into the resulting cavity or may be applied to the remaining tissue as a coating. In cases in which the gel is implanted after surgery, it is possible to utilize gels having higher viscosities since they do not have to pass through a small diameter needle. Representative chemotherapeutic agents that may be delivered in accordance with the practice of the present invention include, for example, carboplatin, cisplatin, paclitaxel, 5-fluorouracil, BCNU, vincristine, camptothecin, etopside, cytokines, ribozymes, interferons, oligonucleotides and oligonucleotide sequences that inhibit translation or transcription of tumor genes, functional derivatives of the foregoing, and generally known chemotherapeutic agents such as those described in U.S. Pat. No. 5,651,986. The present application has particular utility in the sustained delivery of water soluble chemotherapeutic agents, such as, for example, cisplatin and carboplatin and the water soluble derivatives of paclitaxel. Those characteristics of the invention that minimize the burst effect are particularly advantageous in the administration of water soluble beneficial agents of all kinds, but particularly those compounds that are clinically useful and effective but may have adverse side effects.

To the extent not mentioned above, the beneficial agents described in aforementioned U.S. Pat. No. 5,242,910 can also be used. One particular advantage of the present invention is that materials, such as proteins, as exemplified by the enzyme lysozyme, and cDNA, and DNA incorporated into vectors both viral and nonviral, which are difficult to microencapsulate or process into microspheres can be incorporated into the compositions of the present invention without the level of degradation caused by exposure to high temperatures and denaturing solvents often present in other processing techniques.

The beneficial agent is preferably incorporated into the viscous gel formed from the polymer and the solvent in the form of particles typically having an average particle size of from about 0.1 to about 250 microns, preferably from about 1 to about 125 microns and often from 10 to 90 microns. For instance, particles having an average particle size of about 5 microns have been produced by spray drying or freeze drying an aqueous mixture containing 50% sucrose and 50% chicken lysozyme (on a dry weight basis) and mixtures of 10-20% hGH and 15-30 mM zinc acetate. Such particles have been used in certain of the examples illustrated in the figures. Conventional lyophilization processes can also be utilized to form particles of beneficial agents of varying sizes using appropriate freezing and drying cycles, followed by appropriate grounding and sieving.

To form a suspension or dispersion of particles of the beneficial agent in the viscous gel formed from the polymer and the solvent, any conventional low shear device can be used such as a Ross double planetary mixer at ambient conditions. In this manner, efficient distribution of the beneficial agent can be achieved substantially without degrading the beneficial agent.

The beneficial agent is typically dissolved or dispersed in the composition in an amount of from about 0.1 to about 70% by weight, preferably in an amount of from about 0.5 to about 50% and often 1 to 30% by weight of the combined amounts of the polymer, solvent and beneficial agent. Depending on the amount of beneficial agent present in the composition, one can obtain different release profiles and burst indices. More specifically, for a given polymer and solvent, by adjusting the amount of these components and the amount of the beneficial agent, one can obtain a release profile that depends more on the degradation of the polymer than the diffusion of the beneficial agent from the composition or vice versa. In general, during the early stages, the release rate profile is generally controlled by the rate of diffusion and the rate of dissolution of the beneficial agent from the composition; while in the later stages, polymer degradation is the major factor in determining the release rate profiles. In this respect, at lower beneficial agent loading level, the release profile depends primarily on the rate of degradation of the polymer, and secondarily on the diffusion of the beneficial agent from the composition, wherein generally the release rate increases or is constant (e.g., flat profile) with time.

At higher beneficial agent loading levels, the release rate depends on the solubility of the beneficial agent in the depot gel composition or surrounding medium. For example, if the beneficial agent has the high solubility in the composition or surrounding medium, the release profile depends primarily on the rate of diffusion of the beneficial agent from the composition and secondarily on the rate of polymer degradation, wherein generally the release rate decreases with time. If the beneficial agent has very low solubility in the composition or surrounding medium, the release profile depends primarily on the rate of diffusion and the rate of dissolution of the beneficial agent from the composition, and secondarily on the rate of polymer degradation, wherein generally the release rate is constant with time.

At intermediate beneficial agent loading levels, the release rate depends on the combined effects of diffusion of the beneficial agent from the composition and the rate of polymer degradation, wherein this combined effect can be tailored to achieve a substantially constant release rate profile. In order to minimize burst, loading of beneficial agent on the order of 30% or less by weight of the overall gel composition, i.e., polymer, solvent and beneficial agent, is preferred, and loading of 20% or less is more preferred.

Release rates and loading of beneficial agent will be adjusted to provide for therapeutically effective delivery of the beneficial agent over the intended sustained delivery period. Preferably, the beneficial agent will be present in the polymer gel at concentrations that are above the saturation concentration of beneficial agent in water to provide a drug reservoir from which the beneficial agent is dispensed. While the release rate of beneficial agent depends on the particular circumstances, such as the beneficial agent to be administered, release rates on the order of from about 0.1 to about 10,000 micrograms/day, preferably from about 1 to about 5,000 micrograms per day, for periods of from about 2 weeks to about one year can be obtained. Greater amounts may be delivered if delivery is to occur over shorter periods. Generally, a higher release rate is possible if a greater burst can be tolerated. In instances where the gel composition is surgically implanted, or used as a "leave behind" depot when surgery to treat the disease state or another condition is concurrently conducted, it is possible to provide higher doses than would normally be administered if the implant was injected. Further, the dose of beneficial agent may be controlled by adjusting the volume of the gel implanted or the injectable gel injected.

FIGS. 6A-6D and 7-21 illustrate representative release profiles of various beneficial agents obtained in rats from preferred compositions of this invention. As illustrated in the figures, the injectable depot gel formulations of the invention comprising polymers provide a controlled, sustained release of a beneficial agent over a specified/desired duration of time. The duration and the release rate profiles can be adjusted depending on the nature of the polymer and the properties of the polymer (e.g., MW, comonomer ratios, end-group); and the nature of the solvent and the polymer/solvent ratio.

D. Optional Additional Components:

Other components may be present in the injectable depot gel composition, to the extent they are desired or provide useful properties to the composition, such as polyethylene glycol, hydroscopic agents, stabilizing agents, pore forming agents, thixotropic agents and others. When the composition includes a peptide or a protein that is soluble in or unstable in an aqueous environment, it may be highly desirable to include a solubility modulator that may, for example, be a stabilizing agent, in the composition. Various modulating agents are described in U.S. Pat. Nos. 5,654,010 and 5,656,297, which are incorporated herein by reference. In the case of hGH, for example, it is preferable to include an amount of a salt of a divalent metal, preferably zinc. Examples of such modulators and stabilizing agents, which may form complexes with the beneficial agent or associate to provide the stabilizing or modulated release effect, include metal cations, preferably divalent, present in the composition as magnesium carbonate, zinc carbonate, calcium carbonate, magnesium acetate, magnesium sulfate, zinc acetate, zinc sulfate, zinc chloride, magnesium chloride, magnesium oxide, magnesium hydroxide, other antacids, and the like. The amounts of such agents used will depend on the nature of the complex formed, if any, or the nature of the association between the beneficial agent and the agent. Molar ratios of solubility modulator or stabilizing agent to beneficial agent of about 100:1 to 1:1, preferably 10:1 to 1:1, typically can be utilized.

The thixotropic agent, i.e., an agent that imparts thixotropic properties to the polymer gel, is selected from the lower alkanols. Lower alkanol means an alcohol that contains 2-6 carbon atoms and is straight chain or branched chain. Such alcohols may be exemplified by ethanol, isopropanol, and the like. Importantly, such a thixotropic agent is not a polymer solvent. (See, e.g., Development of an in situ forming biodegradable poly-lactide-co-glycolide system for controlled release of proteins, Lambert, W. J., and Peck, K. D., Journal of Controlled Release, 33 (1995) 189-195).

Pore forming agents include biocompatible materials that when contacted with body fluids dissolve, disperse or degrade to create pores or channels in the polymer matrix. Typically, organic and nonorganic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxymethylcellulose, hydroxypropylcellulose, and the like) can conveniently be used as pore formers. Such materials may be present in amounts varying from about 0.1% to about 100% of the weight of the polymer, but will typically be less than 50% and more typically less than 10-20% of the weight of polymer.

II. Utility and Administration:

The means of administration of the depot gel compositions is not limited to injection, although that mode of delivery may often be preferred. Where the depot gel composition will be administered as a leave-behind product, it may be formed to fit into a body cavity existing after completion of surgery or it may be applied as a flowable gel by brushing or palleting the gel onto residual tissue or bone. Such applications may permit loading of beneficial agent in the gel above concentrations typically present with injectable compositions.

Compositions of this invention without beneficial agent are useful for wound healing, bone repair and other structural support purposes.

To further understand the various aspects of the present invention, the results set forth in the previously described figures were obtained in accordance with the following examples.

EXAMPLE 1

Depot Vehicle Preparation

A gel vehicle for use in an injectable depot of the composition was prepared as follows. A glass vessel was tared on a Mettler AE 163 analytical balance or a Mettler PJ3000 top loader balance. Poly (D,L-lactide-co-glycolide) (PLGA), (L/G ratio of 50/50) with an inherent viscosity of 0.15 (PLGA-BPI, Birmingham Polymers, Inc., Birmingham, Ala.); RESOMER® PLGA RG502 (L/G ratio of 50/50), RESOMER® PLGA RG503 (L/G ratio of 50/50); 50:50 RESOMER® RG504 (PLGARG 504); or a Poly (D,L-lactide-co-glycolide) (PLGA) (L/G ratio of 75/25, RESOMER® RG752 (Boehringer Ingelheim Chemicals Inc., Petersburg, Va.), were milled and sieved below 425 microns. The polymer was weighed into the glass vessel. The glass vessel containing the polymer was tared and the corresponding solvent was added. Amounts expressed as percentages for various polymer/solvent combinations are set forth in Table 1, below. The polymer/solvent mixture was stirred at 250±50 rpm (IKA electric stirrer, IKH-Werke GmbH and Co., Stanfen, Germany) for about 5 to 10 minutes, resulting in a sticky paste-like substance containing polymer particles. The vessel containing the polymer/solvent mixture was sealed and placed in a temperature-controlled incubator equilibrated to 37° C. for 1 to 4 days, with intermittent stirring, depending on the type and/or amount of solvent and polymer. The polymer/solvent mixture was removed from the incubator when it appeared to be a clear amber homogeneous solution. Thereafter, the mixture was placed in an oven (65° C., 30 minutes) until polymer was dissolved in the mixture.

Additional depot gel vehicles are prepared with the following solvents or mixtures of solvents: benzyl benzoate ("BB"), benzyl alcohol ("BA"), ethyl benzoate ("EB"), ethanol, and propylene glycol ("PG"), and mixtures thereof and the following polymers: Poly (D,L-lactide-co-glycolide) 75:25 (RESOMER® RG752), Poly (D,L-lactide-co-glycolide) 75:25 (RESOMER® RG755), Poly (D,L-lactide-co-glycolide) 75:25 (RESOMER® RG756), Poly (D,L-lactide-co-glycolide) 85:15 (RESOMER® RG858), Poly (D,L-lactide) (RESOMER® R104), Poly (D,L-lactide) (RESOMER® R202), Poly (D,L-lactide) (RESOMER® R202H), Poly (D,L-lactide) (RESOMER® R203), Poly (D,L-lactide) (RESOMER® R206), Poly (D,L-lactide) (RESOMER® R207), Poly (D,L-lactide) (RESOMER® R208), Poly L-Lactide-co-D,L-lactide 90:10 (RESOMER® LR 209); Poly (D,L-lactide-co-glycolide) 50:50 RESOMER® RG502; Poly (D,L-lactide-co-glycolide) 50:50 RESOMER® RG502H, PLGA-502H; Poly (D,L-lactide-co-glycolide) 50:50 RESOMER® RG503, PLGA-503; Poly (D,L-lactide-co-glycolide) 50:50 RESOMER® RG755, PLGA-755; Poly (L-lactide) (RESOMER® L104), Poly (L-lactide) (RESOMER® L206), Poly (L-lactide) (RESOMER® L207), Poly (L-lactide) (RESOMER® L209), Poly (L-lactide) (RESOMER® L210), Poly (L-lactide) (RESOMER® L214), Poly D-L-lactide-co-glycolide 75:25 (RESOMER® RG 752, RESOMER® RG 756); Poly D,L-lactide-co-glycolide 85:15 (RESOMER® RG 858); Poly L-lactide-co-trimethylene carbonate 70:30 (RESOMER® LT 706); Poly dioxanone (RESOMER® X 210) (Boehringer Ingelheim Chemicals, Inc., Petersburg, Va.); Poly (L-lactide-co-D,L-lactide) 70:30 (RESOMER® LR708), Poly (L-Lactide-co-D,L-lactide) 90:10 (RESOMER® LR 209), Poly(D,L-lactide) (MEDISORB® Polymer 100 DL High, MEDISORB® Polymer 100 DL Low); Poly(D,L-lactide-co-glycolide) 85:15 (MEDISORB® Polymer 8515 DL High, MEDISORB® Polymer 8515 DL Low), Poly(D,L-lactide-co-glycolide) 75:25 (MEDISORB® Polymer 7525 DL High, MEDISORB® Polymer 7525 DL Low), Poly(D,L-lactide-co-glycolide) 65:35 (MEDISORB® Polymer 6535 DL High, MEDISORB® Polymer 6535 DL Low), DL-lactide/glycolide 54/46 (MEDISORB® Polymer 5050 DL High, MEDISORB® Polymer 5050 DL-Low); and DL-lactide/glycolide 54/46 (MEDISORB® Polymer 5050 DL 2A(3), MEDISORB® Polymer 5050 DL 3A(3), MEDISORB° Polymer 5050 DL 4A(3)) (Medisorb Technologies International L.P., Cincinnati, Ohio); and Poly D,L-lactide-co-glycolide 50:50; Poly D,L-lactide-co-glycolide 65:35; Poly (D,L-lactide-co-glycolide) 65:35 (Birmingham Polymers, Inc., Birmingham, Ala.); Poly (D,L-lactide-co-glycolide) 75:25 (Birmingham Polymers, Inc., Birmingham, Ala.); Poly (D,L-lactide-co-glycolide) 85:15 (Birmingham Polymers, Inc., Birmingham, Ala.); Poly D,L-lactide (Birmingham Polymers, Inc., Birmingham, Ala.); Poly L-lactide (Birmingham Polymers, Inc., Birmingham, Ala.); Poly glycolide; Poly ε-caprolactone; Poly (D,L-lactide-co-caprolactone) 25:75 (Birmingham Polymers, Inc., Birmingham, Ala.); and Poly (D,L-lactide-co-caprolactone) 75:25 (Birmingham Polymers, Inc., Birmingham, Ala.). Representative gel vehicles are described in Tables 1-3 below.

TABLE 1

| Formulation | PLGA (wt %) | BB (wt %) | BA (wt %) |
|---|---|---|---|
| 1 | 50[1a] | 50 | — |
| 2 | 50[1a] | 37.5 | 12.5 |
| 3 | 30[1b] | 70 | — |
| 4 | 30[1b] | 52.5 | 17.5 |
| 5 | 40[1b] | 60 | — |
| 6 | 40[1b] | 45 | 15 |
| 7 | 20[1c] | 80 | — |
| 8 | 20[1c] | 60 | 20 |
| 9 | 30[1c] | 70 | — |
| 10 | 30[1c] | 52.5 | 17.5 |

[1a]= PLGA RG752;
[1b]= PLGA RG755; and
[1c]= PLGA RG756.

TABLE 2

| Formulation | PLGA RG503[2a] (wt %) | PLGA RG502[2b] (wt %) | LMW PLGA[2c] (wt %) | Benzyl Benzoate (wt %) | Benzyl Alcohol (wt %) |
|---|---|---|---|---|---|
| 11[2d] | 0 | 45 | 0 | 45 | 0 |
| 12[2d] | 9.5 | 0 | 35.5 | 45 | 0 |

[2a]High Molecular Weight (HMW) PLGA (RG 503), MW = 38,000;
[2b]Medium Molecular Weight (MMW) PLGA RG 502, MW = 16,000;
[2c]Low Molecular Weight (LMW) PLGA, MW = 8,000; and
[2d]10% drug loading.

TABLE 3

| Formulation | Polymer PLGA-RG502 (%) | Benzyl Benzoate (%) | Ethanol (%) |
|---|---|---|---|
| 13 | 50 | 50 | 0 |
| 14 | 50 | 47.5 | 2.5 |
| 15 | 50 | 45 | 5 |
| 16 | 50 | 42.5 | 7.5 |

EXAMPLE 2 hGH Particle Preparation

Human growth hormone (hGH) particles (optionally containing zinc acetate) were prepared as follows: hGH solution (5 mg/ml) solution in water (BresaGen Corporation, Adelaide, Australia) was concentrated to 10 mg/mL using a Concentration Dialysis Selector diafiltering apparatus. The diafiltered hGH solution was washed with 5 times volume of tris or phosphate buffer solution (pH 7.6) Particles of hGH were then formed by spray drying or lyophilization using conventional techniques. Phosphate buffer solutions (5 or 50 mM) containing hGH (5 mg/mL) and optionally various levels of zinc acetate (0 to 30 mM) when ZN complexed particles were prepared) were spray-dried using a Yamato Mini Spray dryer set at the following parameters:

| Spray Dryer Parameter | Setting |
|---|---|
| Atomizing Air | 2 psi |
| Inlet Temperature | 120° C. |
| Aspirator Dial | 7.5 |
| Solution Pump | 2-4 |
| Main Air Valve | 40-45 psi |

Lyophilized particles were prepared from tris buffer solutions (5 or 50 mM: pH 7.6) containing hGH (5 mg/mL) using a Durastop μP Lyophilizer in accordance with the following freezing and drying cycles:

| Freezing cycle | Ramp down at 2.5° C./min to −30° C. and hold for 30 min |
| | Ramp down at 2.5° C./min to −30° C. and hold for 30 min |
| Drying cycle | Ramp up at 0.5° C./min to 10° C. and hold for 960 min |
| | Ramp up at 0.5° C./min to 20° C. and hold for 480 min |
| | Ramp up at 0.5° C./min to 25° C. and hold for 300 min |
| | Ramp up at 0.5° C./min to 30° C. and hold for 300 min |
| | Ramp up at 0.5° C./min to 5° C. and hold for 5,000 min |

EXAMPLE 3 hGH-Stearic Acid Particle Preparation

Human growth hormone (hGH) particles were prepared as follows: Lyophilized hGH (3.22 grams, Pharmacia-Upjohn, Stockholm, Sweden) and stearic acid (3.22 grams, 95% pure, Sigma-Aldrich Corporation, St. Louis, Mo.) were blended and ground. The ground material was compressed in a 13-mm round die, with a force of 10,000 pounds for 5 minutes. Compressed tablets were ground and sieved through a 70-mesh screen followed by a 400 mesh screen to obtain particles having a size range between 38 and 212 microns.

EXAMPLE 4

Bupivacaine Base Preparation

Bupivacaine hydrochloride (Sigma-Aldrich Corporation, St. Louis, Mo.) was dissolved in deionized (DI) water at a concentration of 40 mg/ml (saturation). A calculated amount of sodium hydroxide (in the form of 1 N solution) was added to the solution and the pH of the final mixture was adjusted to 10 to precipitate the Bupivacaine base. The precipitated product was filtered, and further washed with DI water at least three times. The precipitated product was dried at ca. 40° C. in vacuum for 24 hours.

EXAMPLE 5

Bupivacaine Particle Preparation

Bupivacaine drug particles (both base and hydrochloride salt) were prepared as follows. Bupivacaine hydrochloride (Sigma-Aldrich Corporation, St. Louis, Mo.) or bupivacaine base prepared according to Example 4 were grounded and then sieved to a fixed range using 3-inch stainless steel sieves. Typical ranges include 25 μm to 38 μm, 38 μm to 63 μm, and 63 μm to 125 μm.

EXAMPLE 6

Bupivacaine-Stearic Acid Particle Preparation

Bupivacaine particles were prepared as follows: Bupivacaine hydrochloride (100 grams, Sigma-Aldrich Corporation, St. Louis, Mo.) was grounded and sieved through 63-125 micron sieves. The bupivacaine particles and stearic acid (100 grams, 95% pure, Sigma-Aldrich Corporation, St. Louis, Mo.) were blended and ground. The ground material was compressed in a 13-mm round die, with a force of 5,000 pounds for 5 minutes. Compressed tablets were ground and sieved through a 120-mesh screen followed by a 230-mesh screen to obtain particles having a size range between 63-125 microns.

EXAMPLE 7

Preparation of Leuprolide Acetate Particles

Leuprolide acetate (Mallinckrodt Inc., St. Louis, Mo.) was ground and sieved between 63-125 μm sieves (for nominal particle size of-90 μm). A GILSON digital Sieve Shaker may be employed to speed the sieving (Gilson Company Inc., Worthington, Ohio).

EXAMPLE 8

Preparation of Leuprolide Acetate-Stearic Acid Particles

Stearic acid (95% pure, Sigma-Aldrich Corporation, St. Louis, Mo.) was passed through a 120-mesh screen (125 μm). Equal amounts of milled leuprolide acetate (<63 μm, prepared as described in Example 2 above) and sieved stearic acid were transferred to the Waring blender and blended for 30 seconds. The blended materials were compressed in a 13-mm round die using a compression force of 5,000 lbs and hold time of 5 mm. Compressed pellets were ground and sieved through a 120-mesh (125 μm) sieve and retained on a 230-mesh (63 μm) sieve.

EXAMPLE 9

Preparation of Buprenorphine Particles

Buprenorphine hydrochloride (100 grams, Sigma-Aldrich Corporation, St. Louis, Mo.) was ground and sieved through preselected sieves such as 25, 38, 62 or 125 micron sieves depending on the desirable particle sizes to obtain the corresponding Buprenorphine particles.

EXAMPLE 10

Preparation of Buprenorphine-Stearic Acid Particles

Equal amounts of Buprenorphine particles (prepared as described in Example 4) above) and stearic acid (prepared as described in Example 3) were blended and ground. The ground material was compressed in a 13-mm round die, with a force of 5,000 pounds for 5 minutes. Compressed tablets were ground and sieved through a 120-mesh screen followed by a 230-mesh screen to obtain particles having a size range between 63-125 microns.

EXAMPLE 11

Drug Loading

Compressed particles comprising beneficial agent with or without stearic acid prepared as above were added to a gel vehicle in an amount of 5-30% by weight and blended manually until the dry powder was wetted completely. Then, the milky light yellow particle/gel mixture was thoroughly blended by conventional mixing using a Caframo mechanical stirrer with an attached square-tip metal spatula. Resulting formulations are illustrated in Tables 4-12 below. Final homogenous gel formulations were transferred to 3, 10 or 30 cc disposable syringes for storage or dispensing.

TABLE 4

| Formulation | PLGA RG502[4a] (wt %) | LMW PLGA (wt %) | Benzyl Benzoate (wt %) |
|---|---|---|---|
| 17[4c] | 45 | 0[4b] | 45 |
| 18[4c] | 0 | 45[4b] | 45 |
| 19[4d] | 45 | 0[4b] | 45 |
| 20[4d] | 0 | 45[4b] | 45 |
| 21[4f] | 45 | 0[4e] | 45 |
| 22[4f] | 0 | 45[4e] | 45 |
| 23[4f] | 0 | 63[4e] | 27 |

[4a]= PLGA RG 502, MW = 16,000.
[4b]= Low Molecular Weight (LMW, MW = 8,000) PLGA with an ester end group.
[4c]= 10% bupivacaine hydrochloride loading.
[4d]= 10% bupivacaine base loading.
[4e]= Low Molecular Weight (LMW, MW - 7,000) PLGA with an ester end group
[4f]= 5% hGH loading.

TABLE 5

| Formulation | LMW PLGA[5g] (wt %) | LMW PLGAc[5h] (wt %) | Benzyl Benzoate (wt %) | Benzyl Alcohol (wt %) |
|---|---|---|---|---|
| 24[5i] | 58.5 | 0 | 31.5 | 0 |
| 25[5i] | 58.5 | 0 | 0 | 31.5 |
| 26[5i] | 67.5 | 0 | 0 | 22.5 |
| 27[5i] | 0 | 67.5 | 0 | 22.5 |
| 28[5j] | 0 | 60 | | 20 |

[5g]= Low Molecular Weight (LMW, MW = 8,000) PLGA with an ester end group.
[5h]= Low Molecular Weight (LMW, MW = 10,000) PLGA with a carboxyl end group.
[5i]= 10% bupivacaine hydrochloride loading
[5j]= 10% bupivacaine hydrochloride and 10% SA loading.

TABLE 6

| Formulation | Polymer[6a] (%) | Benzyl Benzoate (%) | Ethanol (%) |
|---|---|---|---|
| 29[6b] | 45.0 | 45.0 | 0.0 |
| 30[6c] | 40.0 | 40.0 | 0.0 |
| 31[6c] | 45.0 | 44.0 | 1.0 |
| 32[6c] | 39.0 | 39.0 | 2.7 |
| 33[6b] | 39.0 | 39.7 | 0.0 |
| 34[6c] | 31.9 | 47.6 | 0.3 |
| 35[6c] | 33.5 | 44.0 | 0.3 |
| 36[6c] | 40.2 | 36.0 | 0.9 |
| 37[6c] | 32.4 | 44.2 | 1.2 |
| 38[6c] | 32.3 | 44.0 | 1.3 |
| 39[6c] | 36.2 | 39.6 | 1.5 |

TABLE 6-continued

| Formulation | Polymer[6a] (%) | Benzyl Benzoate (%) | Ethanol (%) |
|---|---|---|---|
| 40[6c] | 32.9 | 40.1 | 1.9 |
| 41[6d] | 35.3 | 45.8 | 0.9 |

[6a]= PLGA - 502 Polymer;
[6b]= 10% particle loading (2.8% hGH, 5% stearic acid);
[6c]= 20% particle loading (5% hGH, 10% stearic acid);
[6d]= 15% particle loading (5% hGH, 7% stearic acid).

TABLE 7

| Formulation | PLGA RG752 (wt %) | PLGA RG755 (wt %) | BB (wt %) | BA (wt %) | EtOH (wt %) |
|---|---|---|---|---|---|
| 42[7a] | 48.6 | — | 39.8 | — | — |
| 43[7a] | 48.6 | — | 29.8 | 10.0 | — |
| 44[7a] | 24.3 | 24.3 | 29.8 | 10.0 | — |
| 45[7a] | 48.6 | — | 35.8 | — | 4.0 |

[7a]= 5 wt. % leuprolide acetate loaded.

TABLE 8

| Formulation | PLGA RG752 (wt %) | PLC (wt %) | BB (wt %) | BA (wt %) | EtOH (wt %) |
|---|---|---|---|---|---|
| 46[8a] | 24.3 | 24.3 | 29.8 | 10.0 | — |
| 47[8a] | 57.6 | — | — | 31.0 | — |
| 48[8a] | 28.8 | 28.8 | 20.1 | 7.8 | 3.1 |

[8a]= 5 wt. % leuprolide acetate loaded.

TABLE 9

| Formulation | PLGA RG752 (wt %) | PLC (wt %) | BB (wt %) |
|---|---|---|---|
| 49[9a] | 48.6 | — | 39.8 |
| 50[9a] | — | 48.6 | 39.8 |

[9a]= 10 wt. % leuprolide acetate loaded without stearic acid in the drug particle formulations.

TABLE 10

| Formulation | P(DL)LA R202 (wt %) | BB (wt %) |
|---|---|---|
| 51[10a] | 53.1 | 35.4 |
| 52[10a] | 57.6 | 31.0 |
| 53[10b] | 3 Month LUPRON DEPOT ® | |

[10a]= 5 wt. % leuprolide acetate loaded;
[10b]= 3-month Lupron Depot ®.

TABLE 11

| Formulation | PLGA RG752 (wt %) | BB (wt %) | BA (wt %) |
|---|---|---|---|
| 54[11a,b] | 50.6 | 41.4 | — |
| 55[11a,b] | 50.6 | — | 41.4 |
| 56[11a,c] | 55.0 | 45.0 | — |
| 57[11a,c] | 55.0 | — | 45.0 |

[11a]= 8 wt. % leuprolide acetate loaded;
[11b]= 50 mg depot injection per rat;
[11c]= Placebos without leuprolide acetate.

TABLE 12

| Formulation | P(DL)LA R202 (wt %) | BB (wt %) | BA (wt %) |
|---|---|---|---|
| 58[12a,b] | 50.6 | 41.4 | — |
| 59[12a,b] | 50.6 | — | 41.4 |
| 60[12b,c] | 55.0 | 45.0 | — |
| 61[12b,c] | 55.0 | — | 45.0 |

[12a]= 8 wt. % leuprolide acetate loaded;
[12b]= 100 mg depot injection per rat;
[12c]= Placebos without leuprolide acetate.

EXAMPLE 12

Rheological Properties of Depot Formulations

Figure 2:
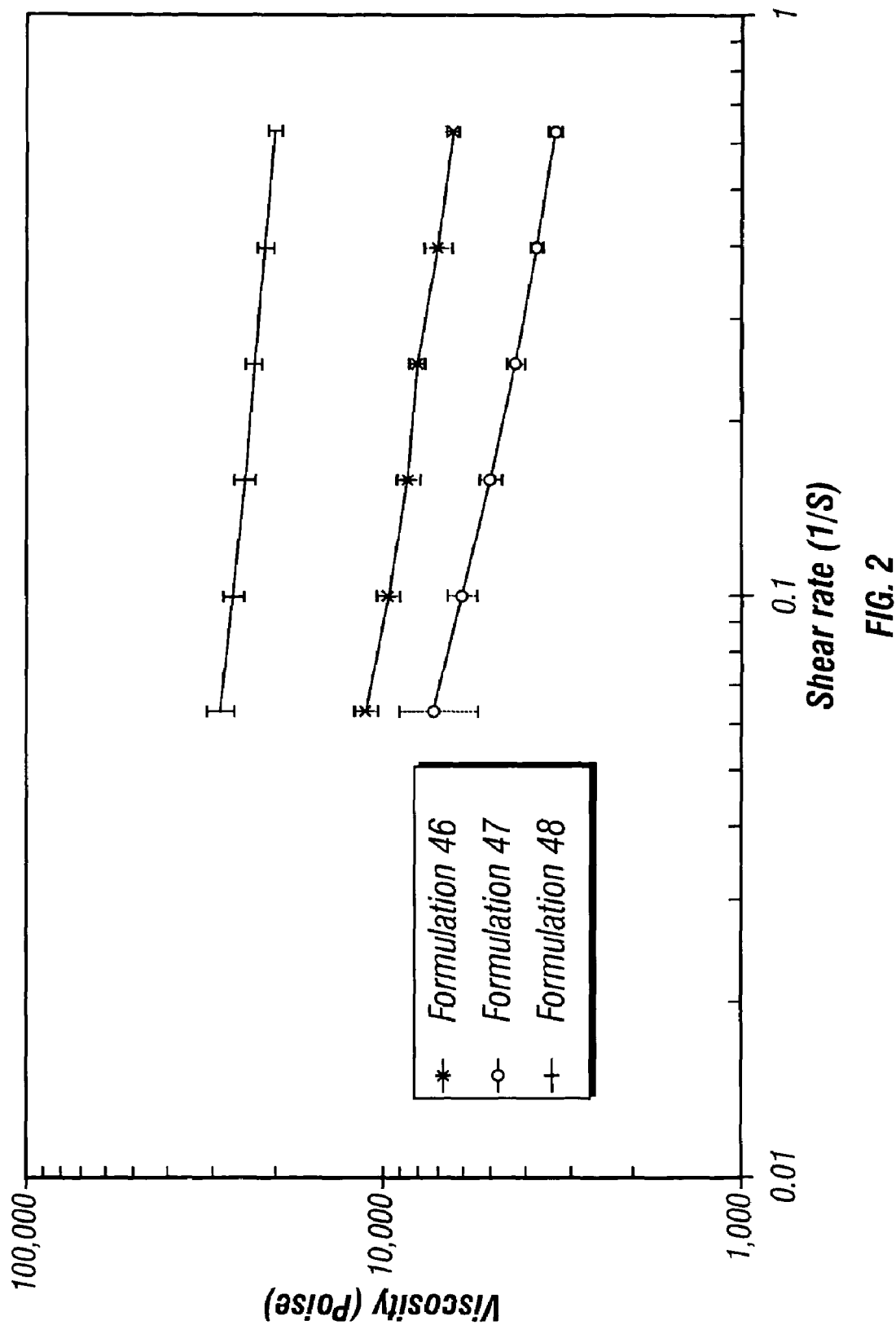
FIG. 2 is a graph illustrating the rheological properties of the depot formulation of the present invention (formulations 46-48).
Figure 3:
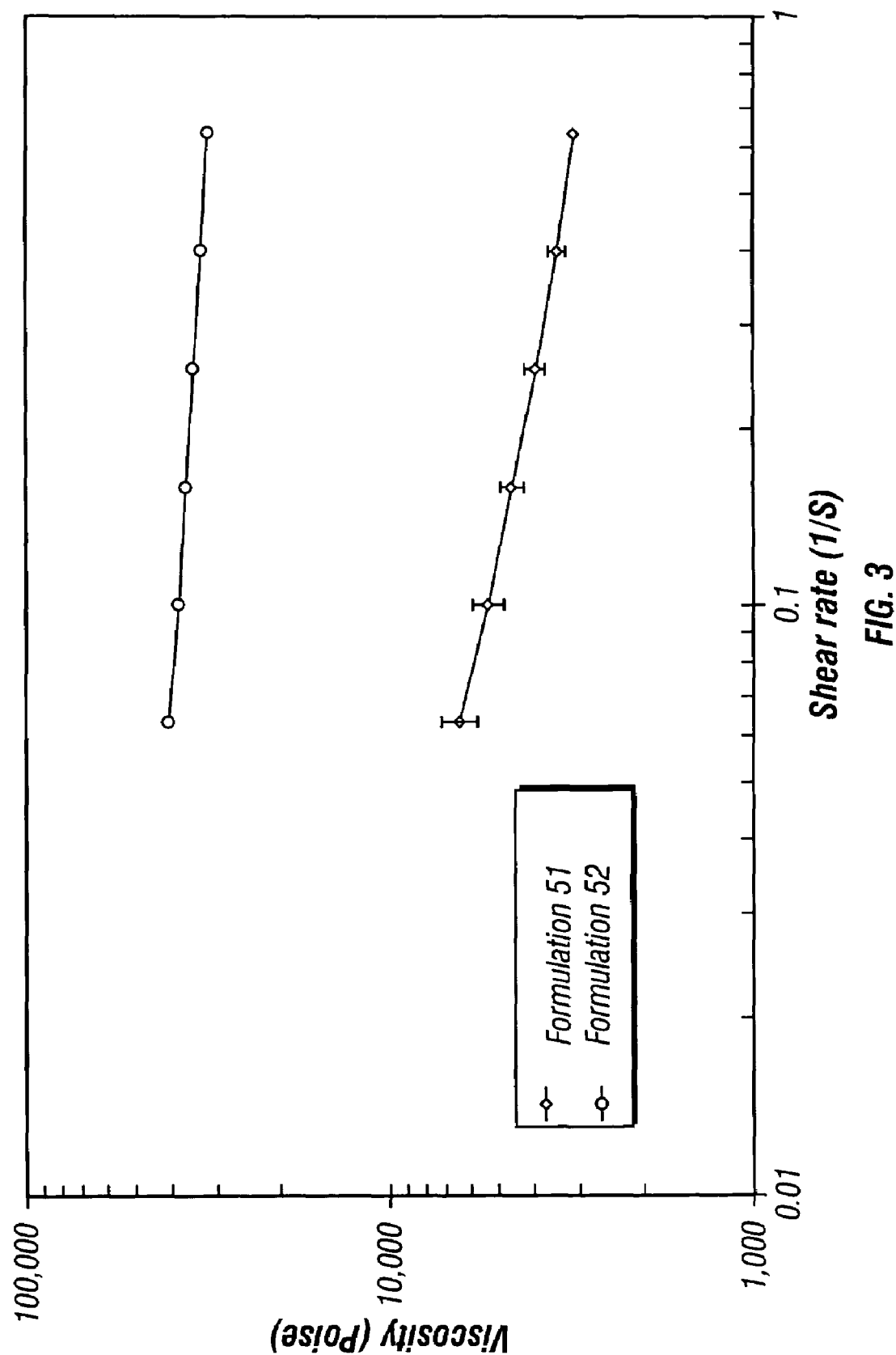
FIG. 3 is a graph illustrating the rheological properties of the depot formulation of the present invention (formulations 51 and 52).

In general, viscosity of the depot vehicle formulations was tested using a Bohlin CVO 120 rheometer (Bohlin Instruments, Cranbury, N.J.). All testing was performed at 24° C. using 20 mm parallel plates. The viscosity of various gel formulations or leuprolide acetate depot formulations of the invention, as tabulated in Tables 6-12, was tested as described above. As illustrated in FIGS. 1, 2 and 3, the depot formulations (Formulations 42-48, 51 and 52) have different rheological properties. Thus, the depot formulations with a wide range of viscosities can be achieved by the combination of different polymers (PLGA type, molecular weight etc.), solvent or co-solvent, and different polymer/solvent ratios according to the present invention.

EXAMPLE 13

Injection Force of Leuprolide Acetate Depot Formulations

The injection force of the depot vehicle formulations was tested on an Instron tensile testing instrument (Instron, Canton, Mass.), where the maximum force required to move the syringe plunger at a speed of 1 ml/minute was determined. The vehicle formulations were prefilled into Hamilton syringes prior to the Instron tests. All tests were conducted at room temperature, using a 24-gauge 0.5 inch long needle.

Figure 4:
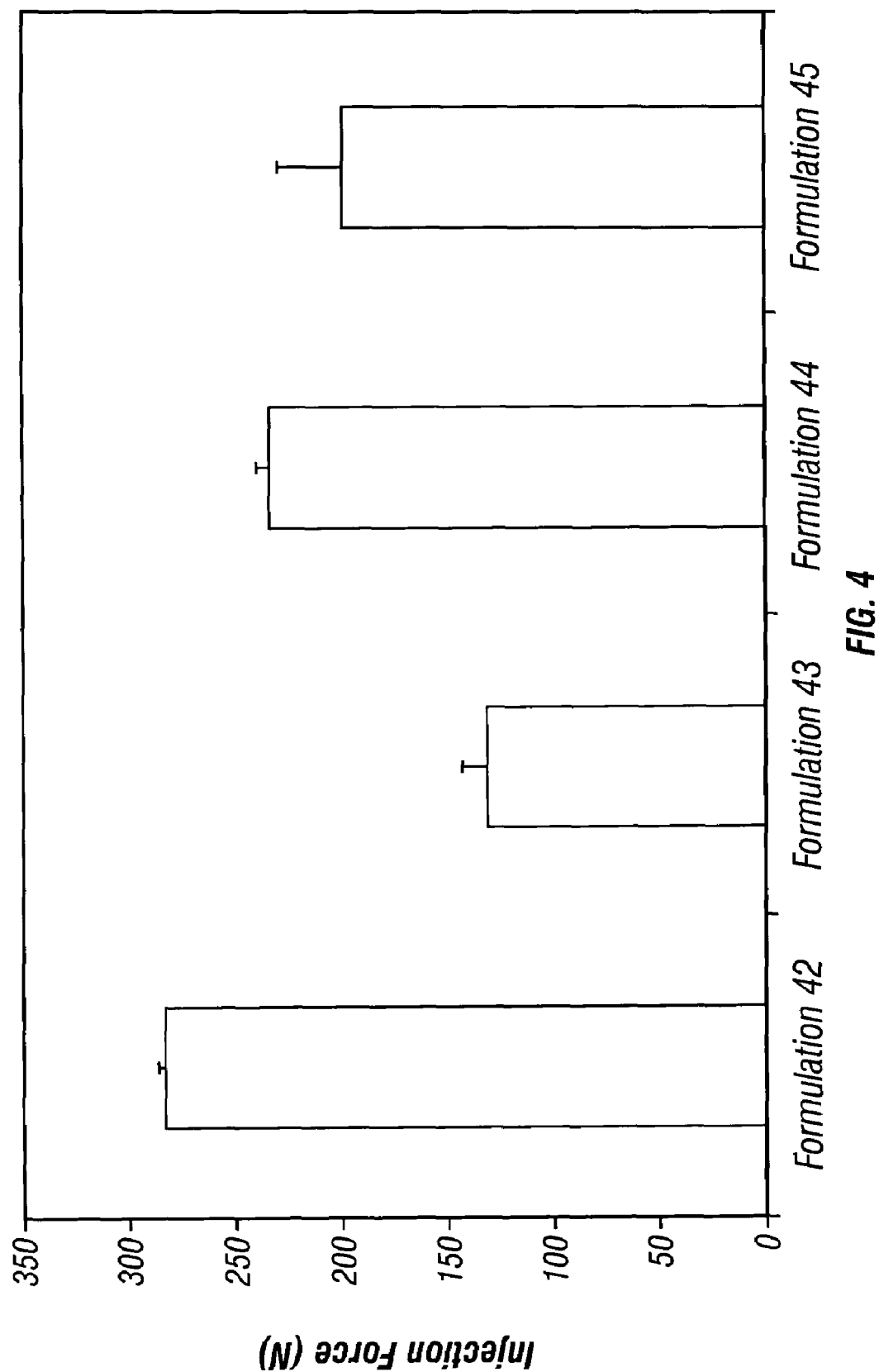
FIG. 4 is a graph illustrating the injection forces of the depot formulations of the present invention (formulations 42-45).
Figure 5:
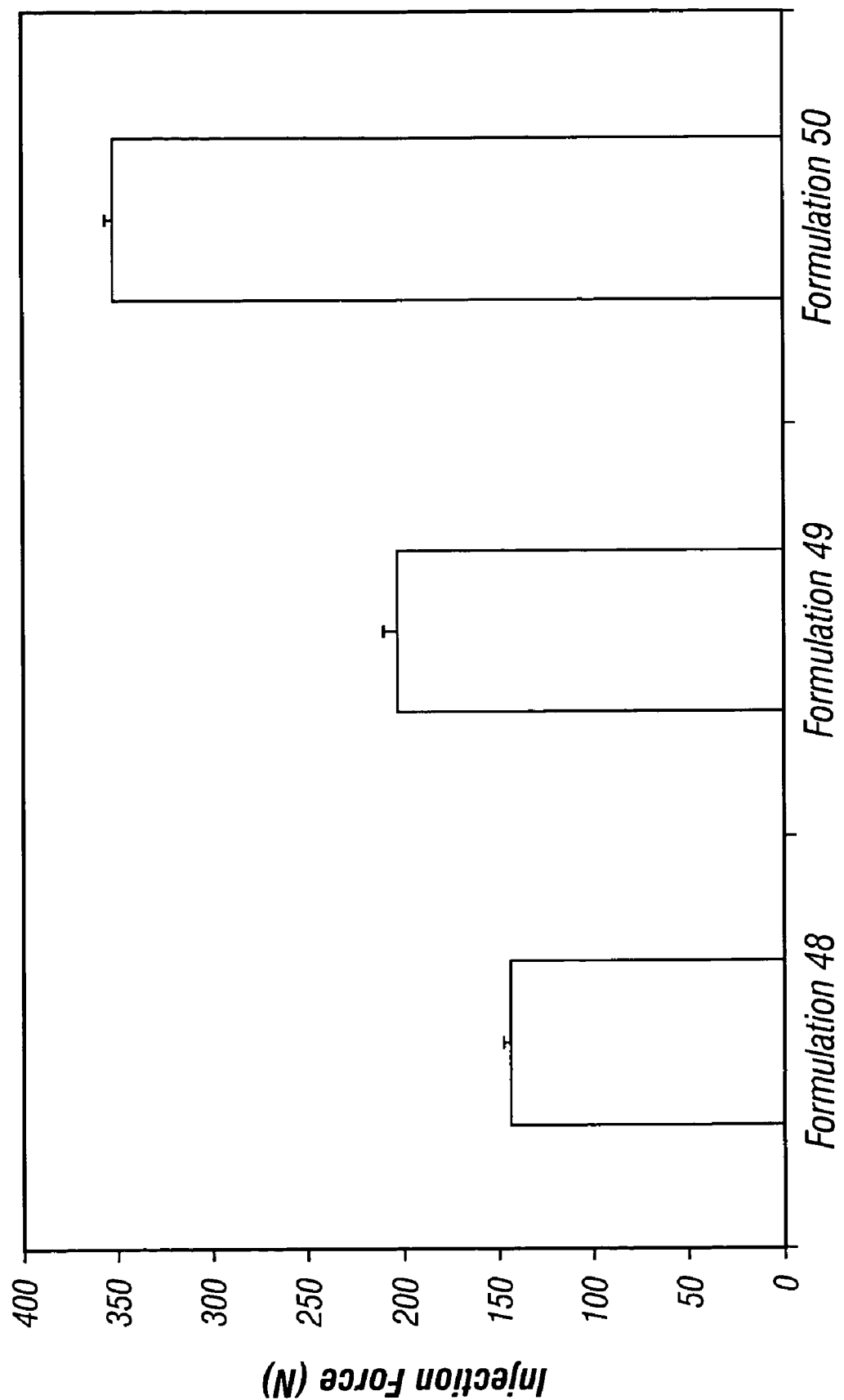
FIG. 5 is a graph illustrating the injection forces of the depot formulations of the present invention (formulations 48-50).
Figure 6A:
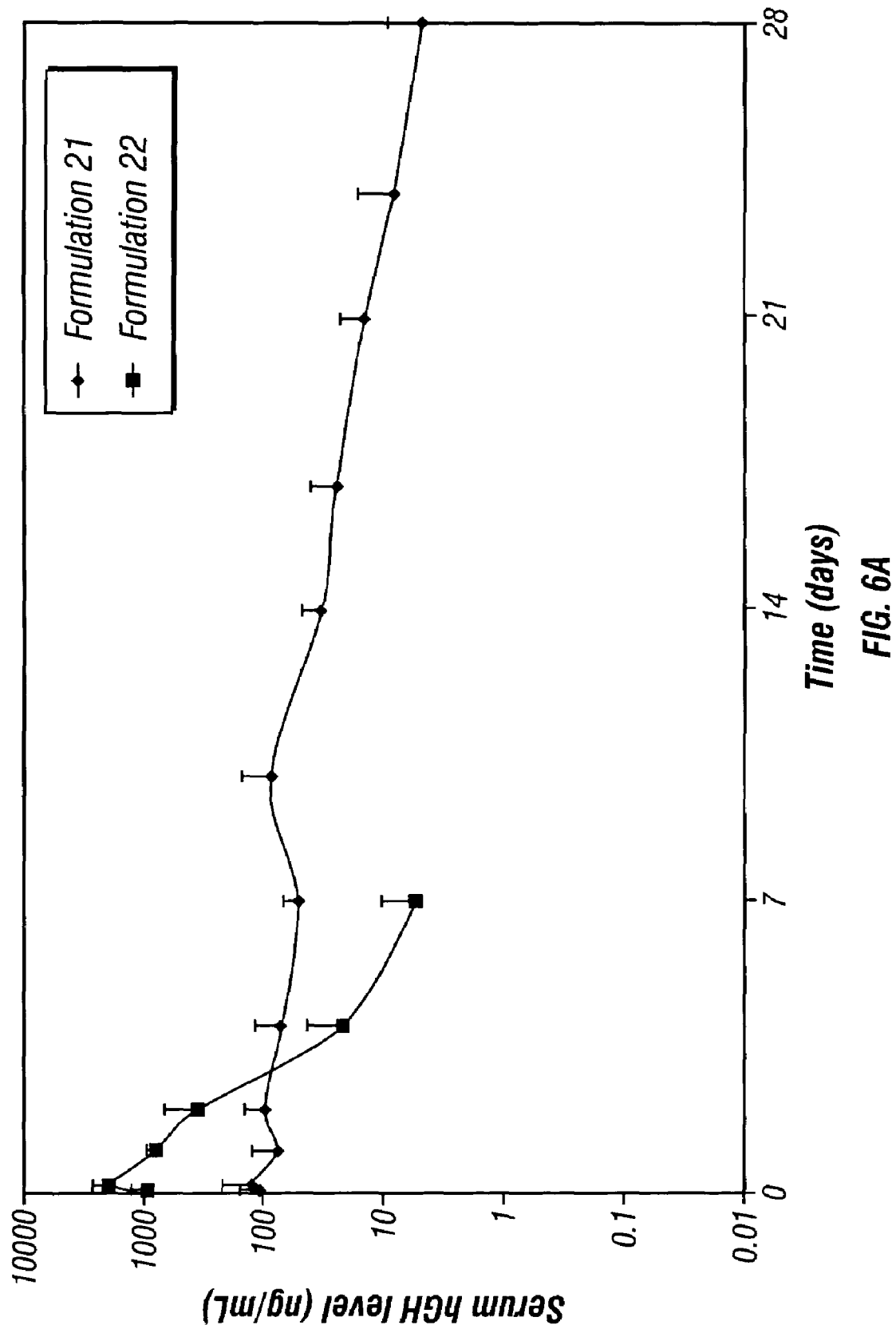
FIG. 6A is a graph illustrating the in vivo release profile of human growth hormone (hGH) obtained from depot formulations of the present invention (formulations 21 and 22).
Figure 6B:
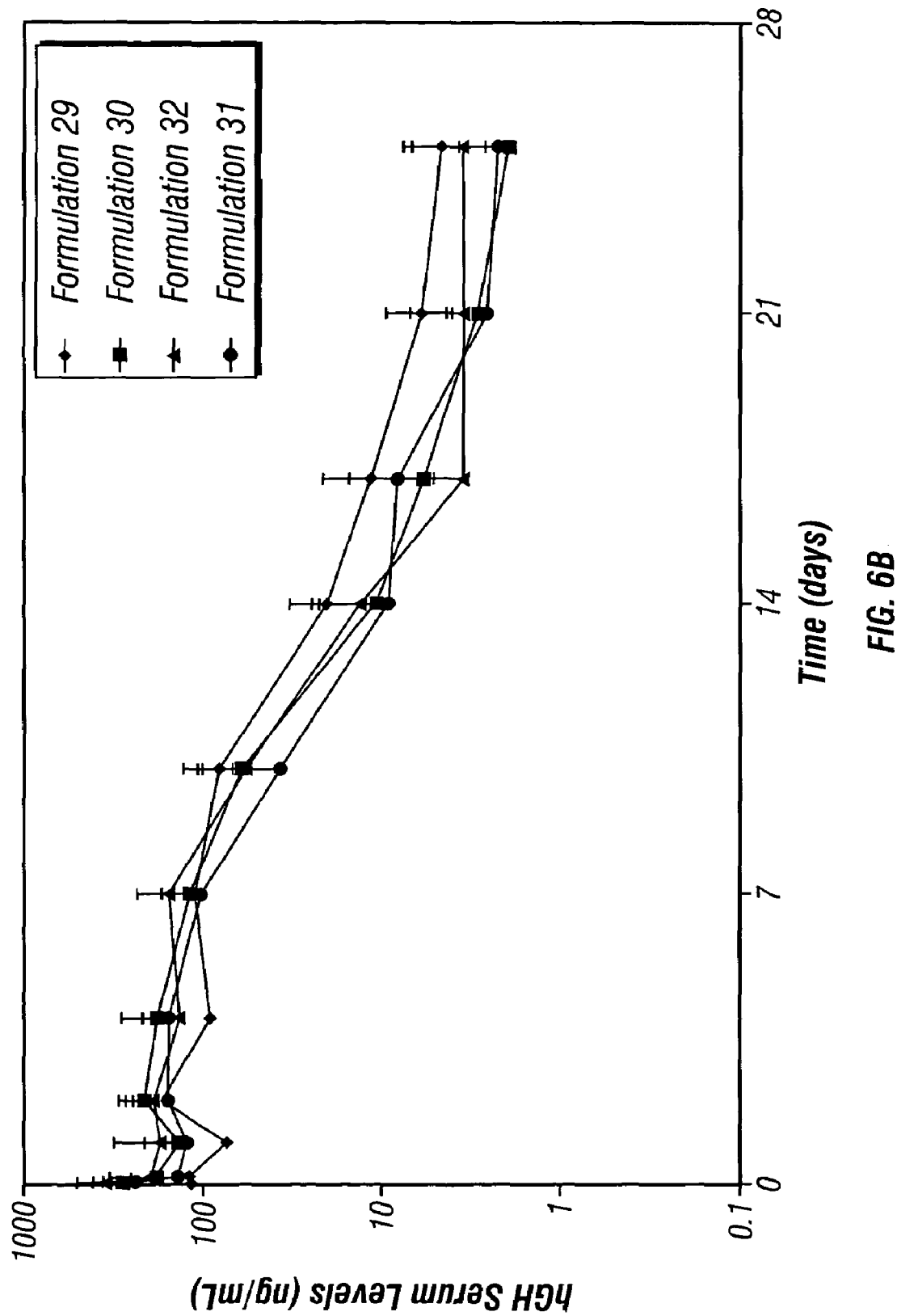
FIG. 6B is a graph illustrating the in vivo release profile of human growth hormone obtained from various depot formulations, including those of the present invention (formulations 29-31).
Figure 6C:
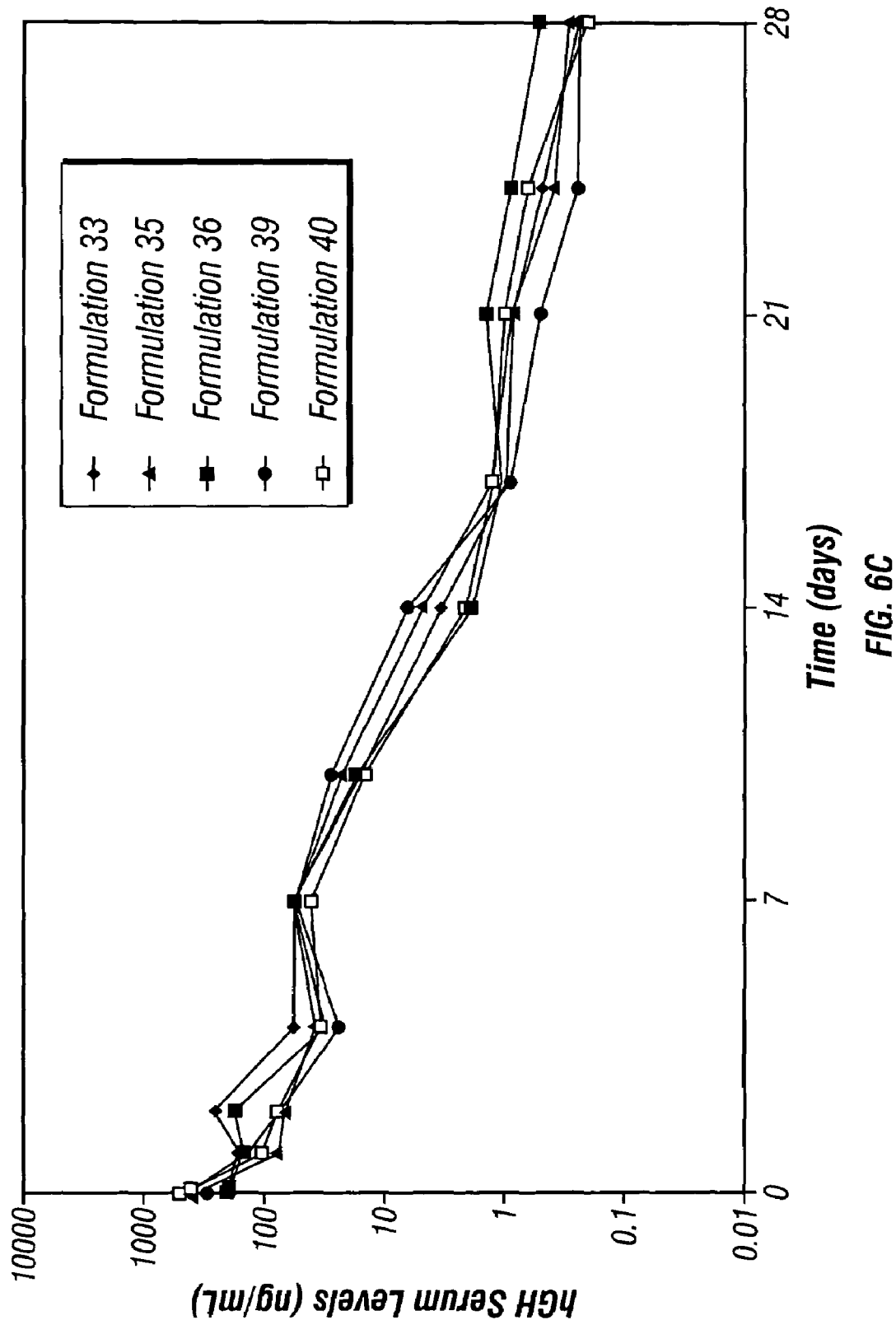
FIG. 6C is a graph illustrating the in vivo release profile of human growth hormone obtained from various depot formulations, including those of the present invention (formulations 33, 35, 36, 39 and 40).
Figure 6D:
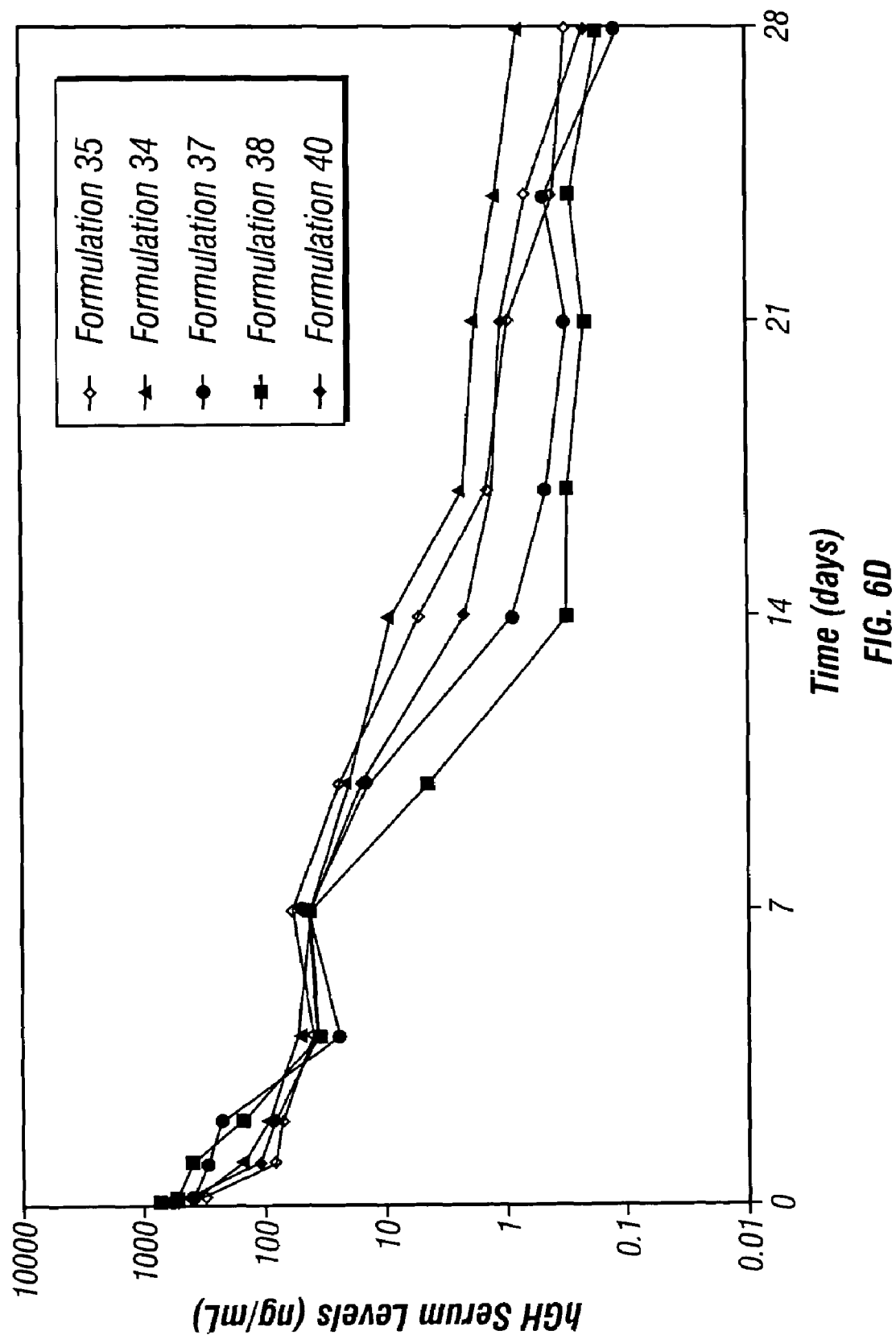
FIG. 6D is a graph illustrating the in vivo release profile of human growth hormone obtained from various depot formulations, including those of the present invention (formulations 34, 35, 37, 38 and 40).

The injection force of various gel formulations or leuprolide acetate depot formulations of the invention, as tabulated in Tables 6-12, was tested as described above. As illustrated in FIGS. 4 and 5, the depot formulations (Formulations 42-45 and 48-50) have different injection forces. Thus, depot formulations with different injection forces can be tailored by the combination of different polymers (PLGA type, molecular weight etc.), solvent or co-solvent, or different polymer/solvent ratios according to the present invention.

EXAMPLE 14

In Vitro Release Rate Profiles of Depot Gel Formulations

A representative number of implantable gels were prepared in accordance with the foregoing procedures and tested for in vitro release of beneficial agent as a function of time. In general, the in vitro release of bioactive agent from the depot formulation of the present invention was performed as follows. The depot gel formulation (80-120 mg) was loaded into a tea bag and placed in a 20 mL scintillation vial and the release medium (5 mL, phosphate buffer saline (PBS) +0.1% TWEEN® 20, pH 7.4) was added to the vial. The vial was incubated in a 37° C. water bath with gentle agitation. The medium was replaced daily for the first 5 days, then twice a week thereafter until the end of the release duration. The amount of bioactive agent released from the depot was measured by various methods dependent on the nature of the bioactive agent: size exclusion chromatography high pressure liquid chromatography (SEC HPLC) is generally used for protein, while reverse phase high pressure liquid chromatography (rpHPLC) or ultraviolet (UV) techniques are generally used for small molecular compounds.

EXAMPLE 15

In Vivo Release Rate Profiles of Depot Gel Formulations

A representative number of implantable gels were prepared in accordance with the foregoing procedures and tested for in vivo studies in rats to determine release of the beneficial agent as determined by blood serum or plasma concentrations of beneficial agent as a function of time.

In general, in vivo studies in rats were performed following an open protocol to determine plasma levels of the beneficial agent (e.g., hGH, bupivacaine, leuprolide, buprenorphine) upon systemic administration of the beneficial agent via the implant systems of this invention. Depot gel formulations containing the beneficial agent (prepared as described in the Examples above) were loaded into 0.25 cc or 0.5 cc disposable syringes (e.g., Hamilton Gastight syringes) or catheters. Disposable needles (16 gauge or 18 gauge) were attached to the syringes and were heated to 37° C. using a circulator bath. The depot gel formulations (as tabulated in Tables 1-12) were injected into rats and blood was drawn at specified time intervals. All plasma samples were stored at 4° C. prior to analysis. Samples were analyzed for the beneficial agent using any one of the following methods: radio immuno assay (RIA) or validated LC/MS/MS method (Ricerca, LLC, Painesville, Ohio).

EXAMPLE 16 hGH In Vivo Studies

A representative number of implantable gels as tabulated in Tables 4-6 were tested for in rats to determine in vivo release rate profiles as described in Example 15 above. In particular, depot gel hGH compositions were injected from customized 0.5 cc disposable syringes having disposable 16-gauge needles, into rats and blood was drawn at specified time intervals. The release rate profile of hGH from various depot gel formulations was determined by measuring the blood serum or plasma concentrations of hGH as a function of time, as illustrated in FIGS. 6A-D (formulations 21, 22, 29-31, and 33-40). Samples were analyzed for intact hGH content using a radio immuno assay (RIA).

EXAMPLE 17

Bupivacaine In Vivo Studies

Figure 7:
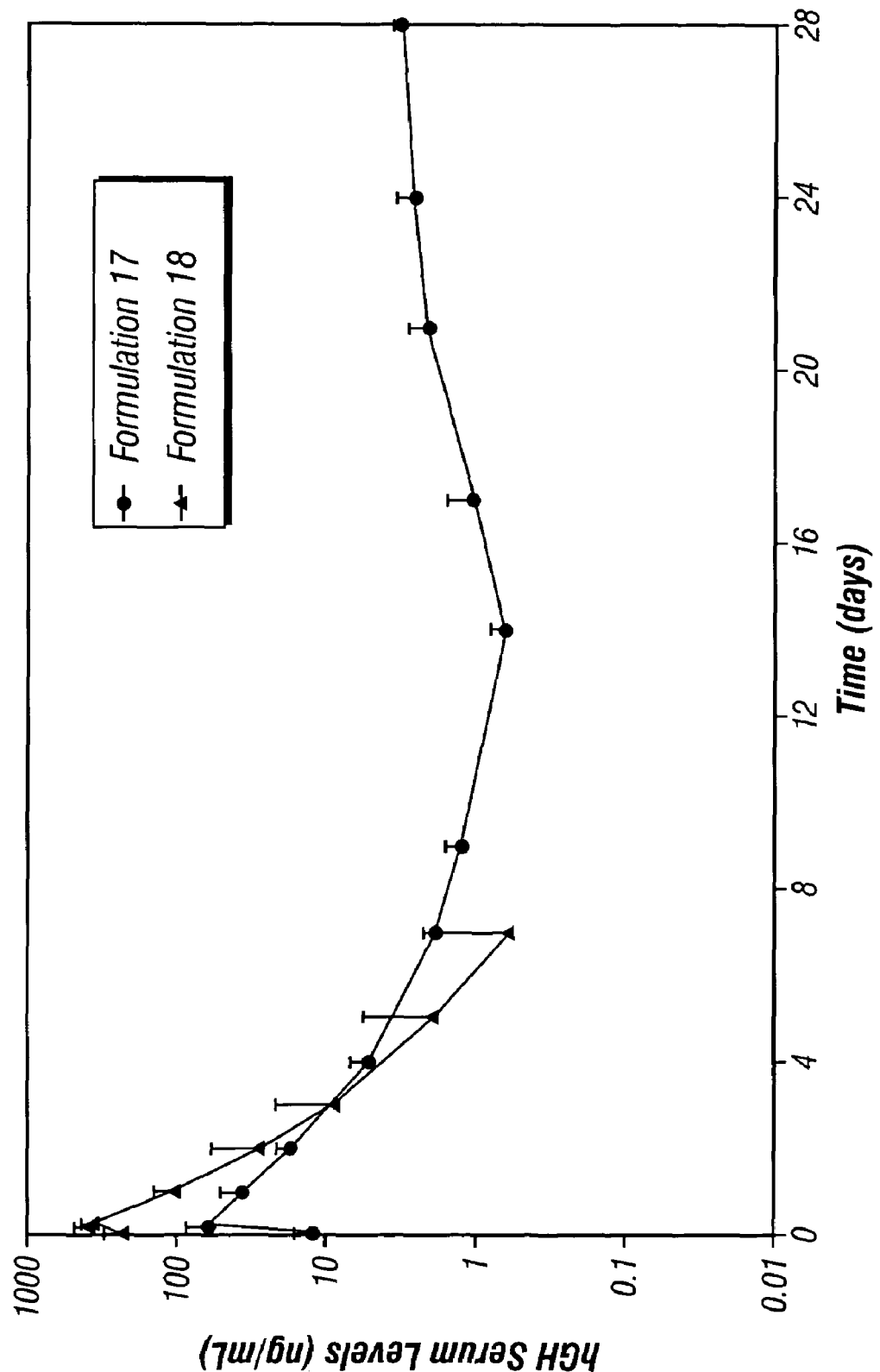
FIG. 7 is a graph illustrating the in vivo release profile of bupivacaine hydrochloride obtained from depot formulations of the present invention (formulations 17-18).
Figure 8:
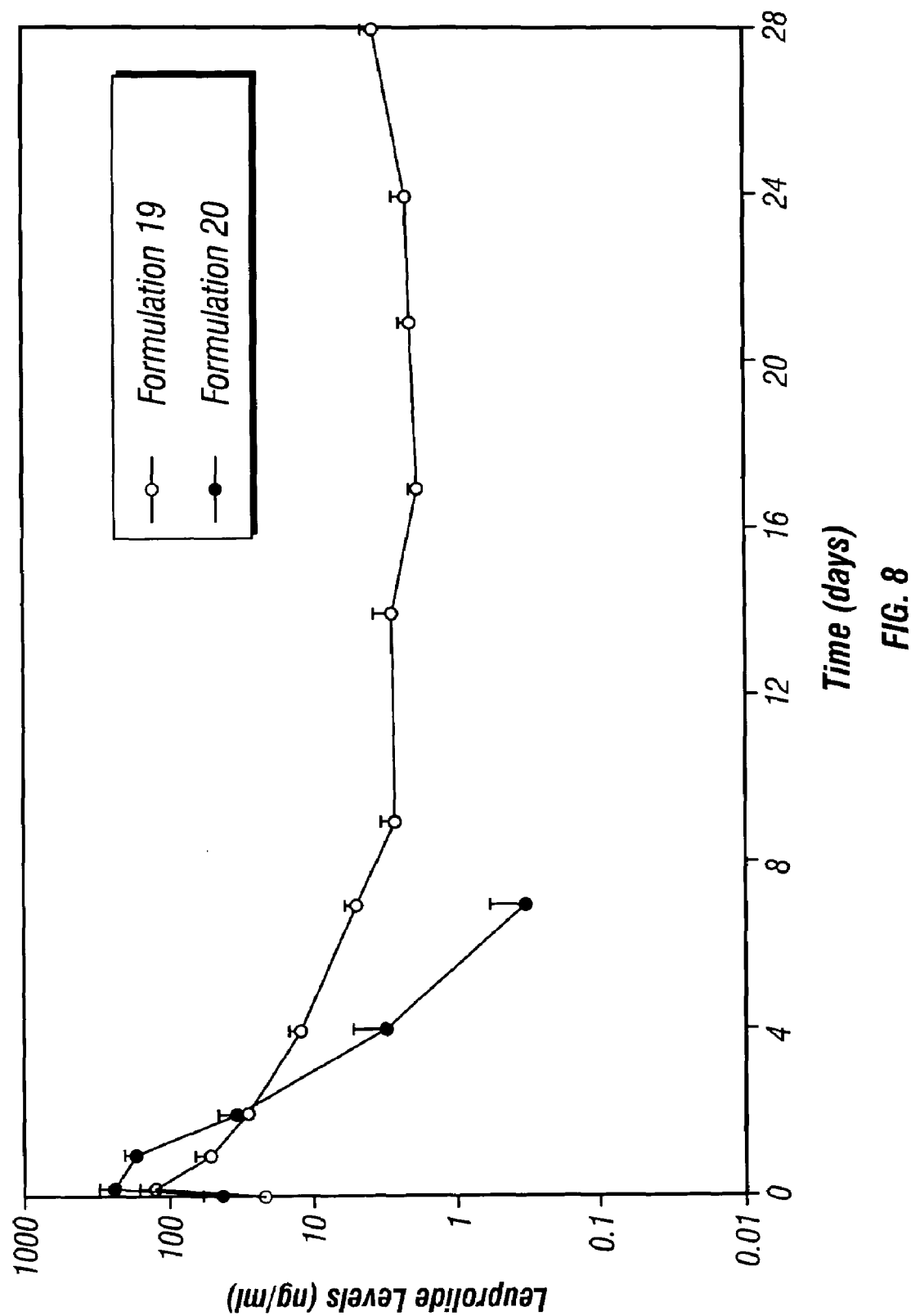
FIG. 8 is a graph illustrating the in vivo release profile of bupivacaine base obtained from depot formulations of the present invention (formulations 19-20).
Figure 9:
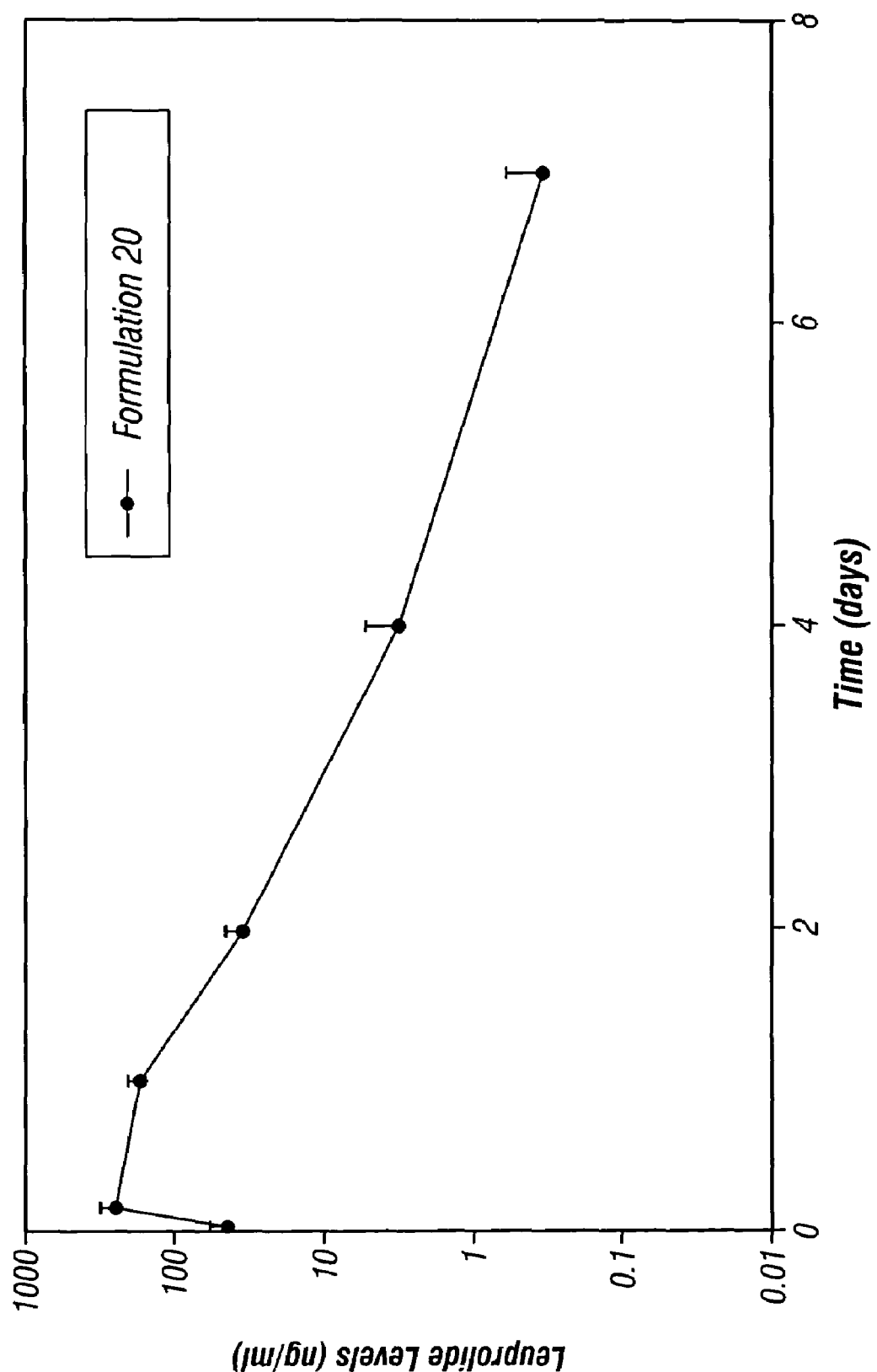
FIG. 9 is a graph illustrating the in vivo release profile of bupivacaine base obtained from a depot formulation of the present invention (formulation 20).

A representative number of implantable gels as tabulated in Table 4 were tested for in rats to determine in vivo release rate profiles as described in Example 15 above. In particular, depot gel bupivacaine compositions were injected from customized 0.5 cc disposable syringes having disposable 18-gauge needles, into rats and blood was drawn at specified time intervals (1 hour, 4 hours and on days 1, 2, 5, 7, 9 and 14, 21 and 28) and analyzed for bupivacaine using LC/MS. FIGS. 7, 8 and 9 illustrate representative in vivo release profiles of bupivacaine hydrochloride (formulations 17 and 18) and bupivacaine base (formulations 19 and 20) obtained in rats from various depot formulations, including those of the present invention. The in vivo release profile of the depot formulations with low molecular weight PLGA (formulations 18 and 20 in FIGS. 7, 8 and 9) exhibited a shorter release duration of approximately 7 days, as compared to the control formulations (with higher molecular weight PLGA, formulations 17 and 19).

EXAMPLE 18

Bupivacaine In Vivo Studies

Figure 10:
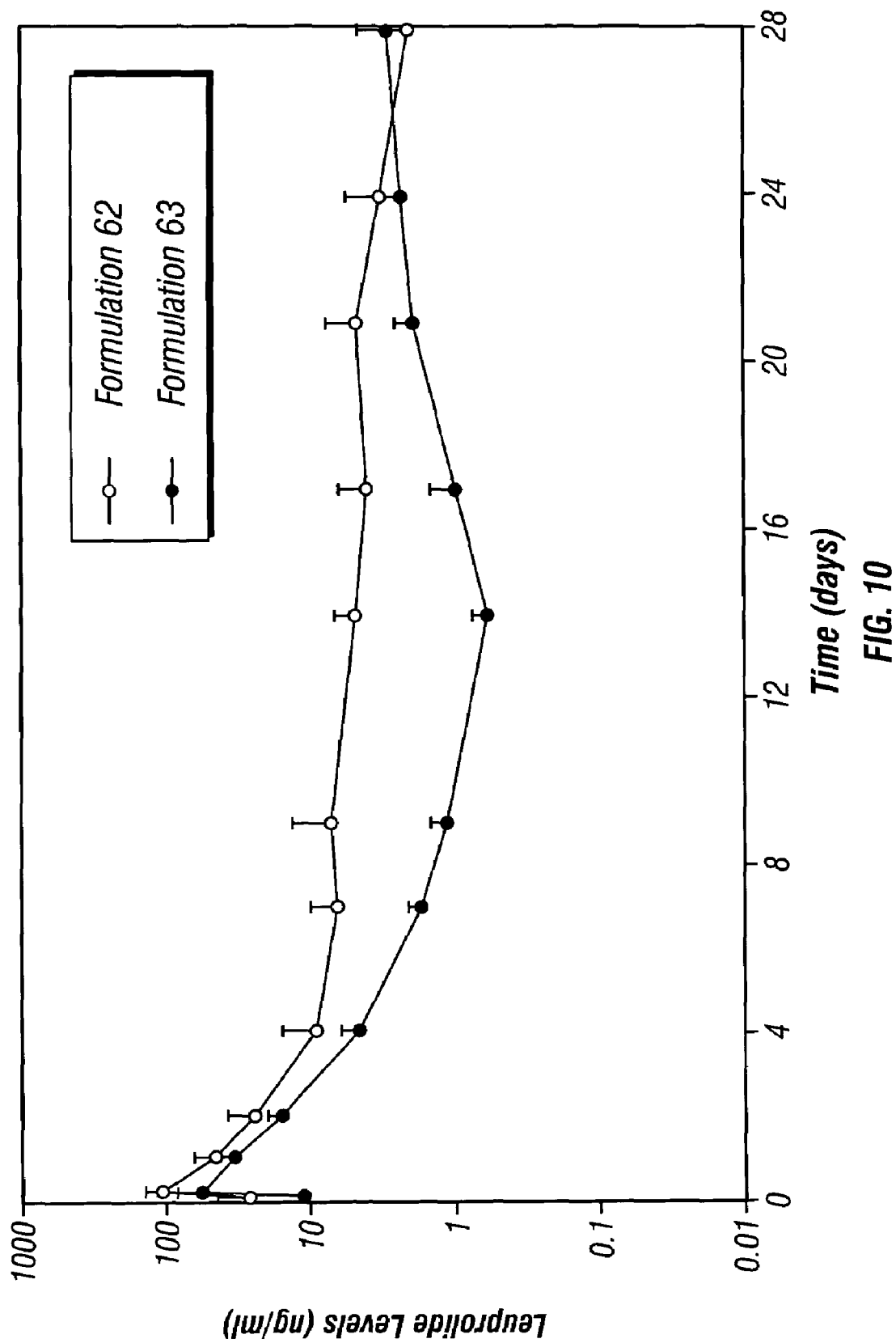
FIG. 10 is a graph illustrating the in vivo release profile of bupivacaine hydrochloride obtained from depot compositions of the present invention (formulations 62 and 63).
Figure 11:
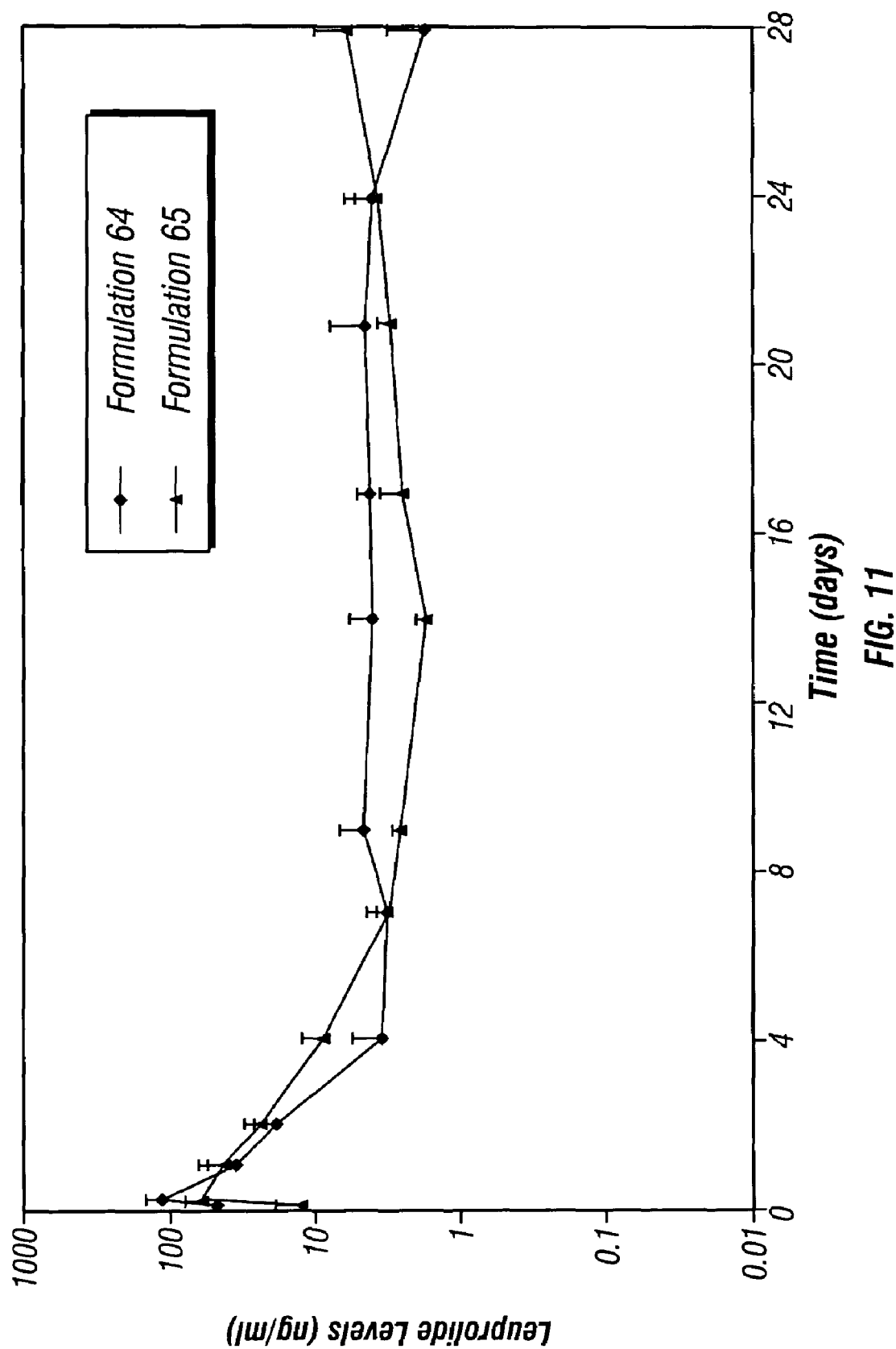
FIG. 11 is a graph illustrating the in vivo release profile of bupivacaine hydrochloride obtained from depot compositions of the present invention (formulations 64 and 65).

A representative number of implantable gels as tabulated in Table 13 were tested for in rats to determine in vivo release rate profiles as described in Example 17 above. FIGS. 10 and 11 illustrate representative in vivo release profiles of bupivacaine obtained in rats from various depot formulations, including those of the present invention. As illustrated in the figures, when the same amount of bupivacaine was administrated, the duration of the in vivo sustained release of bupivicaine from the formulation is directly proportional to the percent loading of bupivacaine within the depot gel composition. In particular, at 10% bupivacaine HCl loading, the amount of bupivicaine released increased with time after an initial decline during the first two weeks. Although not wanting to be limited to a particular theory, the results indicate that the early stage diffusion mechanism may be the primary mechanism contributing to the release of the beneficial agent, while at later stages, polymer degradation might significantly contribute to the release.

TABLE 13

| Formulation | PLGA RG502 (wt %) | Benzyl Benzoate (wt %) | Bupivacaine (wt %) |
|---|---|---|---|
| 62 | 35 | 35 | 30[13a] |
| 63 | 45 | 45 | 10[13a] |
| 64 | 35 | 35 | 30[13b] |
| 65 | 45 | 45 | 10[13b] |

[a]= particle size of bupivacaine is ca. 35μm;
[b]= particle size of bupivacaine is ca. 90μm.

EXAMPLE 19

Figure 12:
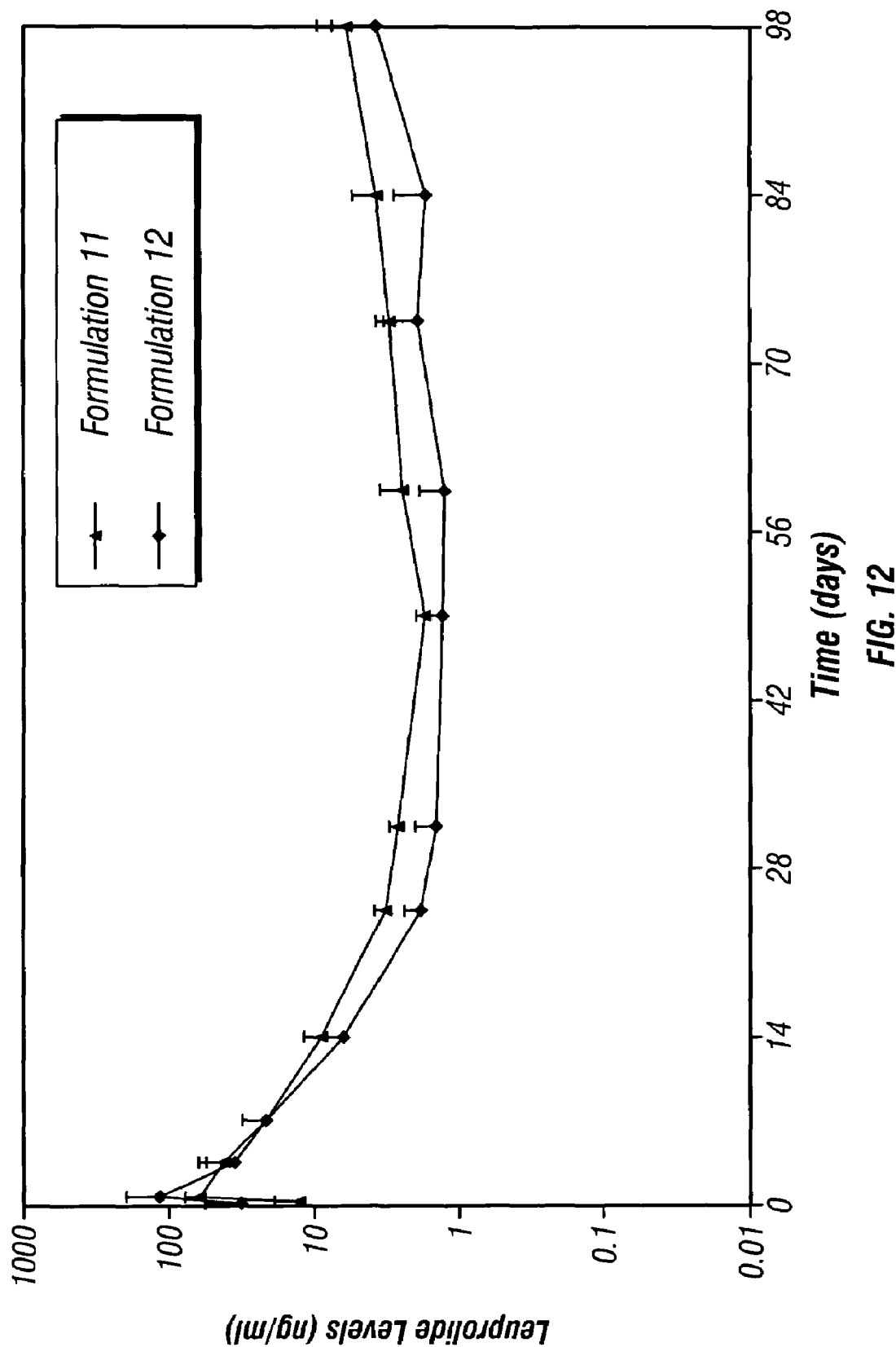
FIG. 12 is a graph illustrating the in vivo release profile of bupivacaine hydrochloride obtained from depot compositions of the present invention (formulations 11 and 12).

In Vivo Studies on Bupivacaine Depot Composition With Different PLGA Molecular Weight Distributions A representative number of implantable gels as tabulated in Table 2 were tested for in rats to determine in vivo release rate profiles as described in Example 15 above. In particular, depot gel bupivacaine compositions were injected from customized 0.5 cc disposable syringes having disposable 18-gauge needles, into rats and blood was drawn at specified time intervals (1 hour, 4 hours and on days 1, 2, 5, 7, 9 and 14, 21 and 28) and analyzed for bupivacaine using LC/MS. FIG. 12 illustrates the representative in vivo release profiles of bupivacaine obtained in rats from the formulations 11 and 12 (the bupivacaine depots were formulated with the PLGAs with two different molecular weight distributions in benzyl benzoate (single-modal containing MMW PLGA RG502, and bi-modal mixture of HMW PLGA RG503 with LMW PLGA, Table 2, formulations 11 and 12).

EXAMPLE 20

In Vivo Release Rate Profiles of Various Leuprolide Acetate Depot Formulations

A representative number of implantable gels as tabulated in Tables 7-9 were tested for in rats to determine in vivo release rate profiles as described in Example 15 above. In particular, the release rate profile of leuprolide was determined by measuring the blood serum or plasma concentrations of leuprolide as a function of time, as illustrated in FIGS. 13-16.

Figure 13:
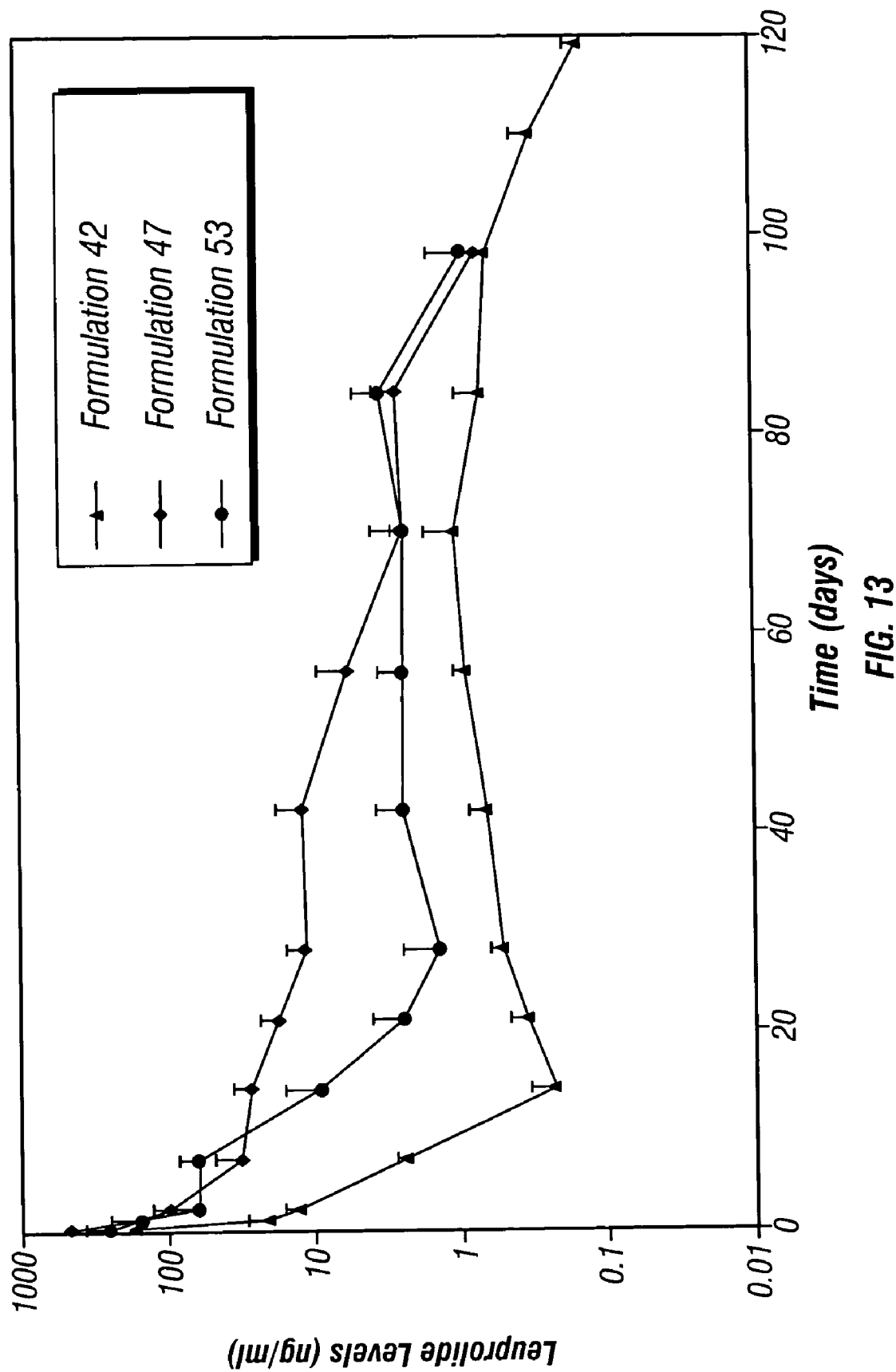
FIG. 13 is a graph illustrating the in vivo release profile of leuprolide acetate obtained from the depot formulations of the present invention (formulations 42 and 47) as compared with 3-month LUPRON DEPOT® (formulation 53).
Figure 14:
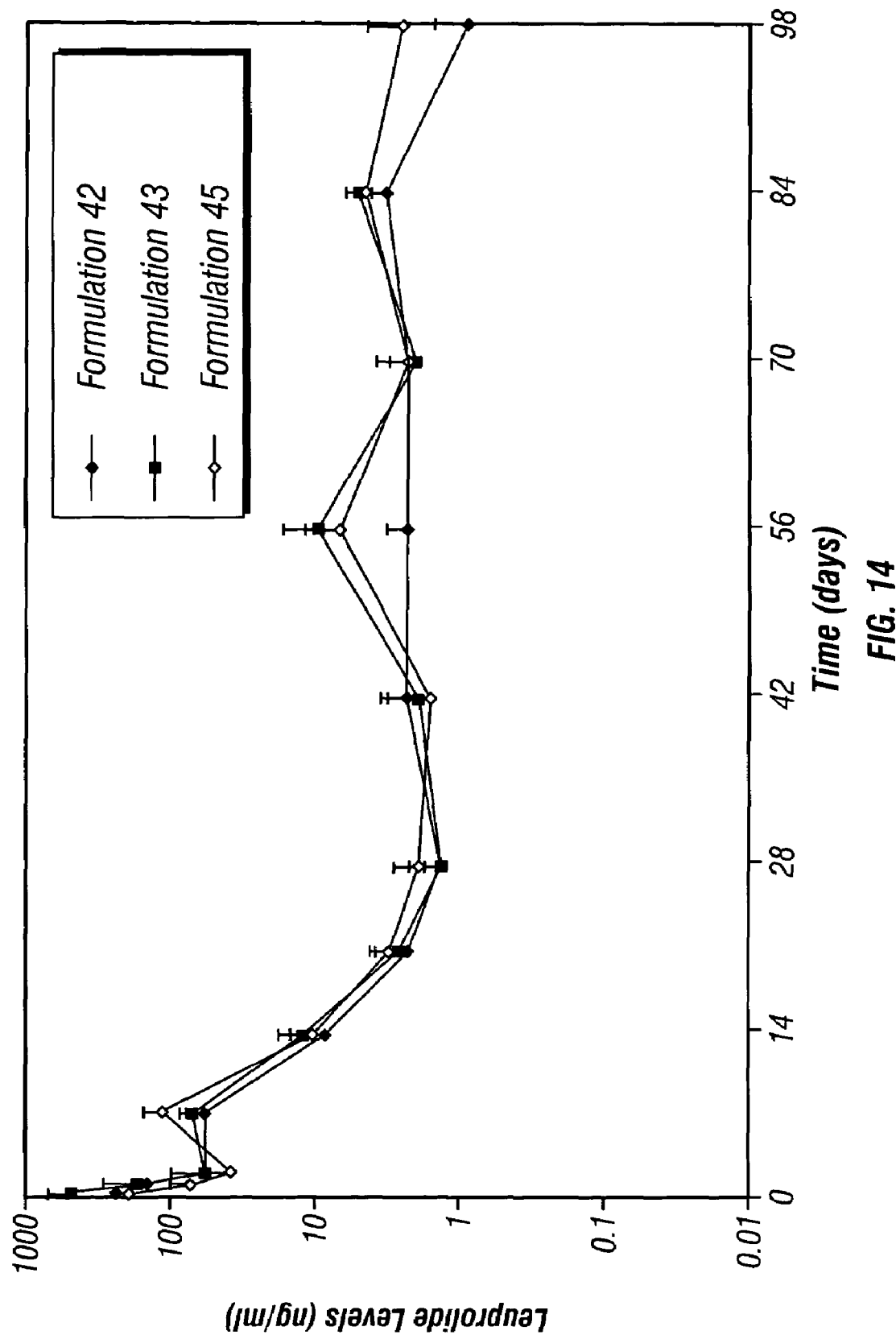
FIG. 14 is a graph illustrating the in vivo release profile of leuprolide acetate obtained from the depot formulations of the present invention (formulations 42, 43 and 45).
Figure 15:
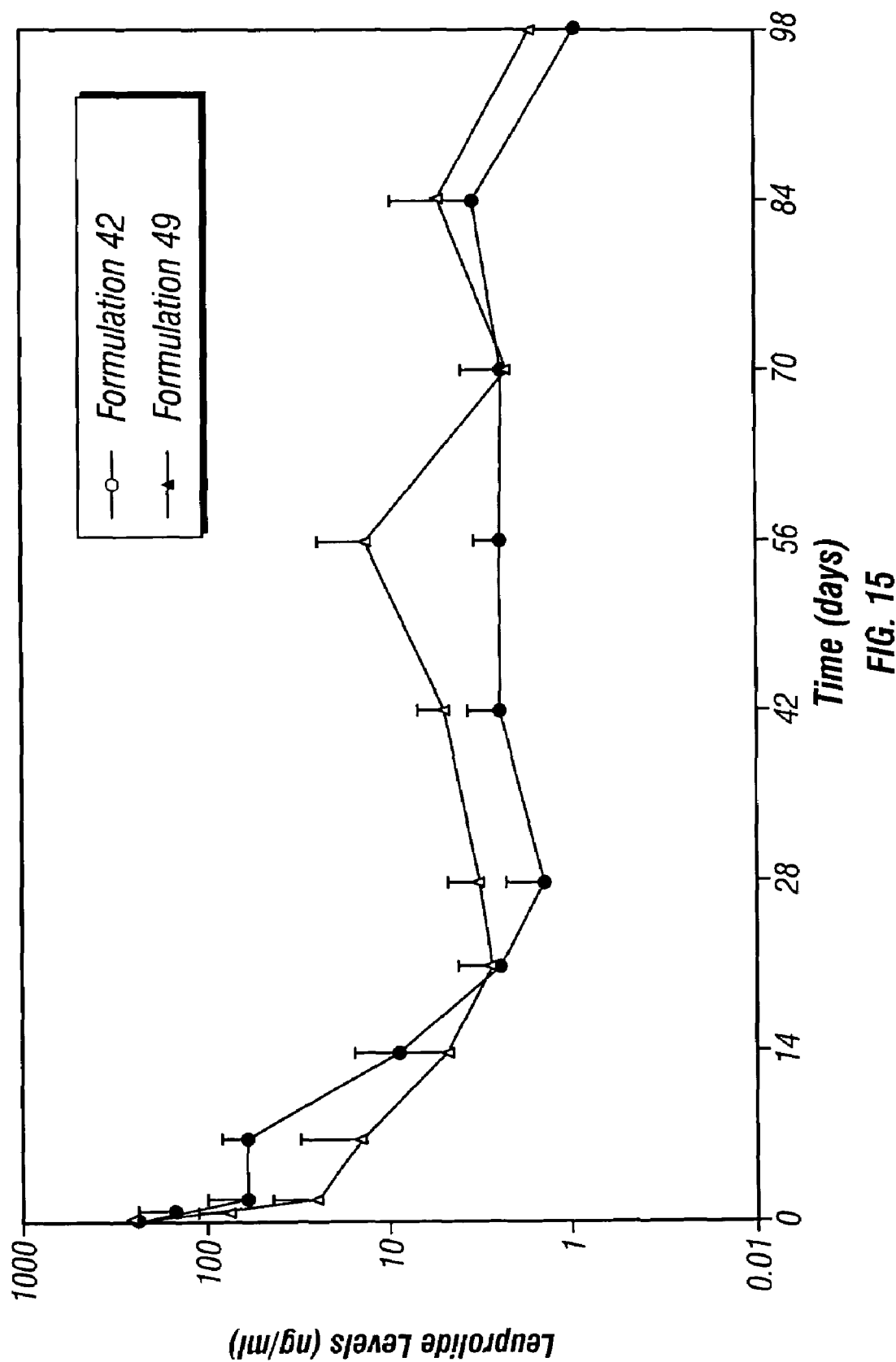
FIG. 15 is a graph illustrating the in vivo release profile of leuprolide acetate obtained from the depot formulations of the present invention (formulations 42 and 49).
Figure 16:
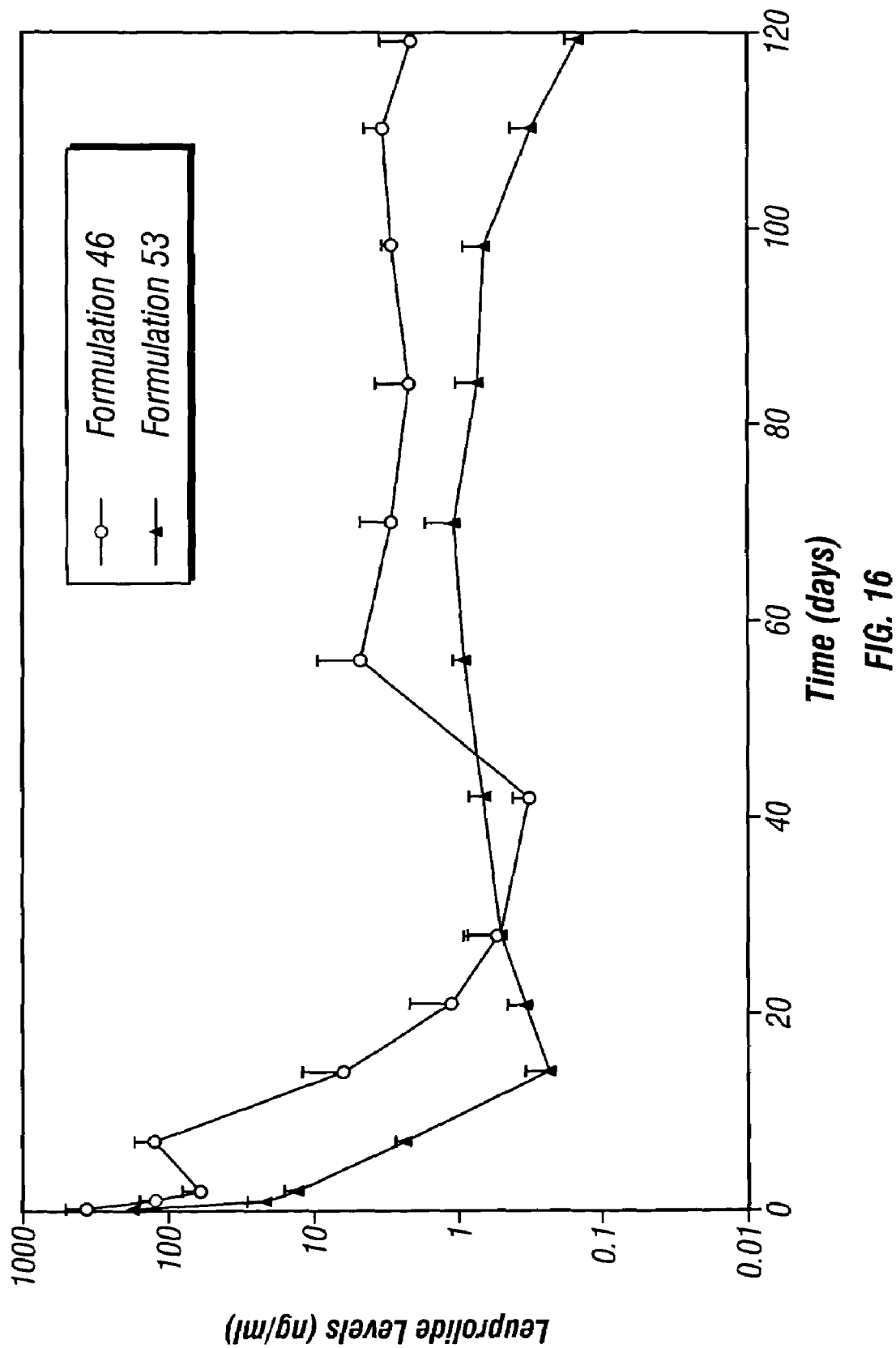
FIG. 16 is a graph illustrating the in vivo release profile of leuprolide acetate obtained from the depot formulation of the present invention (formulation 46) as compared with 3-month LUPRON DEPOT® (formulation 53).

In particular, FIG. 13 illustrates representative in vivo release profiles of leuprolide acetate obtained in rats from depot formulations according to the present invention containing PLGA (L/G: 75/25) in either benzyl benzoate (BB) (formulation 42) or benzyl alcohol (BA) (formulation 47), as compared to a commercial 3-month leuprolide acetate depot, LUPRON DEPOT® (formulation 53). FIG. 14 illustrates representative in vivo release profiles of leuprolide acetate obtained in rats from depot formulations according to the present invention containing PLGA (L/G: 75/25) in benzyl benzoate, a mixture of benzyl benzoate and benzyl alcohol, or benzyl benzoate with ethanol as a thixotropic agent (formulations 42, 43 and 45, respectively). FIG. 15 illustrates representative in vivo release profiles of leuprolide acetate obtained in rats from depot formulations according to the present invention containing PLGA (L/G: 75/25) in benzyl benzoate with the drug particles formulated either with or without stearic acid (formulations 42 & 49). FIG. 16 illustrates representative in vivo release profiles of leuprolide acetate obtained in rats from depot formulations according to the present invention containing poly(caprolactone-co-lactic acid) (PCL-co-LA) (CL/L: 25/75) in benzyl benzoate (formulation 46) as compared to a commercial 3-month leuprolide acetate depot, LUPRON DEPOT® (formulation 53- from TAP (the front chamber of LUPRON DEPOT® 3-month 11.25 mg prefilled dual-chamber syringe containing leuprolide acetate (11.25 mg), polylactic acid (99.3 mg) and D-mannitol (19.45 mg). The second chamber of diluent contains carboxymethylcellulose sodium (7.5 mg), D-mannitol (75.0 mg), polysorbate 80 (1.5 mg), water for injection, USP and glacial acetic acid, USP to control pH.)).

As illustrated in FIGS. 13-16, sustained release of leuprolide acetate from the depot formulation of the invention can be achieved for a duration of about 3 months to 6 months after administration. The release profiles of the active agent from the depots can be varied by varying the type of polymer and solvent, and by varying the polymer/solvent ratios.

EXAMPLE 21

In Vivo Release Rate Profiles of Various Leuprolide Acetate Depot Formulations

A representative number of implantable gels as tabulated in Table 10 were tested for in rats to determine in vivo release rate profiles as described in Example 15 above. In particular, the release rate profile of leuprolide was determined by measuring the blood serum or plasma concentrations of leuprolide as a function of time, as illustrated in FIG. 17.

Figure 17:
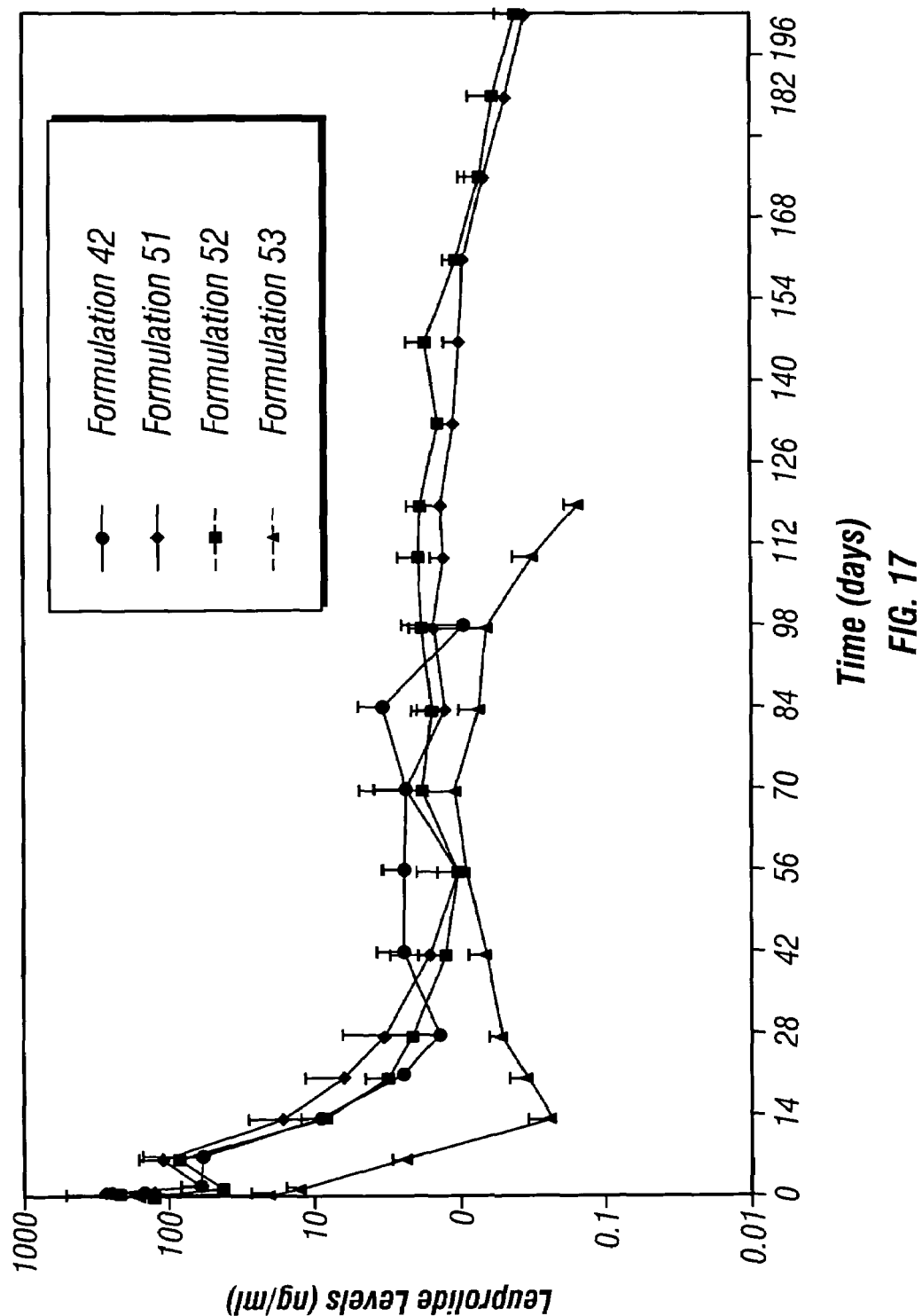
FIG. 17 is a graph illustrating the in vivo release profile of leuprolide acetate obtained from the depot formulation of the present invention (formulations 42, 51 and 52) as compared with 3-month LUPRON DEPOT® (formulation 53).

In particular, FIG. 17 illustrates representative in vivo release profiles of leuprolide acetate obtained in rats from depot formulations according to the present invention containing P(DL)LA in benzyl benzoate (BB) with different polymer/solvent ratios (formulations 51 and 52), as compared to the 3 month durational depot formulation (formulation 42) and a commercial 3-month leuprolide acetate depot, LUPRON DEPOT® (formulation 53).

As illustrated in FIG. 17, sustained release of leuprolide acetate from the depot formulations of the invention can be achieved for a duration greater than or equal to 6 months by using the biodegradable polymer with longer degradation duration. The release profiles of the active agent from the depots can be varied by varying the type of polymer and solvent, and by varying the polymer/solvent ratios.

EXAMPLE 22

In Vivo Release Rate Profiles of Various Buprenorphine Depot Formulations

A representative number of implantable buprenorphine depot gel formulations of the present invention are tested for in rats to determine in vivo release rate profiles as described in Example 15 above. In particular, the release rate profile of buprenorphine is determined by measuring the blood serum or plasma concentrations of leuprolide as a function of time. The release profiles of the active agent from the depots can be varied by varying the type of polymer and solvent, and by varying the polymer/solvent ratios.

EXAMPLE 23

In Vivo Testosterone Suppression by Depot Gel Leuprolide Formulations

In general, in vivo studies in rats were performed following an open protocol to determine plasma levels of leuprolide upon systemic administration of leuprolide via the implant systems of this invention. Depot gel leuprolide formulations (prepared as described in Examples above) were loaded into 0.25 cc Hamilton Gastight syringes. Disposable 18-gauge needles were attached to the syringes and were heated to 37° C. using a circulator bath. Depot gel leuprolide acetate formulations were injected into rats and blood was drawn at specified time intervals. All plasma samples were stored at 4° C. prior to analysis. Samples were analyzed for leuprolide as described in Example 15 above, and for testosterone using a commercially available RIA kit (DSL-4000) (Ricerca, LLC, Painesville, Ohio).

EXAMPLE 24

In Vivo Release Rate Profiles and Efficacy of Various Leuprolide Acetate Depot Formulations A representative number of implantable gels as tabulated in Table 11 were tested for in rats to determine in vivo release rate profiles and efficacy as measured by testosterone suppression as described in Example 23 above. In particular, the release rate profile of leuprolide and efficacy, i.e., testosterone suppression, were determined by measuring the blood serum or plasma concentrations of leuprolide and testosterone as a function of time, as illustrated in FIG. 18.

Figure 18:
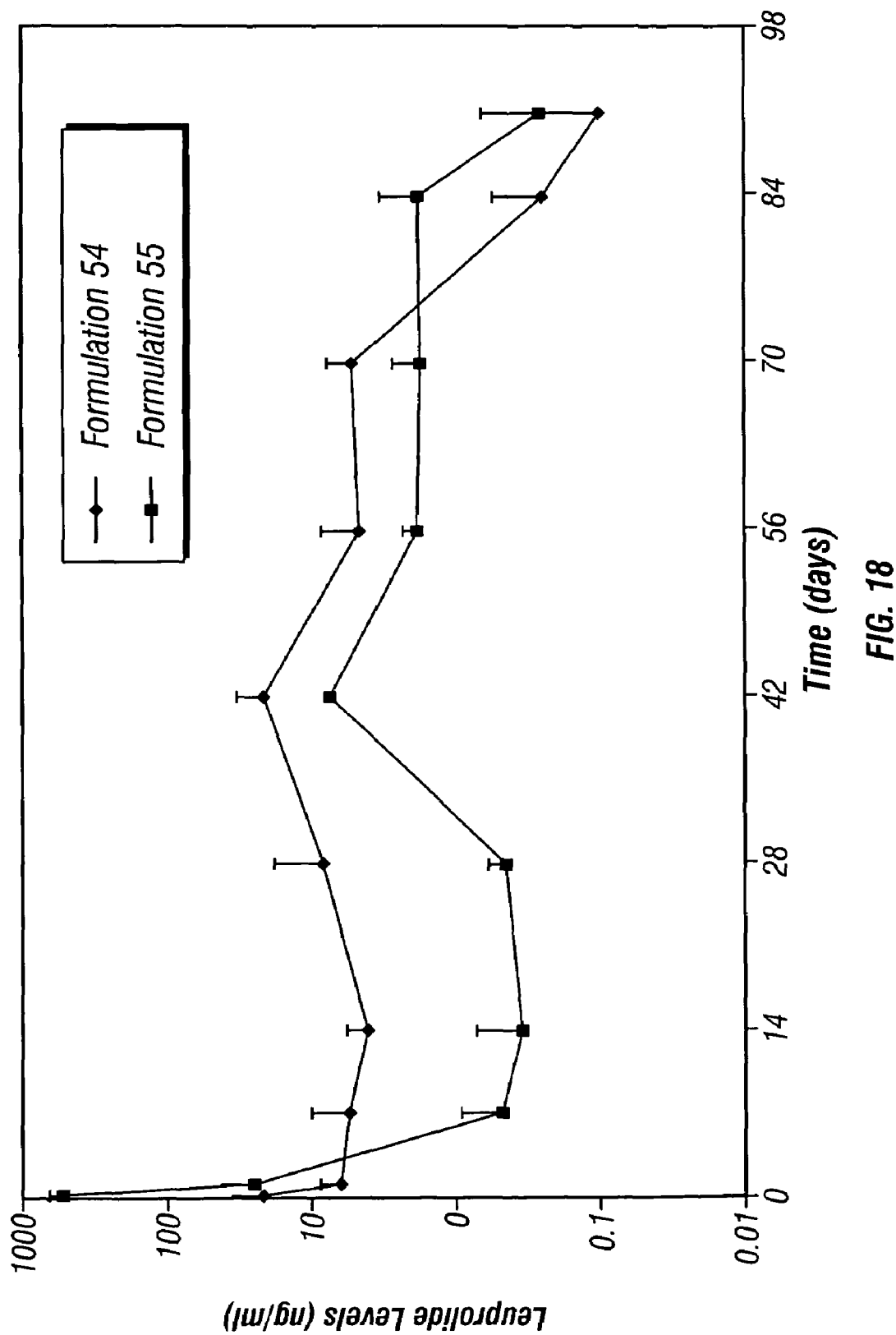
FIG. 18 is a graph illustrating the in vivo release profile of leuprolide acetate obtained from the 3-month depot formulation of the present invention (formulations 54 and 55).
Figure 19:
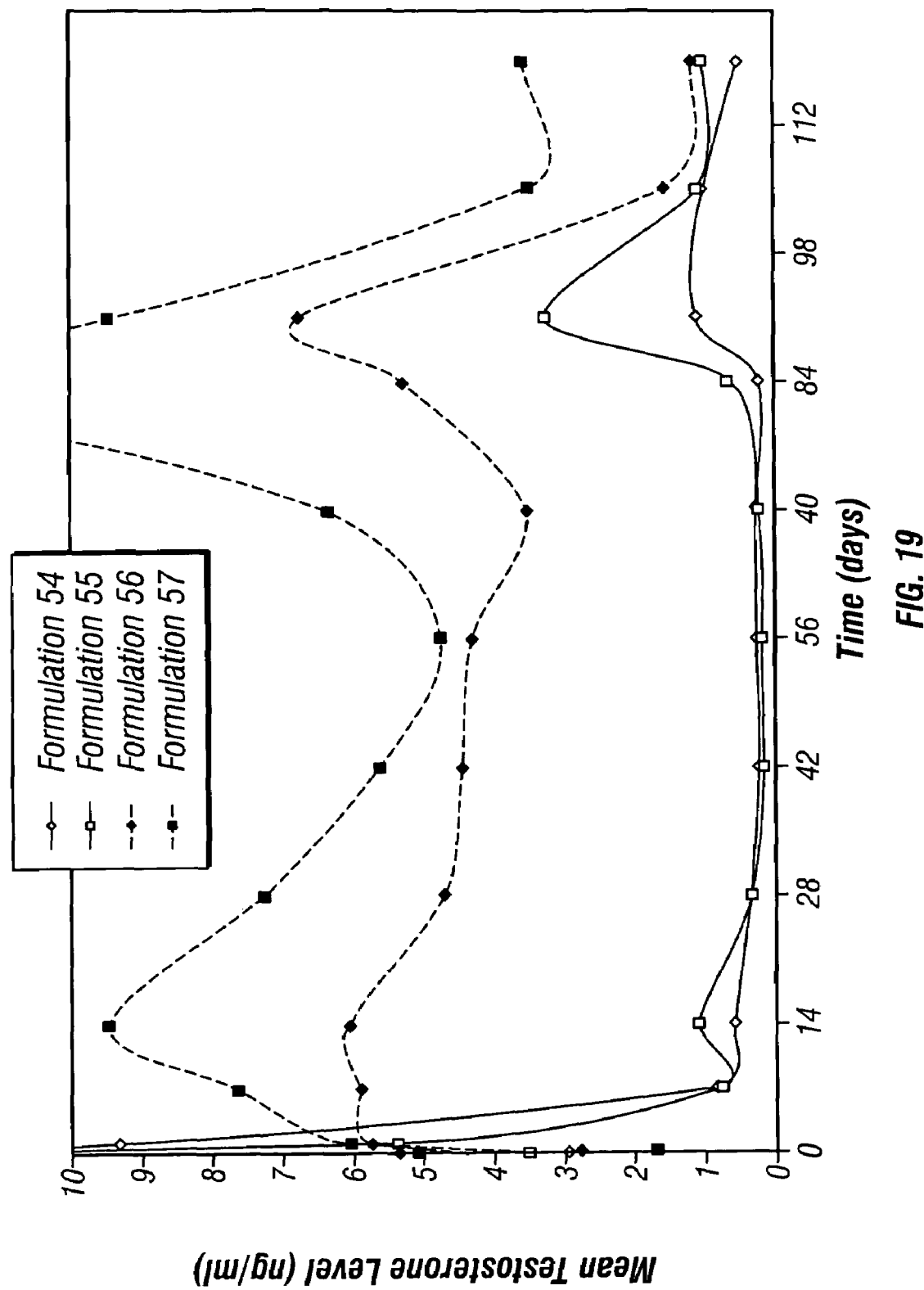
FIG. 19 is a graph illustrating the in vivo suppression of rat testosterone by the 3-month leuprolide acetate depot formulations of the present invention (formulations 54 and 55) as compared with the placebo formulations without leuprolide acetate (formulations 56 and 57).

In particular, FIG. 18 illustrates representative in vivo sustained release profiles of leuprolide acetate obtained in rats from depot formulations according to the present invention containing PLGA (L/G: 75/25) in both benzyl benzoate (BB) and benzyl alcohol (BA) for 3 months (formulations 54 and 55). FIG. 19 illustrates the testosterone profiles of the leuprolide acetate depot formulations (formulations 54 and 55) as compared to placebo depot formulation without leuprolide acetate (formulations 56 and 57). The leuprolide acetate depot formulations exhibited sustained release rate profiles for prolonged period of time, a duration greater than or equal to 3 months, and were efficacious in suppression of testosterone level in the rats to their castration level (<0.5 ng/mL) after 10-14 days as compared to the placebo formulations (4-5 ng/mL).

EXAMPLE 25

In Vivo Release Rate Profiles and Efficacy of Various Leuprolide Acetate Depot Formulations A representative number of implantable gels as tabulated in Table 12 were tested for in rats to determine in vivo release rate profiles and efficacy as measured by testosterone suppression as described in Example 23 above. In particular, the release rate profile of leuprolide and efficacy, i.e., testosterone suppression, were determined by measuring the blood serum or plasma concentrations of leuprolide and testosterone as a function of time, as illustrated in FIG. 20.

Figure 20:
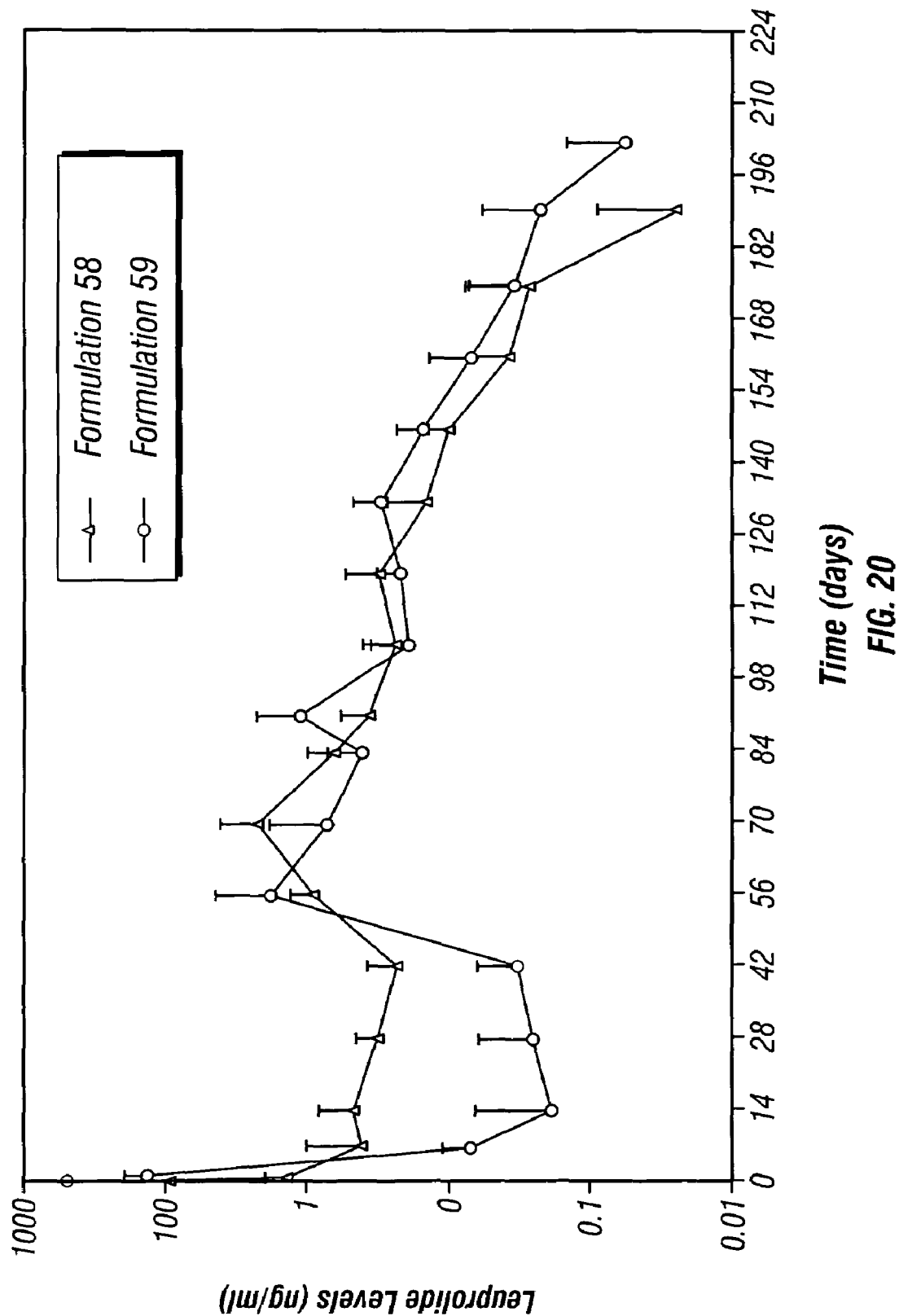
FIG. 20 is a graph illustrating the in vivo release profile of leuprolide acetate obtained from the 6-month depot formulation of the present invention (formulations 58 and 59).
Figure 21:
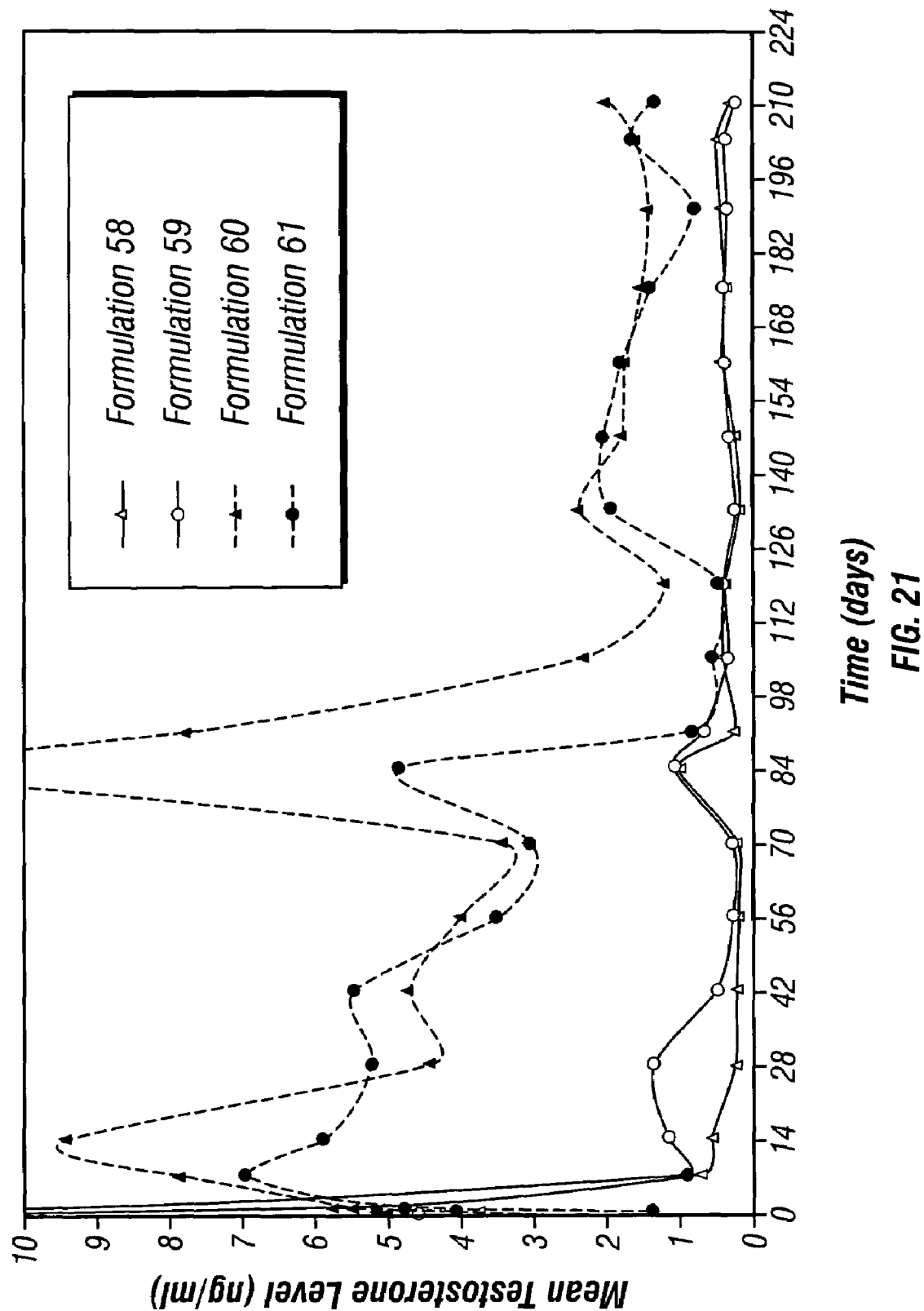
FIG. 21 is a graph illustrating the in vivo suppression of rat testosterone by the 6-month leuprolide acetate depot formulations of the present invention (formulations 58 and 59) as compared with the placebo formulations without leuprolide acetate (formulations 60 and 61).

In particular, FIG. 20 illustrates representative in vivo sustained release profiles of leuprolide acetate obtained in rats from depot formulations according to the present invention containing P(DL)LA in either benzyl benzoate (BB) or benzyl alcohol (BA) for 6 months (formulations 58 and 59). FIG. 21 illustrates the testosterone profiles of the leuprolide acetate depot formulations (formulations 58 and 59) as compared to the placebos without leuprolide acetate (formulation 60 and 61). The leuprolide acetate depot formulations exhibited sustained release rate profiles for a prolonged period of time, a duration greater than or equal to 6 months, and were efficacious in suppression of testosterone level in the rats to their castration level (<0.5 ng/mL) after 10-14 days as compared to the placebo formulations (4-5 ng/mL).

EXAMPLE 26

The above-described exemplary embodiments are intended to be illustrative in all respects, rather than restrictive, of the present invention. Thus present invention is capable of many variations in detailed implementation that can be derived from the description contained herein by a person skilled in the art. All such variations and modifications are considered to be within the scope and spirit of the present invention.

We claim:
1. An injectable depot composition for sustained delivery of a beneficial agent to a subject in a controlled manner over a predetermined duration of time after administration comprising:
   (a) a viscous gel formulation comprising:
      (1) a bioerodible, biocompatible polymer, wherein the polymer is a blend of polymers including at least one lactic acid-based polymer and wherein the blend of polymers has a monomer ratio of at least 50% lactic acid-based polymer; and
      (2) a solvent having a miscibility in water of less than or equal to 7 wt. % at 25° C., in an amount effective to plasticize the polymer and form a gel therewith; and
   (b) a beneficial agent dissolved or dispersed in the gel; wherein the duration of time is from about two weeks to about twelve months after administration.
2. The composition of claim 1, wherein the polymer is a copolymer of lactic acid and glycolic acid.
3. The composition of claim 1, wherein the polymer is a polylactide.
4. The composition of claim 2, wherein the polymer has L/G ratio of about 50:50 to about 100:0 and a molecular weight ranging from about 3,000 to about 120,000.
5. The composition of claim 1, comprising about 5 wt. % to about 90 wt. % of the bioerodible, biocompatible polymer.
6. The composition of claim 5, comprising about 25 wt. % to about 80 wt. % of the bioerodible, biocompatible polymer.
7. The composition of claim 5, comprising about 35 wt. % to about 75 wt. % of the bioerodible, biocompatible polymer.
8. The composition of claim 1, wherein the duration of time is equal to or greater than three months after administration.
9. The composition of claim 1, wherein the duration of time is from about 3 months to about 6 months after administration.
10. The composition of claim 1, wherein the duration of time is from about 3 months to about 9 months after administration.
11. The composition of claim 1, wherein the duration of time is from about 6 months to about 9 months after administration.
12. The composition of claim 1, wherein the viscous gel further comprises a polymer selected from the group consisting of polylactides, polyglycolides, caprolactone-based polymers, poly(caprolactone), polyanhydrides, polyamines, polyesteramides, polyorthoesters, polydioxanones, polyacetals, polyketals, polycarbonates, polyphosphoesters, polyesters, polybutylene terephthalate, polyorthocarbonates, polyphosphazenes, succinates, poly(malic acid), poly(amino acids), polyvinylpyrrolidone, polyethylene glycol, polyhydroxycellulose, polysaccharides, chitin, chitosan, hyaluronic acid, and copolymers, terpolymers and mixtures thereof, and biodegradable polymers and their copolymers including caprolactone-based polymers, polycaprolactones and copolymers which include polybutylene terephthalate.
13. The composition of claim 1, further including at least one of the following: a pore former; a solubility modulator for the beneficial agent; and an osmotic agent.
14. The composition of claim 1, wherein the solvent comprises a component solvent selected from the group consisting of triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, polyethylene glycol, octanol, ethyl lactate, propylene glycol, propylene carbonate, ethylenecarbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacyclo-heptan-2-one, and mixtures thereof.
15. The composition of claim 1, wherein the solvent is selected from an aromatic alcohol, lower alkyl and aralkyl esters of aryl acids; aryl, aralkyl and lower alkyl ketones; and lower alkyl esters of citric acid.
16. The composition of claim 1, wherein the solvent is benzyl alcohol.
17. The composition of claim 1, wherein the solvent is benzyl benzoate.

18. The composition of claim 1, wherein the solvent is ethyl benzoate.

19. The composition of claim 1, wherein the composition is free of solvents having a miscibility in water that is greater than 7 wt. % at 25° C.

20. The composition of claim 1, wherein the delivery is a systemic delivery.

21. The composition of claim 1, wherein the delivery is a local delivery.

22. The composition of claim 1, wherein the delivery is repeated after a period of time.

23. The composition of claim 1, wherein the delivery is provided at multiple sites.

24. An injectable depot composition for sustained delivery of a beneficial agent to a subject in a controlled manner over a predetermined duration of time after administration comprising:
  (a) a viscous gel formulation comprising:
    (1) a bioerodible, biocompatible polymer, wherein the polymer is a blend of polymers including at least one lactic acid-based polymer and wherein the blend of polymers has a monomer ratio of at least 50% lactic acid-based polymer; and
    (2) a solvent having a miscibility in water of less than or equal to 7 wt. % at 25° C., in an amount effective to plasticize the polymer and form a gel therewith; and
  (b) a beneficial agent dissolved or dispersed in the gel;
    wherein the beneficial agent is delivered systemically in a controlled manner over a duration of time from about two weeks to about twelve months after administration.

25. The composition of claim 24, wherein the polymer is a copolymer of lactic acid and glycolic acid.

26. The composition of claim 24, wherein the polymer is a polylactide.

27. The composition of claim 25, wherein the polymer has L/G ratio of about 50:50 to about 100:0 and a molecular weight ranging from about 3,000 to about 120,000.

28. The composition of claim 24, comprising about 5 wt. % to about 90 wt. % of the bioerodible, biocompatible polymer.

29. The composition of claim 28, comprising about 25 wt. % to about 80 wt. % of the bioerodible, biocompatible polymer.

30. The composition of claim 28, comprising about 35 wt. % to about 75 wt. % of the bioerodible, biocompatible polymer.

31. The composition of claim 24, wherein the duration of time is equal to or greater than three months after administration.

32. The composition of claim 24, wherein the duration of time is from about 3 months to about 6 months after administration.

33. The composition of claim 24, wherein the duration of time is from about 3 months to about 9 months after administration.

34. The composition of claim 24, wherein the duration of time is from about 6 months to about 9 months after administration.

35. The composition of claim 24, wherein the viscous gel further comprises a polymer selected from the group consisting of polylactides, polyglycolides, caprolactone-based polymers, poly(caprolactone), polyanhydrides, polyamines, polyesteramides, polyorthoesters, polydioxanones, polyacetals, polyketals, polycarbonates, polyphosphoesters, polyesters, polybutylene terephthalate, polyorthocarbonates, polyphosphazenes, succinates, poly(malic acid), poly(amino acids), polyvinylpyrrolidone, polyethylene glycol, polyhydroxycellulose, polysaccharides, chitin, chitosan, hyaluronic acid, and copolymers, terpolymers and mixtures thereof.

36. The composition of claim 24, further including at least one of the following: a pore former; a solubility modulator for the beneficial agent; and an osmotic agent.

37. The composition of claim 24, wherein the solvent comprises a component solvent selected from the group consisting of triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacyclo-heptan-2-one, and mixtures thereof.

38. The composition of claim 24, wherein the solvent is selected from an aromatic alcohol, lower alkyl and aralkyl esters of aryl acids; aryl, aralkyl and lower alkyl ketones; and lower alkyl esters of citric acid.

39. The composition of claim 24, wherein the solvent is benzyl alcohol.

40. The composition of claim 24, wherein the solvent is benzyl benzoate.

41. The composition of claim 24, wherein the solvent is ethyl benzoate.

42. The composition of claim 24, wherein the composition is free of solvents having a miscibility in water that is greater than 7 wt. % at 25° C.

43. The composition of claim 24, wherein the delivery is repeated after a period of time.

44. The composition of claim 24, wherein the delivery is provided at multiple sites.

45. An injectable depot composition for sustained delivery of a beneficial agent to a subject in a controlled manner over a predetermined duration of time after administration comprising:
  (a) a viscous gel formulation comprising:
    (1) a bioerodible, biocompatible polymer, wherein the polymer is a blend of polymers including at least one lactic acid-based polymer and wherein the blend of polymers has a monomer ratio of at least 50% lactic acid-based polymer; and
    (2) a solvent having a miscibility in water of less than or equal to 7 wt. % at 25° C., in an amount effective to plasticize the polymer and form a gel therewith; and
  (b) a beneficial agent dissolved or dispersed in the gel;
    wherein the beneficial agent is delivered locally in a controlled manner over a duration of time from about two weeks to about twelve months after administration.

46. The composition of claim 45, wherein the polymer is a copolymer of lactic acid and glycolic acid.

47. The composition of claim 45, wherein the polymer is a polylactide.

48. The composition of claim 45, wherein the polymer has L/G ratio of about 50:50 to about 100:0 and a molecular weight ranging from about 3,000 to about 120,000.

49. The composition of claim 45, comprising about 5 wt. % to about 90 wt. % of the bioerodible, biocompatible polymer.

50. The composition of claim 49, comprising about 25 wt. % to about 80 wt. % of the bioerodible, biocompatible polymer.

51. The composition of claim 50, comprising about 35 wt. % to about 75 wt. % of the bioerodible, biocompatible polymer.

52. The composition of claim 45, wherein the duration of time is equal to or greater than three months after administration.

53. The composition of claim 45, wherein the duration of time is from about 3 months to about 6 months after administration.

54. The composition of claim 45, wherein the duration of time is from about 3 months to about 9 months after administration.

55. The composition of claim 45, wherein the duration of time is from about 6 months to about 9 months after administration.

56. The composition of claim 45, wherein the viscous gel further comprises a polymer selected from the group consisting of polylactides, polyglycolides, caprolactone-based polymers, poly(caprolactone), polyanhydrides, polyamines, polyesteramides, polyorthoesters, polydioxanones, polyacetals, polyketals, polycarbonates, polyphosphoesters, polyesters, polybutylene terephthalate, polyorthocarbonates, polyphosphazenes, succinates, poly(malic acid), poly(amino acids), polyvinylpyrrolidone, polyethylene glycol, polyhydroxycellulose, polysaccharides, chitin, chitosan, hyaluronic acid, and copolymers, terpolymers and mixtures thereof.

57. The composition of claim 45, further including at least one of the following: a pore former; a solubility modulator for the beneficial agent; and an osmotic agent.

58. The composition of claim 45, wherein the solvent comprises a component solvent selected from the group consisting of triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacyclo-hcptan-2-one, and mixtures thereof.

59. The composition of claim 45, wherein the solvent is selected from an aromatic alcohol, lower alkyl and aralkyl esters of aryl acids; aryl, aralkyl and lower alkyl ketones; and lower alkyl esters of citric acid.

60. The composition of claim 45, wherein the solvent is benzyl alcohol.

61. The composition of claim 45, wherein the solvent is benzyl benzoate.

62. The composition of claim 45, wherein the solvent is ethyl benzoate.

63. The composition of claim 45, wherein the composition is free of solvents having a miscibility in water that is greater than 7 wt. % at 25° C.

64. The composition of claim 45, wherein the delivery is repeated after a period of time.

65. The composition of claim 45, wherein the delivery is provided at multiple sites.

66. An injectable depot composition for sustained delivery of a beneficial agent to a subject in a controlled manner over a predetermined duration of time after administration comprising:

(a) a viscous gel formulation comprising:
(1) a bioerodible, biocompatible blend of polymers, wherein the polymer is a blend of polymers including at least one lactic acid-based polymer and wherein the blend of polymers has a monomer ratio of at least 50% lactic acid-based polymer; and
(2) a solvent having a miscibility in water of less than or equal to 7 wt. % at 25° C., in an amount effective to plasticize the blend of the polymers and form a gel therewith; and
(b) a beneficial agent dissolved or dispersed in the gel; wherein the duration of time is from about two weeks to about twelve months after administration.

67. The composition of claim 66, wherein the blend of the polymers includes a copolymer of lactic acid and glycolic acid.

68. The composition of claim 66, wherein the blend of the polymers includes a polymer having an L/G ratio of about 50:50 to about 100:0 and a molecular weight ranging from about 3,000 to about 120,000.

69. The composition of claim 66, comprising about 5 wt. % to about 90 wt. % of the bioerodible, biocompatible blend of the polymers.

70. The composition of claim 69, comprising about 25 wt. % to about 80 wt. % of the bioerodible, biocompatible blend of the polymers.

71. The composition of claim 69, comprising about 35 wt. % to about 75 wt. % of the bioerodible, biocompatible blend of the polymers.

72. The composition of claim 66, wherein the duration of time is equal to or greater than three months after administration.

73. The composition of claim 66, wherein the duration of time is from about 3 months to about 6 months after administration.

74. The composition of claim 66, wherein the duration of time is from about 3 months to about 9 months after administration.

75. The composition of claim 66, wherein the duration of time is from about 6 months to about 9 months after administration.

76. The composition of claim 66, wherein the viscous gel further comprises a polymer selected from the group consisting of polylactides, polyglycolides, caprolactone-based polymers, poly(caprolactone), polyanhydrides, polyamines, polyesteramides, polyorthoesters, polydioxanones, polyacetals, polyketals, polycarbonates, polyphosphoesters, polyesters, polybutylene terephthalate, polyorthocarbonates, polyphosphazenes, succinates, poly(malic acid), poly(amino acids), polyvinylpyrrolidone, polyethylene glycol, polyhydroxycellulose, polysaccharides, chitin, chitosan, hyaluronic acid, and copolymers, terpolymers and mixtures thereof.

77. The composition of claim 66, further including at least one of the following: a pore former; a solubility modulator for the beneficial agent; and an osmotic agent.

78. The composition of claim 66, wherein the solvent comprises a component solvent selected from the group consisting of triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacyclo-heptan-2-one, and mixtures thereof.

79. The composition of claim 66, wherein the solvent is selected from an aromatic alcohol, lower alkyl and aralkyl esters of aryl acids; aryl, aralkyl and lower alkyl ketones; and lower alkyl esters of citric acid.

80. The composition of claim 66, wherein the solvent is benzyl alcohol.

81. The composition of claim 66, wherein the solvent is benzyl benzoate.

82. The composition of claim 66, wherein the solvent is ethyl benzoate.

83. The composition of claim 66, wherein the composition is free of solvents having a miscibility in water that is greater than 7 wt. % at 25° C.

84. The composition of claim 66, wherein the delivery is a systemic delivery.

85. The composition of claim 66, wherein the delivery is a local delivery.

86. The composition of claim 66, wherein the delivery is repeated after a period of time.

87. The composition of claim 66, wherein the delivery is provided at multiple sites.

88. An injectable depot composition for sustained delivery of a beneficial agent to a subject in a controlled manner over a predetermined duration of time after administration comprising:
 (a) a viscous gel formulation comprising:
  (1) a bioerodible, biocompatible blend of polymers, wherein the polymer is a blend of polymers including at least one lactic acid-based polymer and wherein the blend of polymers has a monomer ratio of at least 50% lactic acid-based polymer; and
  (2) a solvent having a miscibility in water of less than or equal to 7 wt. % at 25° C., in an amount effective to plasticize the blend of the polymers and form a gel therewith; and
 (b) a beneficial agent dissolved or dispersed in the gel;
 wherein the beneficial agent is delivered systemically in a controlled manner over a duration of time from about two weeks to about twelve months after administration.

89. An injectable depot composition for sustained delivery of a beneficial agent to a subject in a controlled manner over a predetermined duration of time after administration comprising:
 (a) a viscous gel formulation comprising:
  (1) a bioerodible, biocompatible blend of polymers wherein the polymer is a blend of polymers including at least one lactic acid-based polymer and wherein the blend of polymers has a monomer ratio of at least 50% lactic acid-based polymer; and
  (2) a solvent having a miscibility in water of less than or equal to 7 wt. % at 25° C., in an amount effective to plasticize the blend of the polymers and form a gel therewith; and
 (b) a beneficial agent dissolved or dispersed in the gel;
 wherein the beneficial agent is delivered locally in a controlled manner over a duration of time from about two weeks to about twelve months after administration.

* * * * *